United States Patent
Zhu et al.

(10) Patent No.: US 7,557,107 B2
(45) Date of Patent: Jul. 7, 2009

(54) FARNESYL PROTEIN TRANSFERASE INHIBITORS AS ANTITUMOR AGENTS

(75) Inventors: Hugh Y. Zhu, Scotch Plains, NJ (US); Alan B. Cooper, West Caldwell, NJ (US); Jagdish A. Desai, Monroe Township, NJ (US); James J-S Wang, Westfield, NJ (US); Ronald J. Doll, Convent Station, NJ (US); F. George Njoroge, Warren, NJ (US); Viyyoor M. Girijavallabhan, Parsippany, NJ (US)

(73) Assignee: Schering Coporation, Kenilworth, NJ (US)

(*) Notice: Subject to any disclaimer, the term of this patent is extended or adjusted under 35 U.S.C. 154(b) by 782 days.

(21) Appl. No.: 10/911,340

(22) Filed: Aug. 4, 2004

(65) Prior Publication Data

US 2005/0059672 A1    Mar. 17, 2005

Related U.S. Application Data

(60) Provisional application No. 60/498,509, filed on Aug. 28, 2003, provisional application No. 60/493,269, filed on Aug. 7, 2003.

(51) Int. Cl.
*A61K 31/497* (2006.01)
(52) U.S. Cl. .................. 514/253.03; 544/361
(58) Field of Classification Search ............ 514/253.03; 544/361
See application file for complete search history.

(56) References Cited

U.S. PATENT DOCUMENTS

| 5,874,442 A | 2/1999 | Doll et al. |
| 2003/0229099 A1 | 12/2003 | Zhu et al. |
| 2004/0122018 A1* | 6/2004 | Zhu et al. ............. 514/253.04 |
| 2006/0205755 A1 | 9/2006 | Cooper et al. |

FOREIGN PATENT DOCUMENTS

| WO | WO 95/10516 | 4/1995 |
| WO | WO 97/23478 | 7/1997 |
| WO | WO 02/18368 A1 | 3/2002 |
| WO | WO 03/047586 A1 | 6/2003 |
| WO | WO 03/072549 | 9/2003 |

OTHER PUBLICATIONS

PCT International Search Report dated Dec. 28, 2004 for corresponding PCT Application No. PCT/US2004/025042.
Schering-Plough Discontinues Phase III Clinical Study of Sarasar(TM) (Lonafarnib) in Non-Small-Cell Lung Cancer, Schering-Plough Press Release, Feb. 5, 2004.

* cited by examiner

*Primary Examiner*—James O. Wilson
*Assistant Examiner*—Ebenezer Sackey
(74) *Attorney, Agent, or Firm*—Henry C. Jeanette

(57) ABSTRACT

Disclosed are novel tricyclic compounds of the formula:

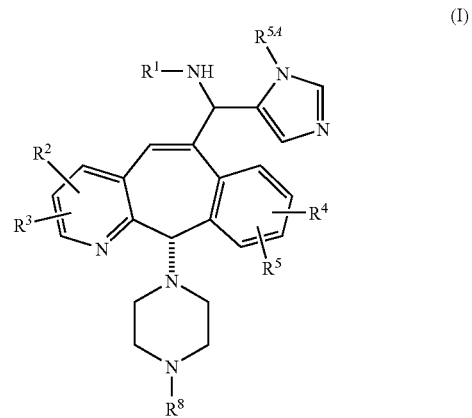

and a pharmaceutically acceptable salts or solvates thereof. The compounds are useful for inhibiting farnesyl protein transferase. Also disclosed are pharmaceutical compositions comprising the compounds of formula (I). Also disclosed are uses of the compounds of formula (I) for the manufacture of a medicament for the treatment of cancer.

32 Claims, No Drawings

US 7,557,107 B2

FARNESYL PROTEIN TRANSFERASE INHIBITORS AS ANTITUMOR AGENTS

REFERENCE TO RELATED APPLICATIONS

This Application claims the benefit of U.S. Provisional Application Ser. No. 60/493,269 filed on Aug. 7, 2003, and U.S. Provisional Application Ser. No. 60/498,509 filed Aug. 28, 2003.

BACKGROUND

WO 95/10516, published Apr. 20, 1995, WO 97/23478, published Jul. 3, 1997, WO 02/18368 published Mar. 7, 2002, U.S. 2002/0198216 published Dec. 26, 2002, and U.S. Pat. No. 5,874,442 issued Feb. 23, 1999 disclose tricyclic compounds useful for inhibiting farnesyl protein transferase.

WO 98/54966 published Dec. 10, 1998 discloses methods of treating cancer by administering at least two therapeutic agents selected from a group consisting of a compound which is an antineoplastic agent and a compound which is an inhibitor of prenyl-protein transferase (e.g., a farnesyl protein transferase inhibitor).

U.S. Pat. No. 6,096,757 issued Aug. 1, 2000 discloses methods of treating proliferative diseases (e.g., cancers) by administering an FPT inhibitor in conjunction with an antineoplastic agent and/or radiation.

Shih et al., "The farnesyl protein transferase inhibitor SCH66336 synergizes with taxanes in vitro and enhances their antitumor activity in vivo", Cancer Chemother Pharmacol (2000) 46: 387-393 discloses a study of the combination of SCH 66336 with paclitaxel, and SCH 66336 with docetaxel on certain cancer cell lines.

WO 01/45740 published Jun. 28, 2001 discloses a method of treating cancer (breast cancer) comprising administering a selective estrogen receptor modulator (SERM) and at least one farnesyl transferase inhibitor (FTI). FTI-277 is the exemplified FTI.

The WEB site http://www.osip.com/press/pr/07-25-01 discloses a press release of OSI Pharmaceuticals. The press release announces the initiation of a Phase III clinical trial evaluating the use of the epidermal growth factor inhibitor Tarceva (TM) (OSI-774) in combination with Carboplatin (Paraplatin®) and Paclitaxel (Taxol®) for the treatment of Non Small Cell Lung Cancer.

The WEB site http://cancertrials.nci.nih.gov/types/lung/iressa12100.html in a disclosure posted Dec. 14, 2000 discloses the following list of open clinical trials for advanced (stage IIIB and IV) non-small cell lung cancer, from NCI's clinical trials database:
 (1) phase III Randomized Study of ZD 1839 (IRESSA, an epidermal growth factor inhibitor) combined with gemcitabine and cisplatin in chemotherapy-naive patients with Stage IIIB or IV non-small cell lung cancer; and
 (2) phase III Randomized Study of ZD 1839 (IRESSA, an epidermal growth factor inhibitor) combined with paclitaxel and carboplatin in chemotherapy-naive patients with Stage IIIB or IV non-small cell lung cancer.

WO 01/56552 published Aug. 9, 2001 discloses the use of an FPT inhibitor for the preparation of a pharmaceutical composition for treating advanced breast cancer. The FPT inhibitor may be used in combination with one or more other treatments for advanced breast cancer especially endocrine therapy such as an antiestrogen agent such as an estrogen receptor antagonist (e.g., tamoxifen) or a selective estrogen receptor modulator or an aromatase inhibitor. Other anti-cancer agents which may be employed include, amongst others, platinum coordination compounds (such as cisplatin or carboplatin), taxanes (such as paclitaxel or docetaxel), anti-tumor nucleoside derivatives (such as gemcitabine), and HER2 antibodies (such as trastzumab).

WO 01/62234 published Aug. 30, 2001 discloses a method of treatment and dosing regimen for treating mammalian tumors by the discontinuous administration of a farnesyl transferase inhibitor over an abbreviated one to five day dosing schedule. Disclosed is a regimen wherein the farnesyl protein transferase inhibitor is administered over a one to five day period followed by at least two weeks without treatment. It is disclosed that in previous studies farnesyl protein transferase inhibitors have been shown to inhibit the growth of mammalian tumors when administered as a twice daily dosing schedule. It is further disclosed that the administration of a farnesyl protein transferase inhibitor in a single dose daily for one to five days produced a marked suppression of tumor growth lasting one to at least 21 days. It is also disclosed that the FTI may be used in combination with one or more other anti-cancer agents such as, platinum coordination compounds (e.g., cisplatin or carboplatin), taxane compounds (e.g., paclitaxel or docetaxel), anti-tumor nucleoside derivatives (e.g., gemcitabine), HER2 antibodies (e.g., trastzumab), and estrogen receptor antagonists or selective estrogen receptor modulators (e.g., tamoxifen).

WO 01/64199 published Sep. 7, 2001 discloses a combination of particular FPT inhibitors with taxane compounds (e.g., paclitaxel or docetaxel) useful in the treatment of cancer.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds (FPT inhibitors) of formula I:

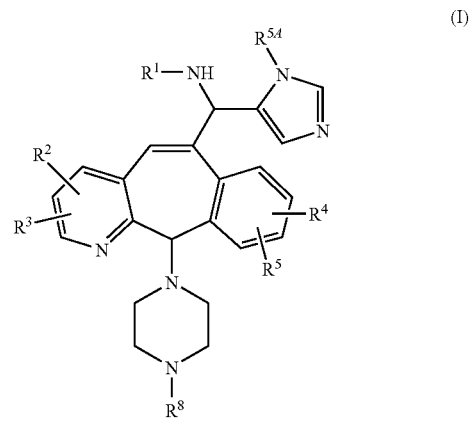

(I)

and the pharmaceutically acceptable salts or solvates thereof, wherein the substitutents are defined below.

This invention also provides compounds (FPT inhibitors) of formulas 100 to 174, as described below, or a pharmaceutically acceptable salt or solvate thereof.

This invention also provides compounds (FPT inhibitors) of formulas 100.1 to 102.2, 103.1 to 135.2, and 136.1 to 174.1, as described below, or a pharmaceutically acceptable salt or solvate thereof.

This invention also provides pharmaceutical compositions comprising an effective amount of at least one (usually one) compound of this invention and a pharmaceutically acceptable carrier.

This invention also provides a method of inhibiting farnesyl protein transferase in a patient in need of such treatment comprising administering to said patient an effective amount of at least one (usually one) compound of this invention.

This invention also provides methods of treating (or inhibiting) tumors (i.e., cancers) in a patient in need of such treatment comprising administering to said patient an effective amount of at least one (usually one) compound of this invention.

This invention also provides methods of treating (or inhibiting) tumors (i.e., cancers) in a patient in need of such treatment comprising administering to said patient an effective amount of at least one (usually one) compound of this invention in combination with at least one (e.g., 1 or 2) chemotherapeutic agent (also know in the art as antineoplastic agent or anticancer agent).

This invention also provides methods of treating (or inhibiting) tumors (i.e., cancers) in a patient in need of such treatment comprising administering to said patient an effective amount of at least one (usually one) compound of this invention in combination with at least one chemotherapeutic agent (also know in the art as antineoplastic agent or anticancer agent) and/or radiation.

This invention also provides methods of treating (or inhibiting) tumors (i.e., cancers) in a patient in need of such treatment comprising administering to said patient an effective amount of at least one (usually one) compound of this invention in combination with at least one signal transduction inhibitor.

This invention provides methods of treating breast cancer (i.e., postmenopausal and premenopausal breast cancer, e.g., hormone-dependent breast cancer) in a patient in need of such treatment wherein said treatment comprises the administration of at least one (e.g., one) compound of formula 1.0 with hormonal therapies (i.e., antihormonal agents).

The methods of this invention include the treatment of hormone-dependent metastatic and advanced breast cancer, adjuvant therapy for hormone-dependent primary and early breast cancer, the treatment of ductal carcinoma in situ, and the treatment of inflammatory breast cancer in situ.

Optionally, neoadjuvant therapy (i.e., the use of chemotherapeutic agents) is used in combination with the compounds of formula 1.0 and hormonal therapies in the methods of this invention.

The methods of this invention can also be used to prevent breast cancer in patients having a high risk of developing breast cancer.

In the methods of this invention the compounds of this invention can be administered concurrently or sequentially (i.e., consecutively) with the chemotherapeutic agents or the signal transduction inhibitor.

Optionally, radiation treatment can be administered in the methods of this invention.

DETAILED DESCRIPTION OF THE INVENTION

As described herein, unless otherwise indicated, the use of a drug or compound in a specified period (e.g., once a week, or once every three weeks, etc.,) is per treatment cycle.

As used herein, unless otherwise specified, "at least one", as used in reference to the number of compounds or chemotherapeutics or drugs used, represents one or more (e.g., 1-6), more preferably 1-4, with 1, 2 or 3 being most preferred.

As used herein, unless otherwise specified, the following terms have the following meanings:

antineoplastic agent-represents a chemotherapeutic agent effective against cancer;

compound-with reference to the antineoplastic agents, includes the agents that are antibodies;

concurrently-represents (1) simultaneously in time (e.g., at the same time); or (2) at different times during the course of a common treatment schedule;

consecutively-means one following the other;

different-as used in the phrase "different antineoplastic agents" means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound;

effective amount-represents a therapeutically effective amount; for example, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor; for example, in the treatment of lung cancer (e.g., non small cell lung cancer) a therapeutically effective amount is that amount that alleviates or eliminates cough, shortness of breath and/or pain; also, for example, a therapeutically effective amount of the FPT inhibitor is that amount which results in the reduction of farnesylation; the reduction in farnesylation may be determined by the analysis of pharmacodynamic markers such as Prelamin A and HDJ-2 (DNAJ-2) using techniques well known in the art;

patient-represents an animal, such as a mammal (e.g., a human being);

sequentially-represents (1) administration of one component of the method ((a) compound of the invention, or (b) chemotherapeutic agent, signal transduction inhibitor and/or radiation therapy) followed by administration of the other component or components; after adminsitration of one component, the next component can be administered substantially immediately after the first component, or the next component can be administered after an effective time period after the first component; the effective time period is the amount of time given for realization of maximum benefit from the administration of the first component;

alkenyl-represents straight and branched carbon chains having at least one carbon to carbon double bond and containing from 2-12 carbon atoms, preferably from 2 to 6 carbon atoms and most preferably from 3 to 6 carbon atoms;

alkyl-represents straight and branched carbon chains and contains from one to twenty carbon atoms, preferably one to six carbon atoms, more preferably one to four carbon atoms; even more preferably one to two carbon atoms;

alkynyl-represents straight and branched carbon chains having at least one carbon to carbon triple bond and containing from 2-12 carbon atoms, preferably from 2 to 6 carbon atoms and most preferably from 2 to 4 carbon atoms;

aryl-represents a carbocyclic group containing from 6 to 15 carbon atoms in the unsubstituted carbocyclic group and having at least one aromatic ring (e.g., aryl is a phenyl ring), with all available substitutable carbon atoms of the carbocyclic group being intended as possible points of attachment of said aryl group, said aryl group being unsubstituted or substituted, said substituted aryl group having one or more (e.g., 1 to 3) substituents independently selected from the group consisting of: halo, alkyl, hydroxy, alkoxy, phenoxy, $CF_3$, —$C(O)N(R^{18})_2$, —$SO_2R^{18}$, —$SO_2N(R^{18})_2$, amino, alkylamino, dialkylamino, —$COOR^{23}$ and —$NO_2$ (preferably said substitutents are independently selected from the group consisting of: alkyl (e.g., $C_1$-$C_6$ alkyl), halogen (e.g., Cl and Br), —$CF_3$ and —OH), wherein each $R^{18}$ is independently selected from the group consisting of: H, alkyl, aryl, arylalkyl, heteroaryl and cycloalkyl, and wherein $R^{23}$ is selected from the group consisting of: alkyl and aryl;

arylalkyl-represents an alkyl group, as defined above, substituted with an aryl group, as defined above;

arylheteroalkyl-represents a heteroalkyl group, as defined below, substituted with an aryl group, as defined above;

aryloxy-represents an aryl moiety, as defined above, covalently bonded to an adjacent structural element through an oxygen atom, for example, —O-phenyl (i.e., phenoxy);

cycloalkenyl-represents unsaturated carbocyclic rings of from 3 to 20 carbon atoms in the unsubstituted ring, preferably 3 to 7 carbon atoms, said cycloalkenyl ring comprising at least one (usually one) double bond, and said cycloalkenyl ring being unsubstituted or substituted, said substituted cycloalkenyl ring having one or more (e.g., 1, 2 or 3) substituents independently selected from the group consisting of: alkyl (e.g., methyl and ethyl), halogen, —$CF_3$ and —OH;

cycloalkyl-represents saturated carbocyclic rings of from 3 to 20 carbon atoms in the unsubstituted ring, preferably 3 to 7 carbon atoms, said cycloalkyl ring being unsubstituted or substituted, said substituted cycloalkyl ring having one or more (e.g., 1, 2 or 3) substituents independently selected from the group consisting of: alkyl (e.g., methyl and ethyl), halogen, —$CF_3$ and —OH; for example, 1-substituted cycloalkyl rings, such as, for example,

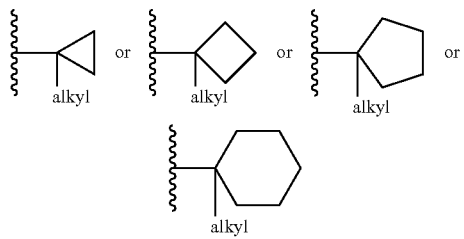

wherein said alkyl is generally a $C_1$-$C_6$ alkyl group, usually a $C_1$-$C_2$ alkyl group, and preferably a methyl group; thus, examples of cycloalkyl rings substituted at the 1-position with methyl include but are not limited to:

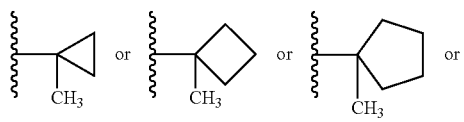

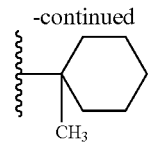

cycloalkylalkyl-represents an alkyl group, as defined above, substituted with a cycloalkyl group, as defined above;

halo (or halogen)-represents fluoro, chloro, bromo or iodo;

heteroalkenyl-represents straight and branched carbon chains having at least one carbon to carbon double bond and containing from two to twenty carbon atoms, preferably two to six carbon atoms interrupted by 1 to 3 heteroatoms selected from the group consisting of:— O—, —S— and —N—, provided that when there is more than one heteroatom, the heteroatoms are not adjacent to one another;

heteroalkyl-represents straight and branched carbon chains containing from one to twenty carbon atoms, preferably one to six carbon atoms interrupted by 1 to 3 heteroatoms selected from the group consisting of:—O—, —S— and —N—, provided that when there is more than one heteroatom, the heteroatoms are not adjacent to one another;

heteroalkynyl-represents straight and branched carbon chains having at least one carbon to carbon triple bond and containing from two to twenty carbon atoms, preferably two to six carbon atoms interrupted by 1 to 3 heteroatoms selected from the group consisiting of: —O—, —S— and —N-provided that when there is more than one heteroatom, the heteroatoms are not adjacent to one another;

heteroaryl-represents unsubstituted or substituted cyclic groups, having at least one heteroatom selected from the group consisting of: O, S or N (provided that any O and S atoms are not adjacent to one another), said heteroaryl group comprises O and S atoms, said heteroatom interrupting a carbocyclic ring structure and having a sufficient number of delocalized pi electrons to provide aromatic character, with the unsubstituted heteroaryl group preferably containing from 2 to 14 carbon atoms, wherein said substituted heteroaryl group is substituted with one or more (e.g., 1, 2 or 3) of the same or different substituents selected from the group consisting of: (1) halo; (2) —$CF_3$; (3) —$OR^{30}$ wherein $R^{30}$ is selected from the group consisting of: H, alkyl, aryl, and arylalkyl; (4) $COR^{30}$ wherein $R^{30}$ is as defined above; (5) —$SR^{30}$ wherein $R^{30}$ is as defined above; (6) —$S(O)tR^{35}$ wherein $R^{15}$ is selected from the group consisting of: aryl and alkyl; (7) —$N(R^{30})_2$ wherein $R^{30}$ is as defined above; (8) —$NO_2$; (9) —$OC(O)R^{30}$ wherein $R^{30}$ is as defined above; (10) $CO_2R$ wherein $R^{30}$ is as defined above; (11) —$OCO_2R^{35}$ wherein $R^{35}$ is as defined above; (12) —CN; (13) —$NR^{30}COOR^{35}$ wherein $R^{30}$ and $R^{35}$ are as defined above; (14) —$SR^{35}C(O)OR^{35}$ wherein $R^{35}$ is as defined above; (15) benzotriazol-1-yloxy; (16) tetrazol-5-ylthio; (17) substituted tetrazol-5-ylthio; (18) alkynyl; (19) alkenyl; (20) alkyl; (21) alkyl substituted with one or more (e.g., 1, 2 or 3) substitutents independently selected from the group consisting of: halogen, —$OR^{30}$ and —$CO_2R^{30}$ wherein $R^{30}$ is as defined above; and (22) alkenyl substituted with one or more (e.g., 1, 2 or 3) substituents independently selected from the group consisting of: halogen, —$OR^{30}$ and —CO$_2$R$^{30}$ wherein R$^{30}$ is as defined above; examples of heteroaryl groups include but are not limited to: e.g., 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, triazolyl, 2-, 3- or 4-pyridyl, or 2-, 3- or 4-pyridyl N-oxide, wherein pyridyl N-oxide can be represented as:

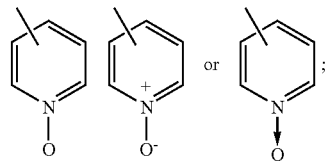

heteroarylalkenyl-represents an alkenyl group, as defined above, substituted with a heteroaryl group, as defined below;

heteroarylalkyl-represents an alkyl group, as defined above, substituted with a heteroaryl group, as defined above;

heterocycloalkylalkyl-represents an alkyl group, as defined above, substituted with a heterocycloalkyl group, as defined below;

heterocycloalkyl-represents a saturated carbocylic ring containing from 3 to 15 carbon atoms, preferably from 4 to 6 carbon atoms, which carbocyclic ring is interrupted by 1 to 3 hetero groups selected from the group consisting of:—O—, —S— or —NR$^{24}$ wherein R$^{24}$ is selected from the group consisting of: H, alkyl, aryl, and —C(O)N(R$^{18}$)$_2$ wherein R$^{18}$ is as above defined, examples of heterocycloalkyl groups include but are not limited to: 2- or 3-tetrahydrofuranyl, 2- or 3-tetrahydrothienyl, 2-, 3- or 4-piperidinyl, 2- or 3-pyrrolidinyl, 1-, 2-, 3-, or 4-piperizinyl, 2- or 4-dioxanyl, morpholinyl, and

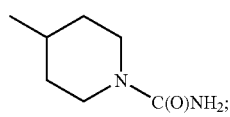

and heterocycloalkylalkyl-represents an alkyl group, as defined above, substituted with a heterocycloalkyl group, as above.

The positions in the tricyclic ring system are:

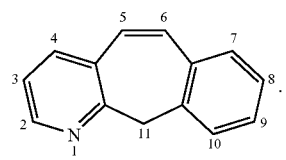

As well known in the art, a bond drawn from a particular atom wherein no moiety is depicted at the terminal end of the bond indicates a methyl group bound through that bond to the atom. For example:

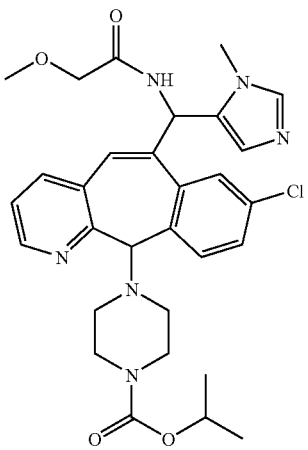

represents

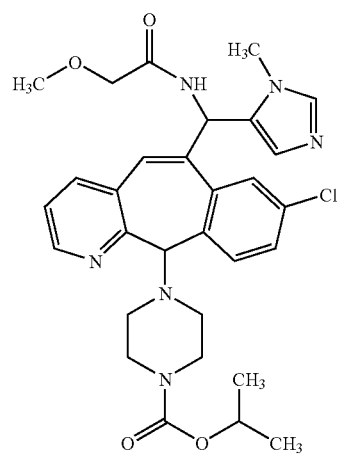

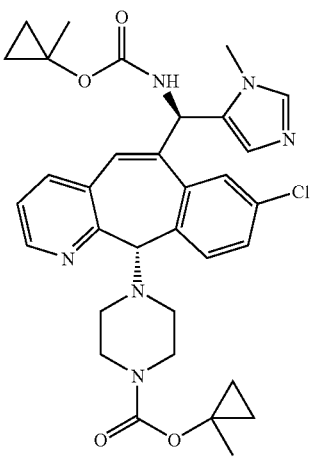

represents

-continued
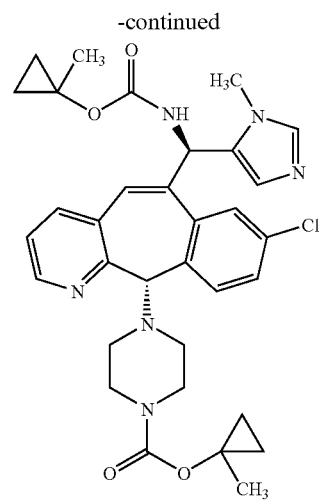
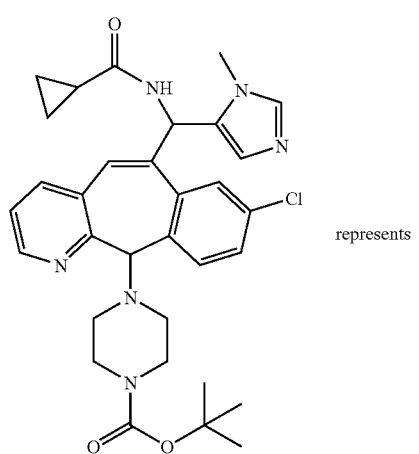
represents
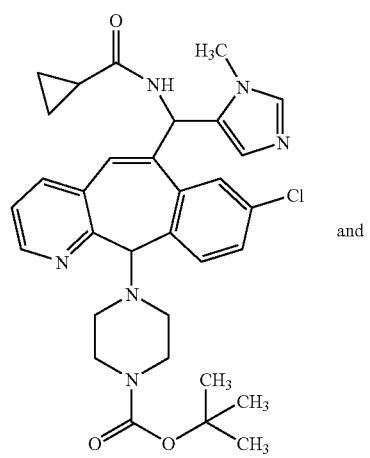
and
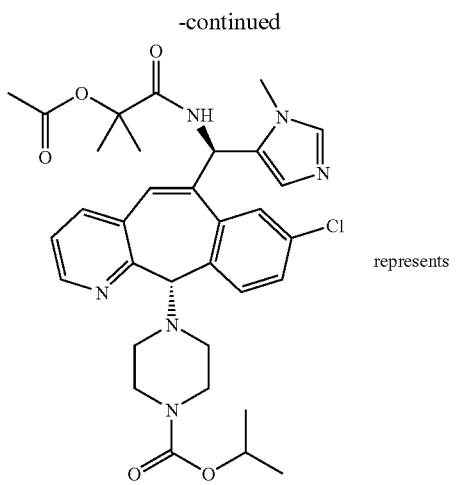
represents
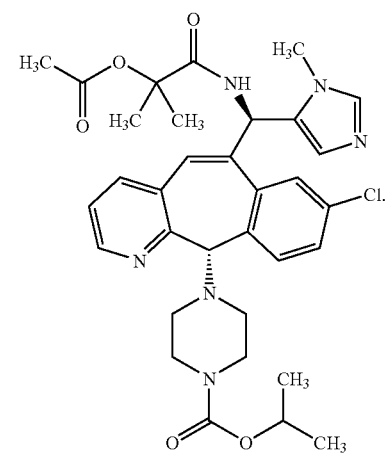
Those skilled in the art will appreciate that the formula:
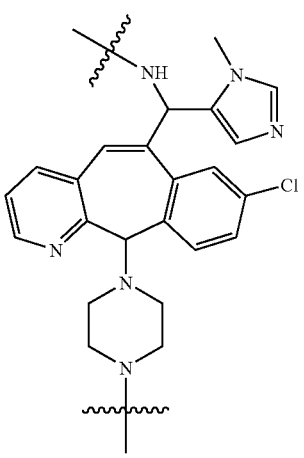

can represent one or more isomers selected from the group consisting of:
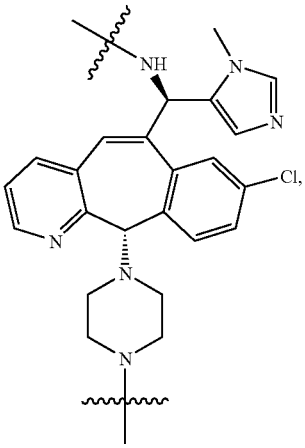
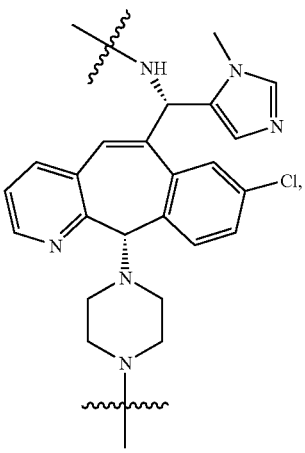
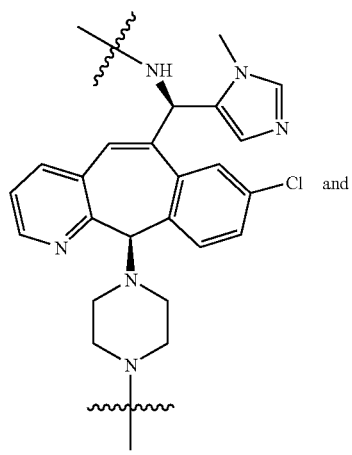
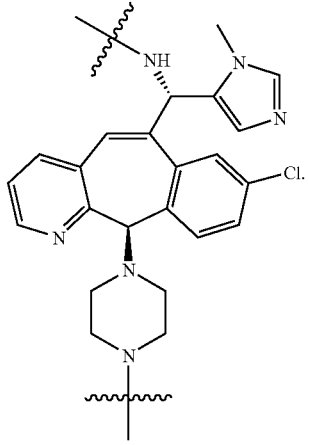
The preferred isomer is:
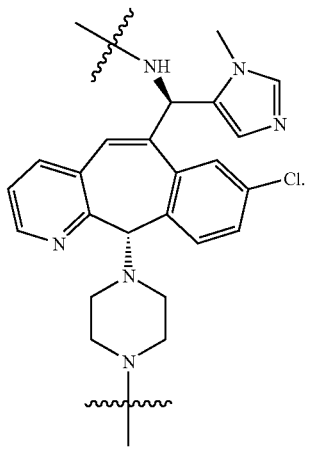
Thus, one embodiment of this invention is directed to compounds (FPT inhibitors) of formula I:
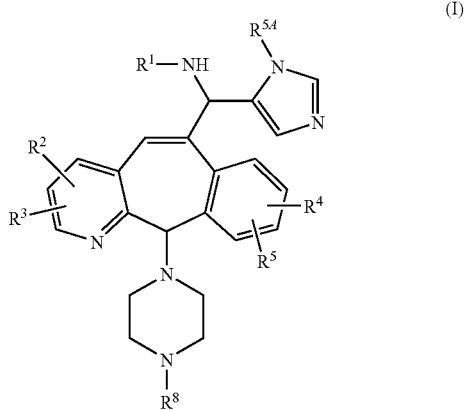

and the pharmaceutically acceptable salts or solvates thereof, wherein:

$R^1$ is selected from the group consisting of:

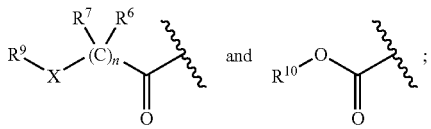

n is 1 to 6;

X is selected from the group consisting of O, S, and N;

$R^2$, $R^3$, $R^4$, and $R^5$ are independently selected from the group consisting of: H, Br, Cl, and F;

$R^{5A}$ is selected from the group consisting of a H, $C_1$ to $C_6$ alkyl group, and a $C_3$ to $C_6$ cycloalkyl group;

$R^6$ and $R^7$, for each n, are independently selected from the group consisting of: (1) H, (2) $C_1$ to $C_4$ alkyl, and (3) a $C_3$ to $C_7$ cycloalkyl ring formed by taking $R^6$ and $R^7$ together with the carbon atom to which they are bonded to;

$R^8$ is selected from the group consisting of:

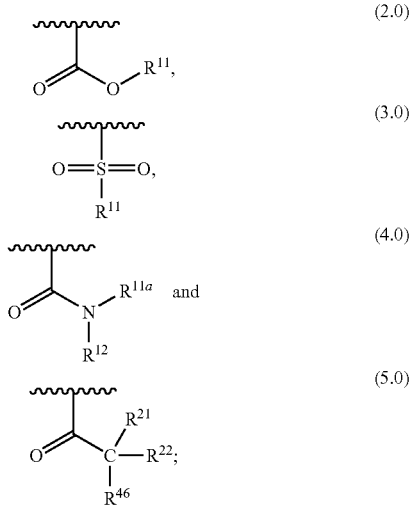

$R^9$ is selected from the group consisting of: $C_1$ to $C_6$ alkyl group, aryl, heteroaryl, cycloalkyl, heterocycloalkyl, cycloalkylalkyl, heterocycloalkylalkyl, alkenyl, alkynyl, arylalkyl, arylheteroalkyl, cycloalkenyl, heteroalkenyl, heteroalkyl, and heteroalkynyl; or $R^9$ is selected from the group consisting of: $C_1$ to $C_6$ alkyl group, aryl, heteroaryl, cycloalkyl, heterocycloalkyl, cycloalkylalkyl, heterocycloalkylalkyl, alkenyl, alkynyl, arylalkyl, arylheteroalkyl, cycloalkenyl, heteroalkenyl, heteroalkyl, and heteroalkynyl; wherein (1) said $R^9$ aryl, heteroaryl, cycloalkyl, heterocycloalkyl, cycloalkylalkyl, heterocycloalkylalkyl, alkenyl, alkynyl, arylalkyl, arylheteroalkyl, cycloalkenyl, heteroalkenyl, heteroalkyl, and heteroalkynyl groups are substituted with 1 to 3 substituents independently selected from the group consisting of: —OH, halo (e.g., Br, F, or Cl), alkyl (e.g., $C_1$ to $C_6$ alkyl), cycloalkyl (e.g., $C_3$ to $C_6$, for example cyclopropyl), —$NH_2$, —$NH(C_1$ to $C_6$ alkyl) (e.g., —$NHCH_3$), —$N(C_1$ to $C_6$ alkyl)$_2$ wherein each alkyl group is independently selected (e.g. —$N(CH_3)_2$), alkoxy (e.g., methoxy), and —$CO_2R^{14}$ wherein $R^{14}$ is selected from the group consisting of: H and alkyl (e.g., $C_1$ to $C_6$ alkyl, for example methyl and ethyl), provided that the carbon atom, by which said $R^9$ group is bonded to the X substituent, is not substituted with a —OH, —$NH_2$, —$NH(C_1$ to $C_6$ alkyl) or —$N(C_1$ to $C_6$ alkyl)$_2$ group; and (2) said $R^9$ $C_1$ to $C_6$ alkyl group is substituted with 1 to 3 substituents independently selected from the group consisting of: —OH, halo (e.g., Br, F, or Cl), cycloalkyl (e.g., $C_3$ to $C_6$, for example cyclopropyl), —$NH_2$, —$NH(C_1$ to $C_6$ alkyl) (e.g., —$NHCH_3$), —$N(C_1$ to $C_6$ alkyl)$_2$ wherein each alkyl group is independently selected (e.g. —$N(CH_3)_2$), alkoxy (e.g., methoxy), and —$CO_2R^{14}$ wherein $R^{14}$ is selected from the group consisting of: H and alkyl (e.g., $C_1$ to $C_6$ alkyl, for example methyl and ethyl); provided that the carbon atom, by which said $R^9$ group is bonded to the X substituent, is not substituted with a —OH, —$NH_2$, —$NH(C_1$ to $C_6$ alkyl) or —$N(C_1$ to $C_6$ alkyl)$_2$ group;

$R^{9a}$ is selected from the group consisting of: alky and arylalkyl;

$R^{10}$ is selected from the group consisting of: aryl, heteroaryl, cycloalkyl, heterocycloalkyl, cycloalkylalkyl, heterocycloalkylalkyl, alkenyl, alkynyl, arylheteroalkyl, cycloalkenyl, heteroalkenyl, heteroalkyl, and heteroalkynyl; or $R^{10}$ is selected from the group consisting of: aryl, heteroaryl, cycloalkyl, heterocycloalkyl, cycloalkylalkyl, heterocycloalkylalkyl, alkenyl, alkynyl, arylheteroalkyl, cycloalkenyl, heteroalkenyl, heteroalkyl, and heteroalkynyl; wherein said $R^{10}$ groups are substituted with 1 to 3 substituents independently selected from the group consisting of: —OH, halo (e.g., Br, F, or Cl), alkyl (e.g., $C_1$ to $C_6$ alkyl), cycloalkyl (e.g., $C_3$ to $C_6$, for example cyclopropyl), —$NH_2$, —$NH(C_1$ to $C_6$ alkyl) (e.g., —$NHCH_3$), —$N(C_1$ to $C_6$ alkyl)$_2$ wherein each alkyl group is independently selected (e.g. —$N(CH_3)_2$), alkoxy (e.g., methoxy), and —$CO_2R^{14}$ wherein $R^{14}$ is selected from the group consisting of: H and alkyl (e.g., $C_1$ to $C_6$ alkyl, for example methyl and ethyl);

$R^{11}$ is selected from the group consisting of: (1) alkyl (2) substituted alkyl, (3) unsubstituted aryl, (4) substituted aryl, (5) unsubstituted cycloalkyl, (6) substituted cycloalkyl, (7) unsubstituted heteroaryl, (8) substituted heteroaryl, (9) hetero-cycloalkyl, and (10) substituted heterocycloalkyl; wherein said substituted alkyl, substituted cycloalkyl, and substituted heterocycloalkyl $R^{11}$ groups are substituted with one or more (e.g. 1, 2 or 3) substituents independently selected from the group consisting of: (1) —OH, provided that when there is more than one —OH group then each —OH group is bound to a different carbon atom (i.e., only one —OH group can be bound to a carbon atom), (2) fluoro, and (3) alkyl; and wherein said substituted aryl and substituted heteroaryl $R^{11}$ groups are substituted with one or more (e.g. 1, 2 or 3) substituents independently selected from the group consisting of: (1) —OH, provided that when there is more than one —OH group then each —OH group is bound to a different carbon atom (i.e., only one —OH group can be bound to a carbon atom), (2) halogen (e.g. Br, Cl or F), and (3) alkyl;

$R^{11a}$ is selected from the group consisting of: (1) H, (2) OH, (3) alkyl, (4) substituted alkyl, (5) aryl, (6) substituted aryl, (7) unsubstituted cycloalkyl, (8) substituted cycloalkyl, (9) unsubstituted heteroaryl, (10) substituted heteroaryl, (11) heterocycloalkyl, (12) substituted heterocycloalkyl, and (13) —$OR^{9a}$; wherein said substituted alkyl, substituted cycloalkyl, and substituted heterocycloalkyl $R^{11a}$ groups are substituted with one or more (e.g. 1, 2 or 3) substituents independently selected from the group consisting of: (1) —OH, provided that when there is more than one —OH group then each —OH group is bound to a different carbon atom (i.e., only one —OH group can be bound to a carbon atom), (2) —CN, (3) —$CF_3$, (4) fluoro, (5) alkyl, (6)

cycloalkyl, (7) heterocycloalkyl, (8) arylalkyl, (9) heteroarylalkyl, (10) alkenyl and (11) heteroalkenyl; and wherein said substituted aryl and substituted heteroaryl $R^{11a}$ groups have one or more (e.g. 1, 2 or 3) substituents independently selected from the group consisting of: (1) —OH, provided that when there is more than one —OH group then each —OH group is bound to a different carbon atom (i.e., only one —OH group can be bound to a carbon atom), (2) —CN, (3) —CF$_3$, (4) halogen (e.g Br, Cl or F), (5) alkyl, (6) cycloalkyl, (7) heterocycloalkyl, (8) arylalkyl, (9) heteroarylalkyl, (10) alkenyl, and (11) heteroalkenyl;

$R^{12}$ is selected from the group consisting of: H, alkyl, piperidine Ring V, cycloalkyl, and -alkyl-(piperidine Ring V), wherein piperidine Ring V is

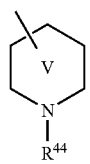

wherein $R^{44}$ is defined below;

$R^{21}$, $R^{22}$ and $R^{46}$ are independently selected from the group consisting of: (1)-H, (2) alkyl (e.g., methyl, ethyl, propyl, butyl or t-butyl), (3) unsubstituted aryl, (e.g. phenyl), (4) substituted aryl substituted with one or more substituents independently selected from the group consisting of: alkyl, halogen, CF$_3$ and OH, (5) unsubstituted cycloalkyl, (e.g. cyclohexyl), (6) substituted cycloalkyl substituted with one or more substituents independently selected from the group consisting of: alkyl, halogen, CF$_3$ and OH, (7) heteroaryl of the formula

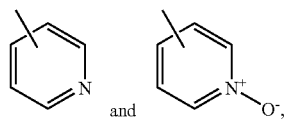

(8) heterocycloalkyl of the formula:

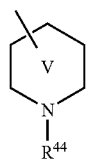

(i.e., piperidine Ring V) wherein $R^{44}$ is selected from the group consisting of: (a) —H, (b) alkyl (e.g., methyl, ethyl, propyl, butyl or t-butyl), (c) alkylcarbonyl (e.g., CH$_3$C(O)—), (d) alkyloxycarbonyl (e.g., —C(O)O-t-C$_4$H$_9$, —C(O)OC$_2$H$_5$ and —C(O)OCH$_3$), (e) haloalkyl (e.g., trifluoromethyl), and (f) —C(O)NH(R$^{51}$), (9) —NH$_2$ provided that only one of $R^{21}$, $R^{22}$, and $R^{46}$ group can be —NH$_2$ and provided that when one of $R^2$, $R^{22}$, and $R^{41}$ is —NH$_2$ then the remaining groups are not —OH, (10) —OH provided that only one of $R^2$, $R^{22}$, and $R^{46}$ group can be —OH and provided that when one of $R^{21}$, $R^{22}$, and $R^{46}$ is —OH then the remaining groups are not —NH$_2$, and (11) alkyl substituted with one or more substituents (e.g., 1-3, or 1-2, and preferably 1) selected from the group consisting of: —OH and —NH$_2$ and provided that there is only one —OH or one —NH$_2$ group on a substituted carbon, or $R^{21}$ and $R^{22}$ taken together with the carbon to which they are bound form a cyclic ring selected from the group consisting of: (1) unsubstituted cycloalkyl (e.g., cyclopropyl, cyclobutyl, cyclopentyl, and cyclohexyl), (2) cycloalkyl substituted with one or more substituents independently selected from the group consisting of: alkyl, halogen, CF$_3$ and OH, (3) unsubstituted cycloalkenyl

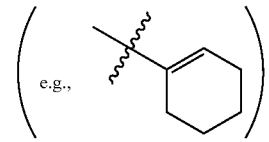

(4) cycloalkenyl substituted with one or more substituents independently selected from the group consisting of: alkyl, halogen, CF$_3$ and OH, (5) heterocycloalkyl, e.g., a piperidyl ring of the formula:

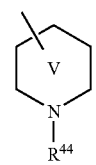

wherein $R^{44}$ is selected from the group consisting of: (a) —H, (b) alkyl (e.g., methyl, ethyl, propyl, butyl or t-butyl), (c) alkylcarbonyl (e.g., CH$_3$C(O)—), (d) alkyloxy carbonyl (e.g., —C(O)O-t-C$_4$H$_9$, —C(O)OC$_2$H$_5$, and —C(O)OCH$_3$), (e) haloalkyl (e.g., trifluoromethyl), and (f)-C(O)NH(R$^{51}$), (6) unsubstituted aryl (e.g., phenyl), (7) aryl substituted with one or more substituents independently selected from the group consisting of: alkyl (e.g., methyl), halogen (e.g., Cl, Br and F), —CN, —CF$_3$, OH and alkoxy (e.g., methoxy), and (8) heteroaryl selected from the group consisting of:

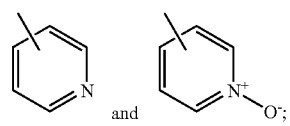

and $R^{51}$ is selected from the group consisting of: H and alkyl (e.g., methyl, ethyl, propyl, butyl and t-butyl).

For the compounds of formula I, $R^2$, $R^3$, $R^4$, and $R^5$ are preferably independently selected to form an unsubstituted (i.e., $R^2$ to $R^5$ are H), or a monohalo, dihalo, or trihalo substituted ring system, wherein halo is selected from the group consisting of: Br, Cl and F. Examples of such halo substitutions are: 8-halo (e.g., 8-Cl), 3,8-dihalo (e.g., 3-Br-8-Cl), 3,7,8-trihalo (e.g., 3-Br-7-Br-8-Cl) and 3,8,10-trihalo (e.g., 3-Br-8-Cl-10-Br). A mono halo substituted ring system is preferred, with 8-halo being more preferred, and 8-Cl being most preferred.

Thus, the compound of formula I is preferably a compound of formula II:
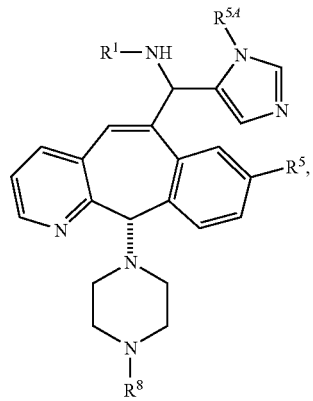
(II)
and most preferably a compound of formula III:
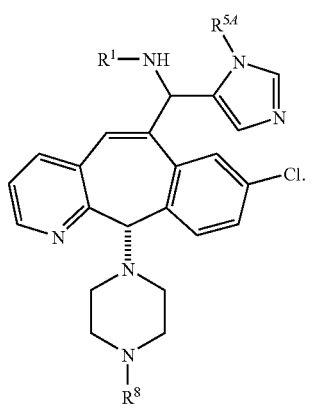
(III)
The compound of formula I is more preferably a compound of formula IIA
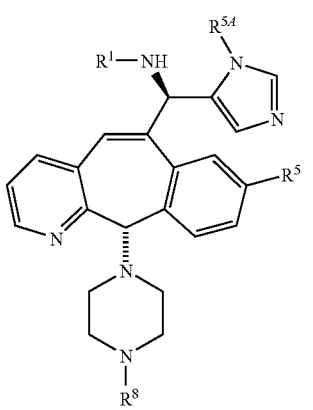
(IIA)
and even more preferably a compound of formula IIIA
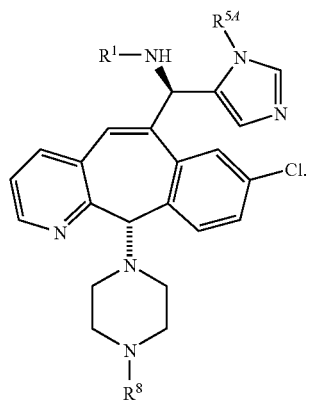
(IIIA)
Compounds of formula I include compounds of formula IV:
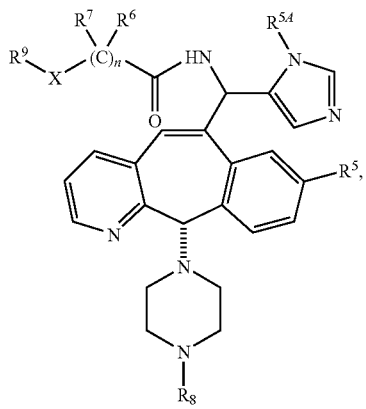
(IV)
and preferably a compound of formula V:
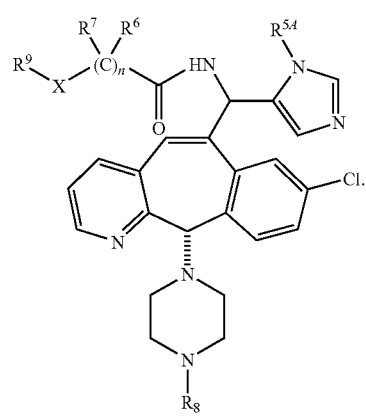
(V)

Compounds of formula I include compounds of formula IVA

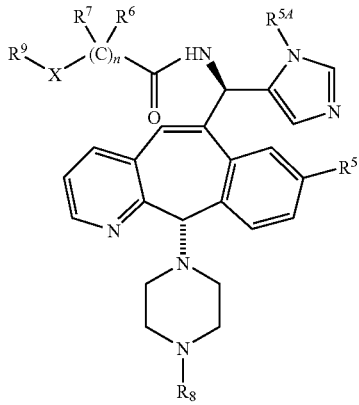

(IVA)

and preferably compounds of formula VA:

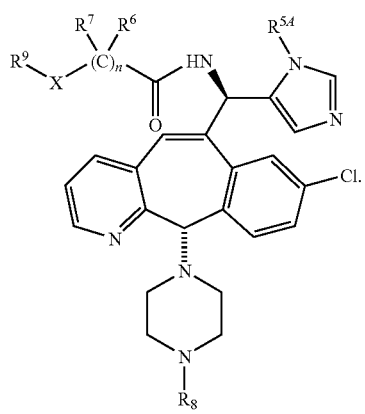

(VA)

Compounds of formula I also include compounds of formula VI:

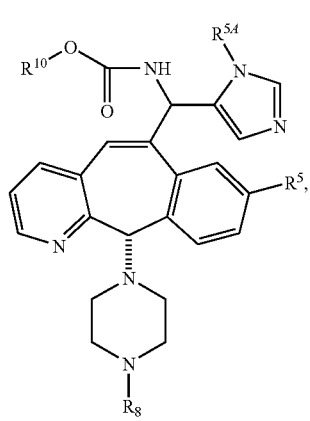

(VI)

and preferably compounds of formula VII:

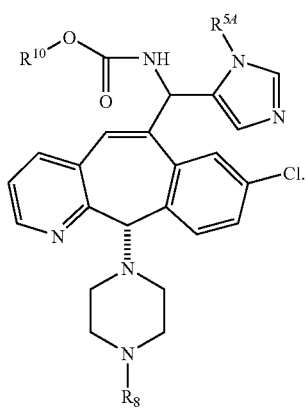

(VII)

Compounds of formula I also include compounds of formula VIA:

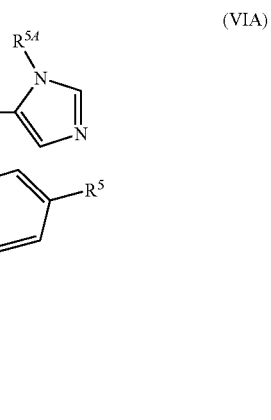

(VIA)

and preferably compounds of formula VIIA:

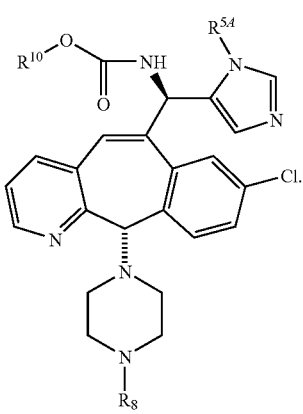

(VIIA)

For compounds of formula I, examples of $R^{5A}$ include, but are not limited to: H, methyl, ethyl, isopropyl and cyclopropyl.

For compounds of formula I, $R^{5A}$ is preferably $C_1$ to $C_6$ alkyl, with methyl being most preferred.

For compounds of formula I, X is preferably O.

For compounds of formula I, n is preferably 1.

For compounds of formula I, $R^6$ and $R^7$ are preferably independently selected from the group consisting of H, methyl and the cyclopropyl ring formed when $R^6$ and $R^7$ are taken together with the carbon atom to which they are bonded to. More preferably $R^6$ and $R^7$ are independently selected from the group consisting of H and methyl. Most preferably $R^6$ and $R^7$ are H.

For compounds of formula I, $R^9$ is preferably $C_1$ to $C_6$ alkyl, and more preferably methyl.

For compounds of formula I, $R^{10}$ is preferably selected from the group consisting of: cycloalkyl and cycloalkyl substituted with a $C_1$ to $C_6$ alkyl group, more preferably selected from the group consisting of cycloalkyl and cycloalkyl substituted with methyl, most preferably selected from the group consisting of: cyclopropyl and cyclopropyl substituted with a methyl group, and even more preferably $R^{10}$ is:

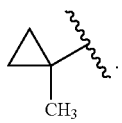

For compounds of formula I, when $R^1$ is

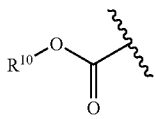

then $R^8$ is preferably

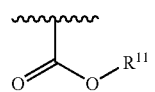

wherein the $R^{11}$ substituent is the same as the $R^{10}$ substituent. For example, when $R^1$ is:

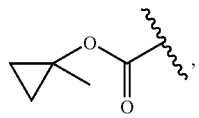

then $R^8$ is preferably

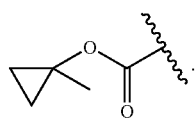

For compounds of formula I, $R^8$ is preferably

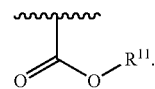

For compounds of formula I, $R^8$ is more preferably

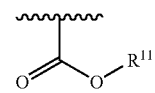

wherein $R^{11}$ is selected from the group consisting of: alkyl, unsubstituted cycloalkyl and substituted cycloalkyl. Most preferably, $R^{11}$ is selected from the group consisting of: alky and substituted cycloalkyl. Even more preferably, $R^{11}$ is selected from the group consisting of: isopropyl, and cyclopropyl substituted with methyl, i.e., the group

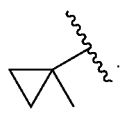

For compounds of formula I, wherein $R^1$ is

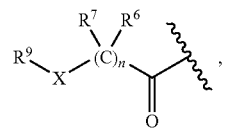

X is O, n is 1, $R^6$ and $R^7$ are independently selected from the group consisting of H, methyl and the cyclopropyl ring formed when $R^6$ and $R^7$ are taken together with the carbon atom to which they are bonded to (wherein preferably $R^6$ and $R^7$ are independently selected from the group consisting of H and methyl, and more preferably $R^6$ and $R^7$ are H), and $R^9$ is $C_1$ to $C_6$ alkyl (preferably methyl), $R^8$ is preferably

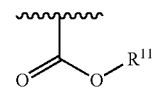

wherein $R^{11}$ is preferably alkyl (more preferably isopropyl).

For compounds of formula I, wherein $R^1$ is

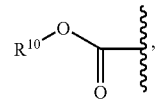

$R^{10}$ is selected from the group consisting of: cycloalkyl and cycloalkyl substituted with a $C_1$ to $C_6$ alkyl group (preferably $R^{10}$ selected from the group consisting of cycloalkyl and cycloalkyl substituted with methyl, and more preferably selected from the group consisting of: cyclopropyl and cyclopropyl substituted with a methyl group, and most preferably $R^{10}$ is:

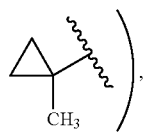

$R^8$ is preferably

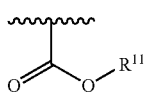

wherein $R^{11}$ is selected from the group consisting of: unsubstituted cycloalkyl and substituted cycloalkyl (preferably, $R^{11}$ is substituted cycloalkyl, and more preferably, $R^{11}$ is cyclopropyl substituted with methyl, i.e., the group

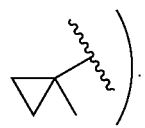

The compounds of formulas 100 to 174 are:

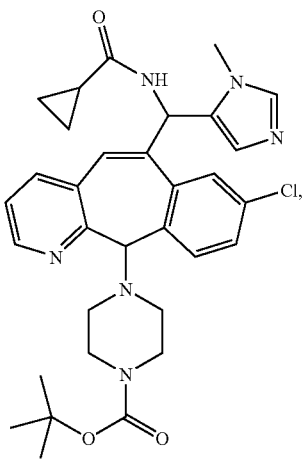

100

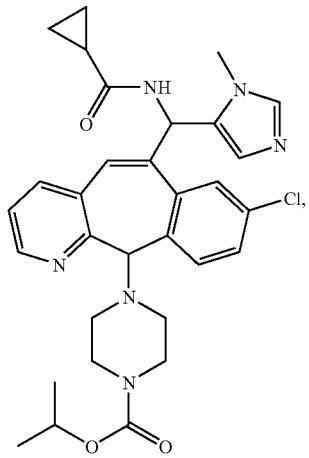

101

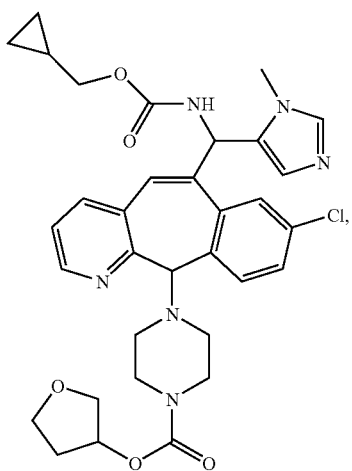

102

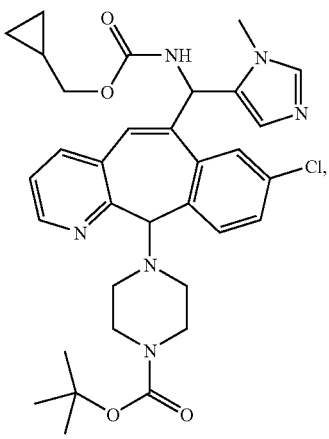

103

-continued
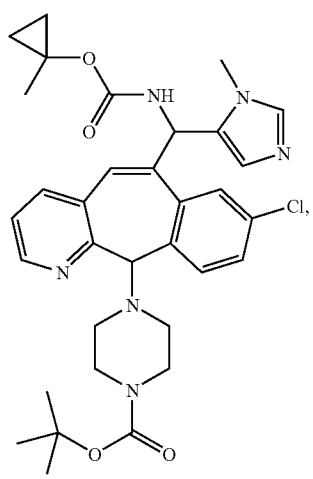
104
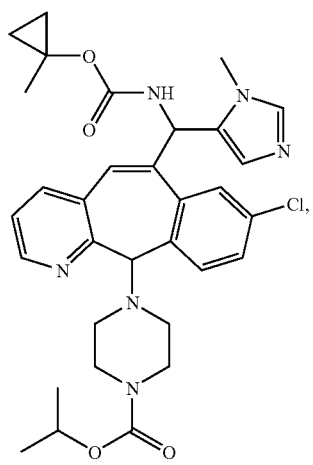
105
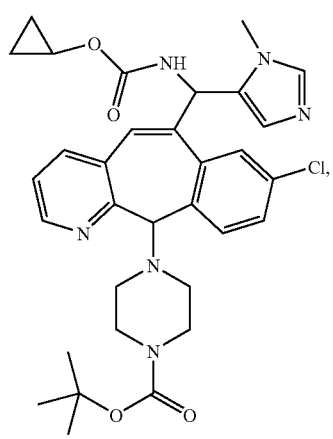
106
-continued
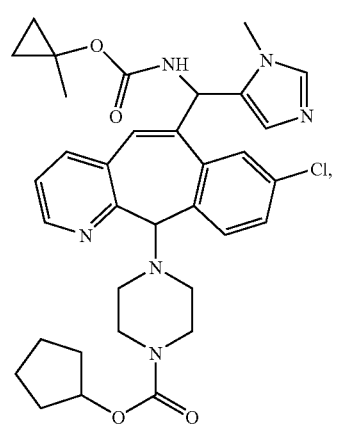
107
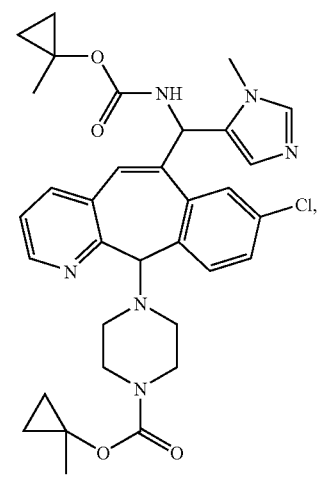
108
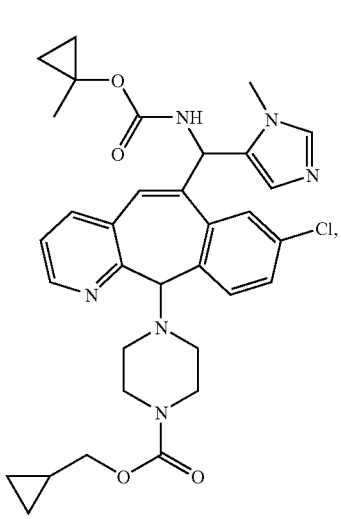
109

110
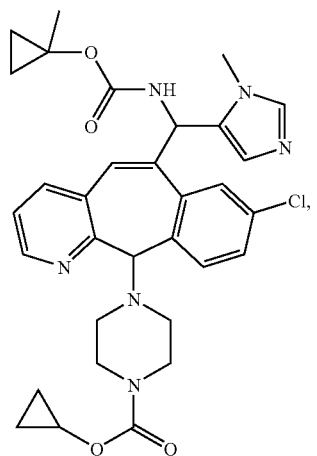
111
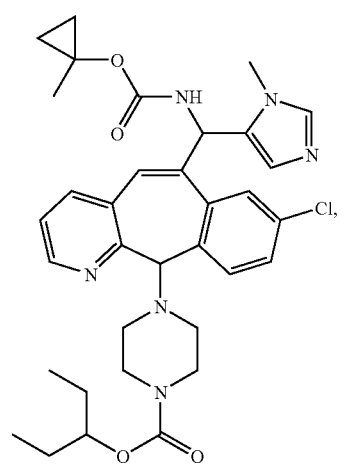
112
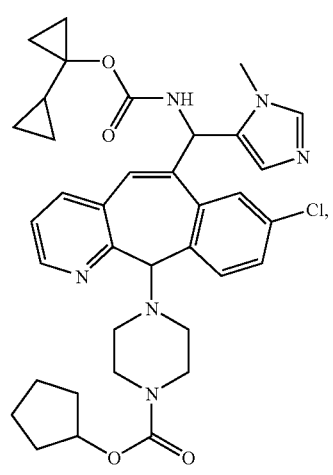
113
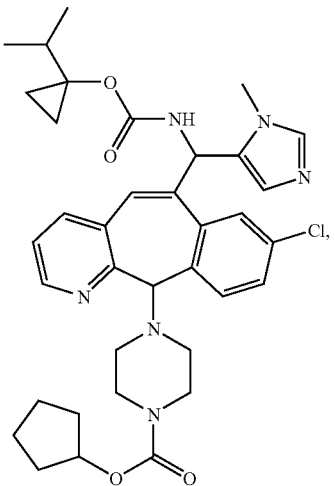
114
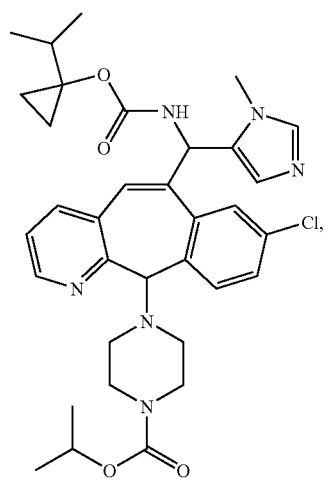
115
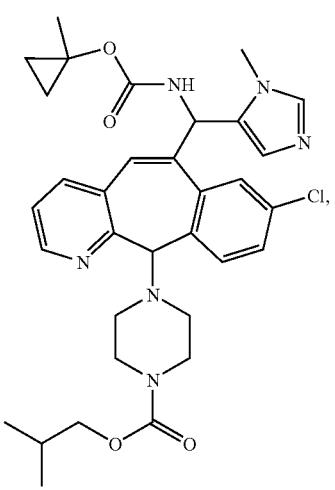

-continued
116
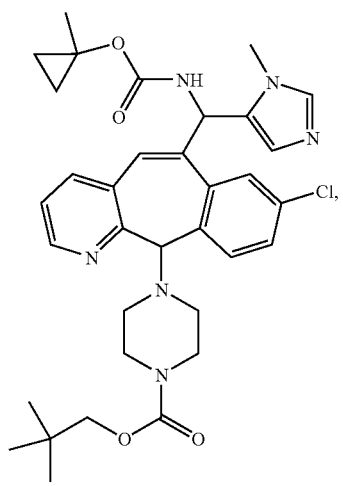
117
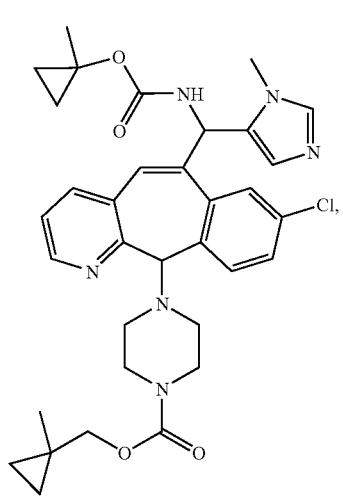
118
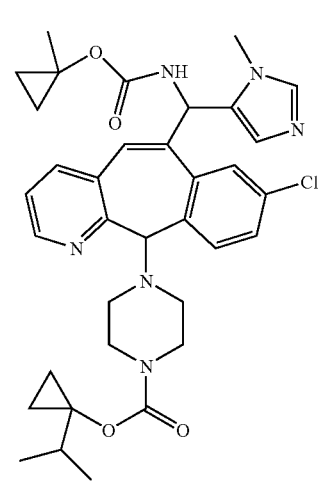
-continued
119
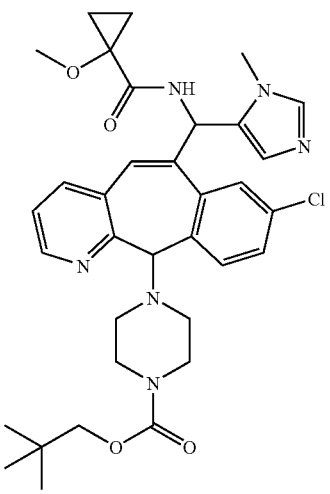
120
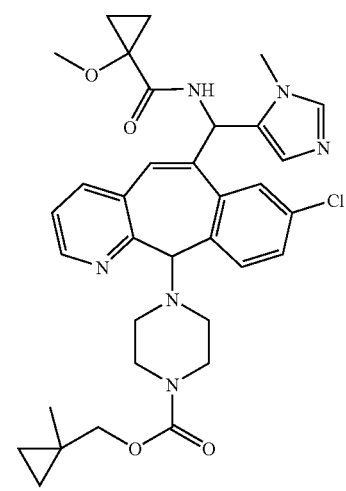
121
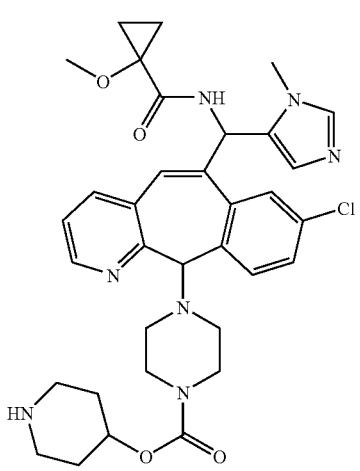

-continued
31
122
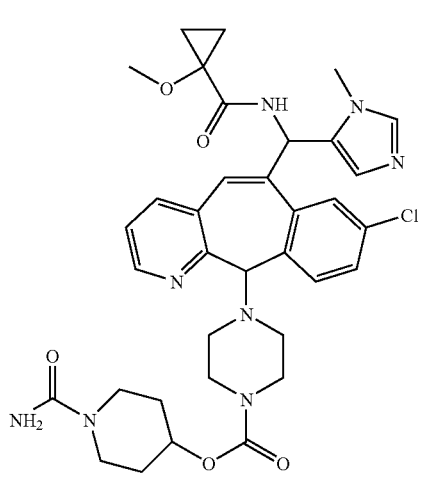
123
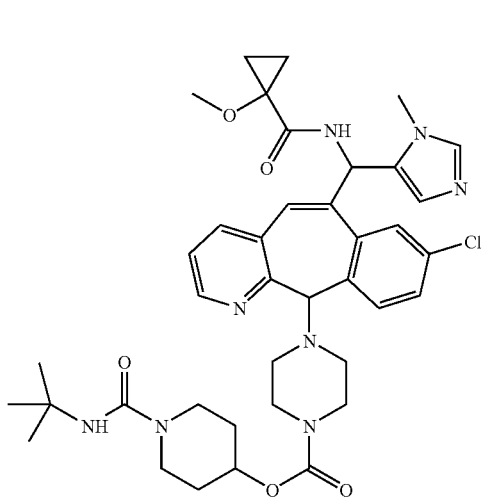
124
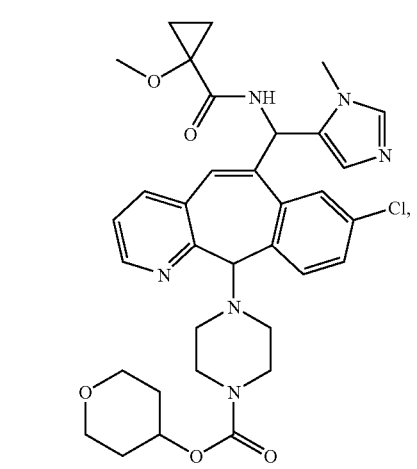
32
-continued
125
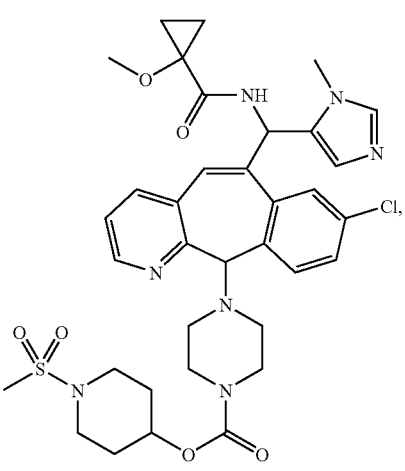
126
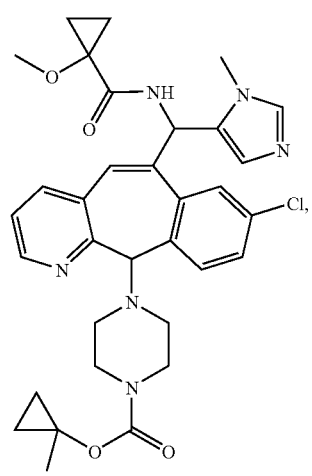
127
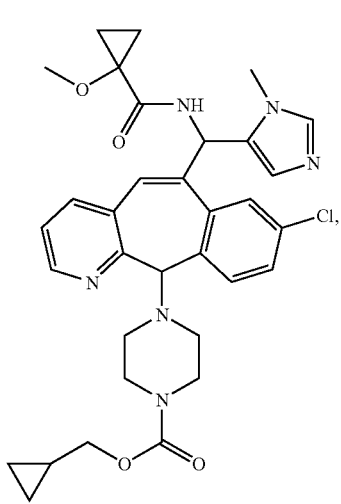

-continued
128
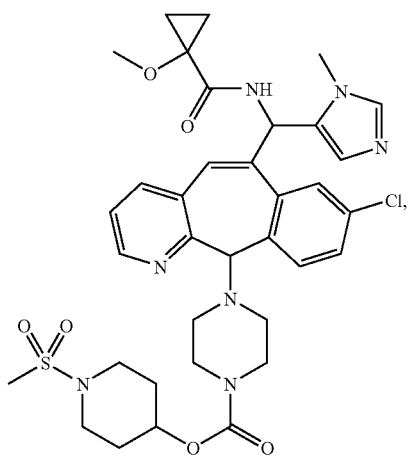
129
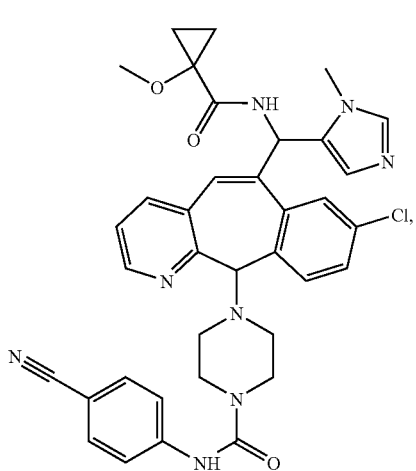
130
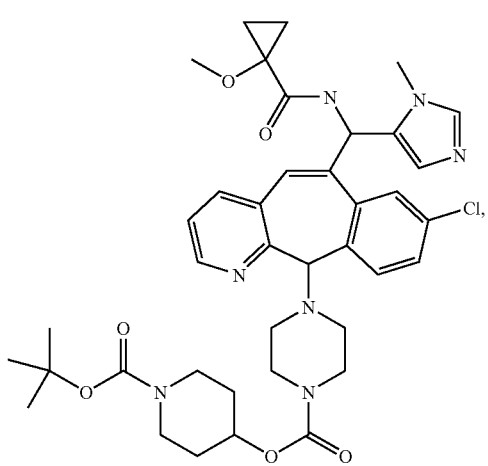
-continued
131
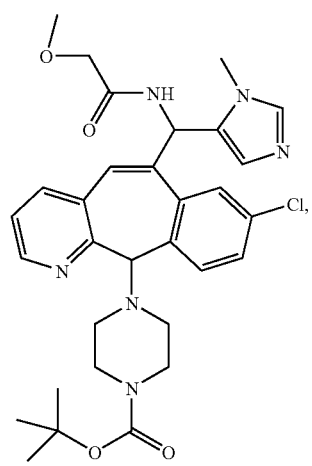
132
133
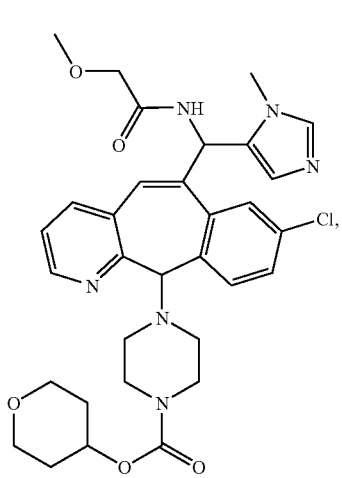

134
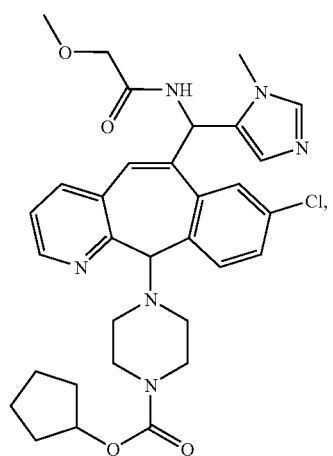
137
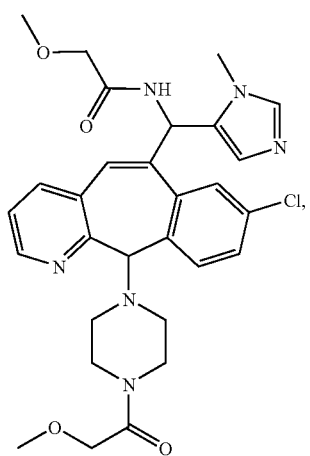
135
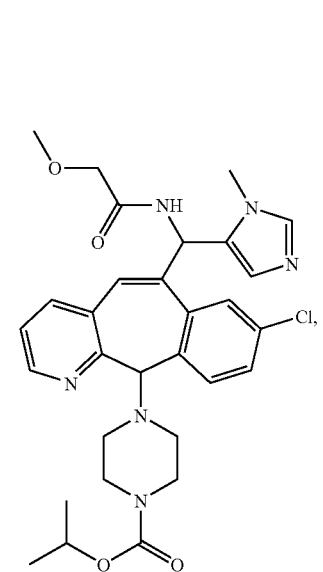
138
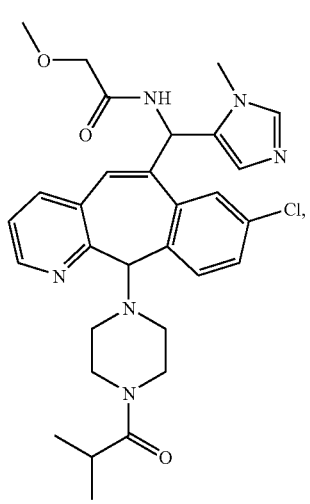
136
139
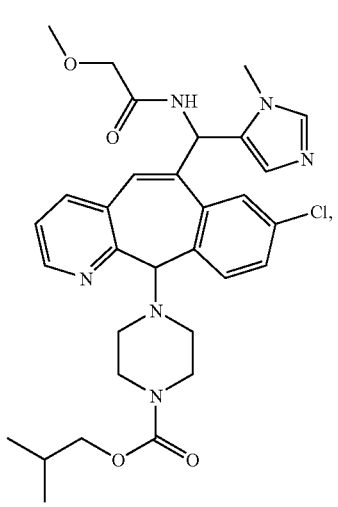

-continued
140
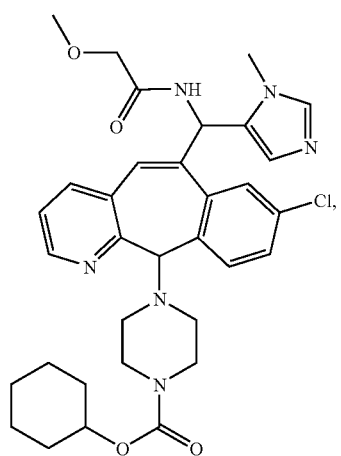
141
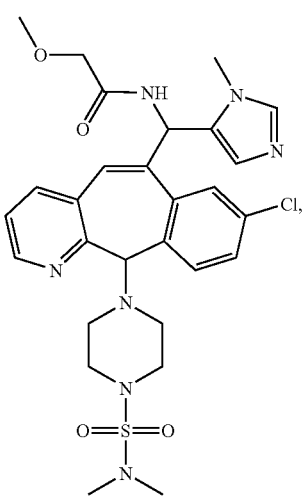
142
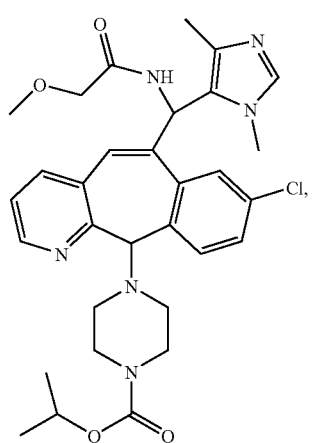
-continued
143
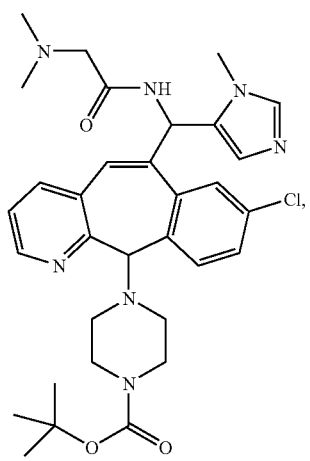
144
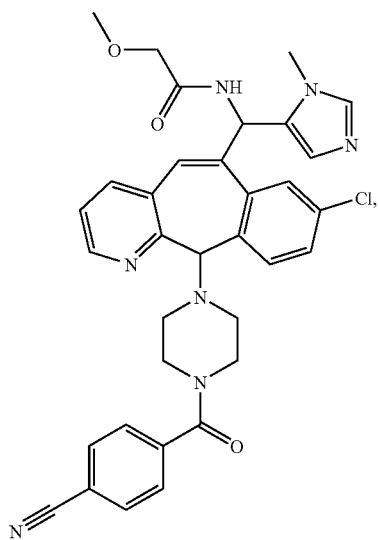
145
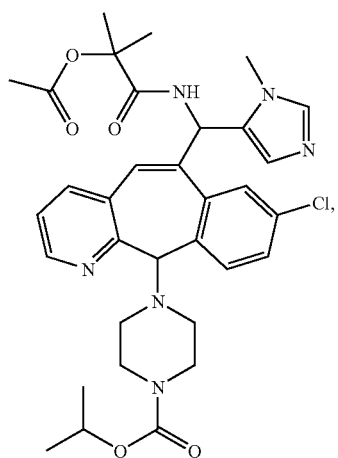

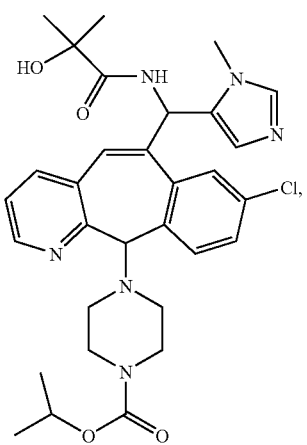
146
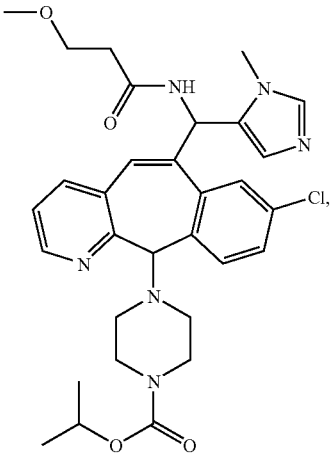
149
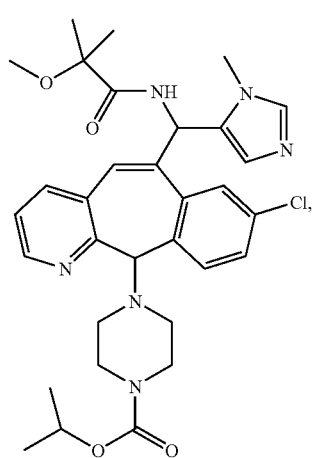
147
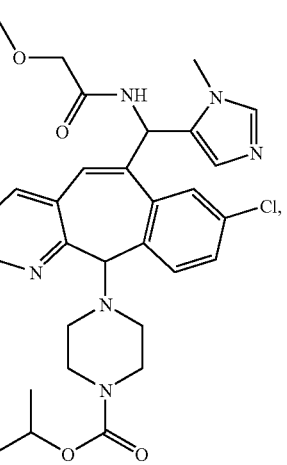
150
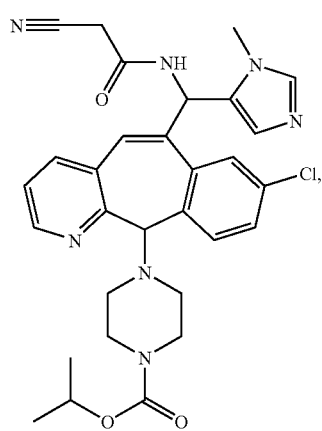
148
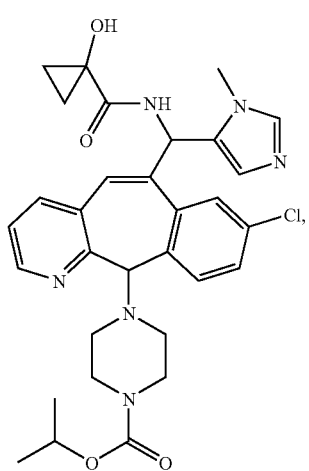
151

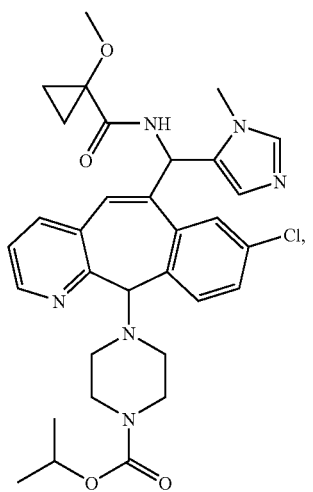
152
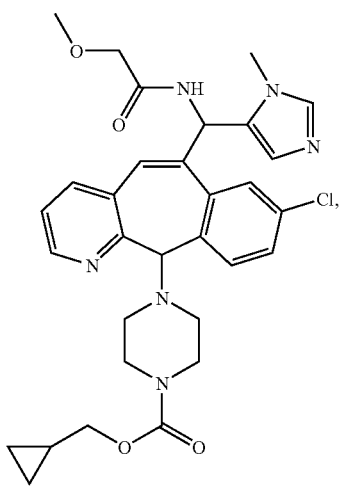
155
153
156
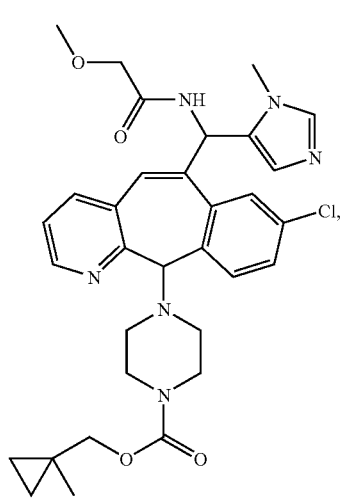
154
157

158
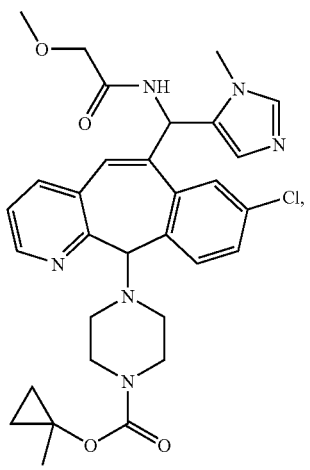
159
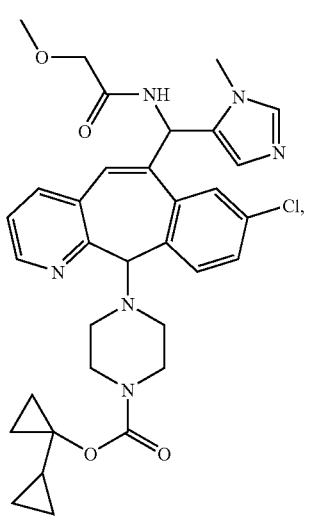
161
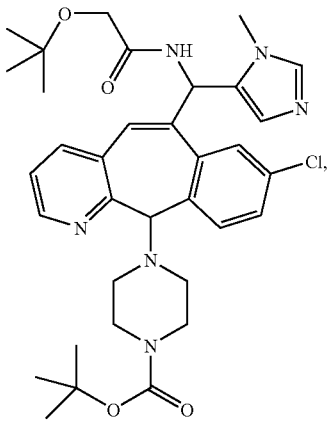
162
160
163
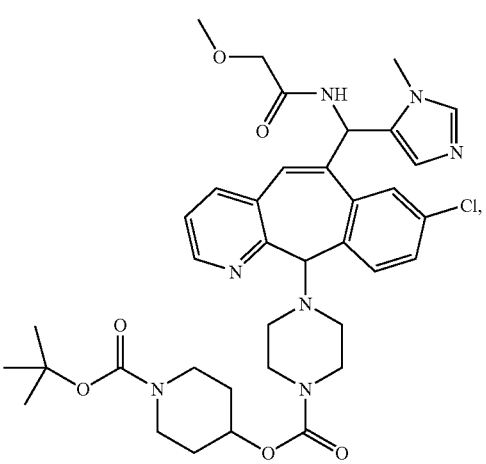

-continued
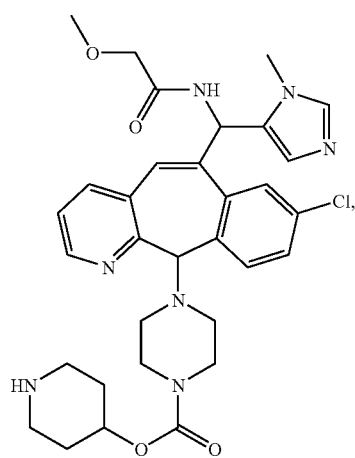
164
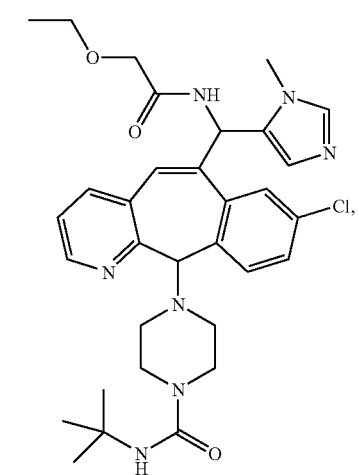
165
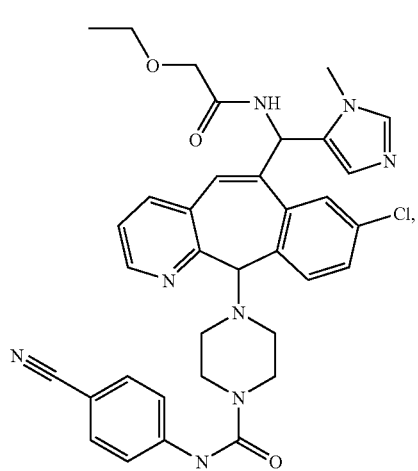
166
-continued
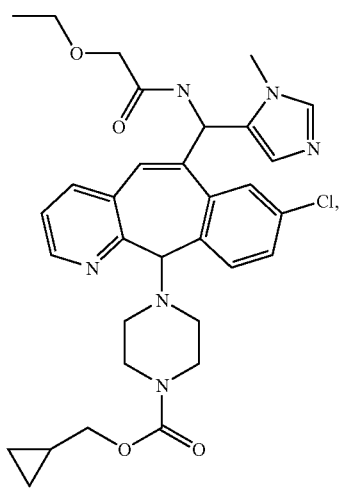
167
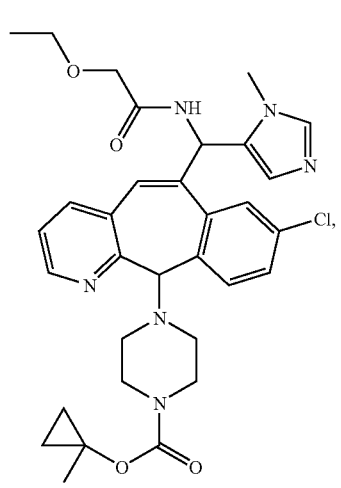
168
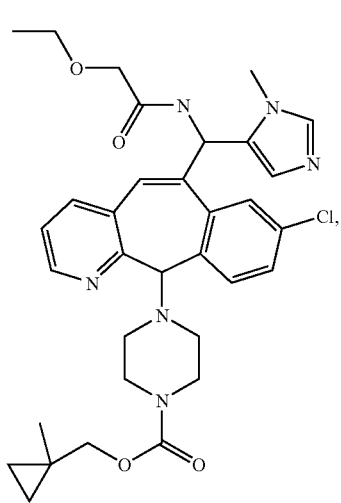
169

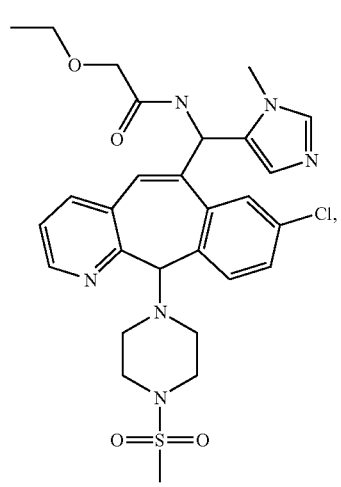
170
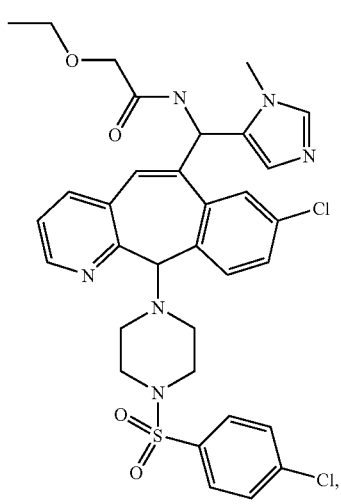
171
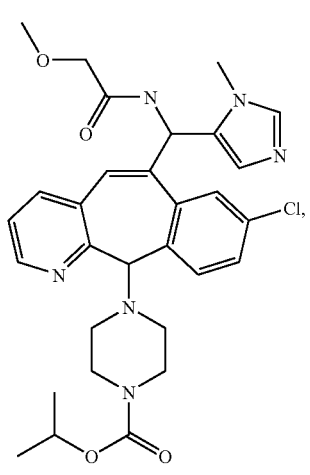
172
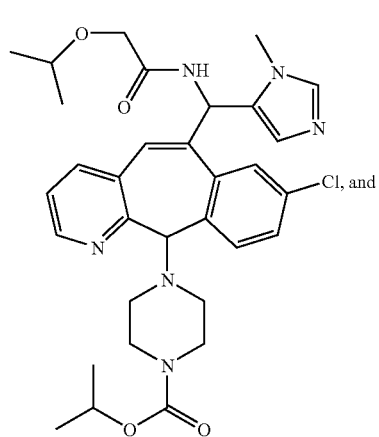
173
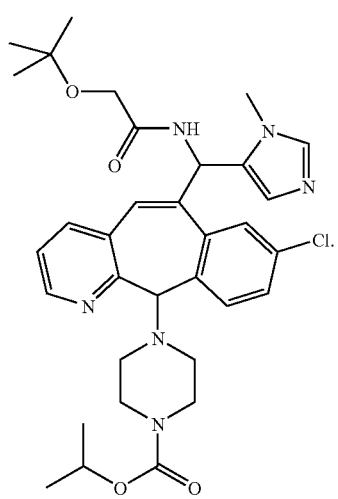
174
Representative compounds of compounds 100 to 174 include, but are not limited to:
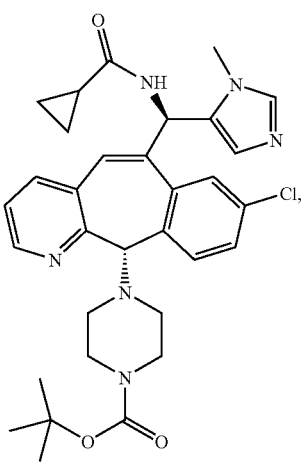
100.1

-continued
101.1
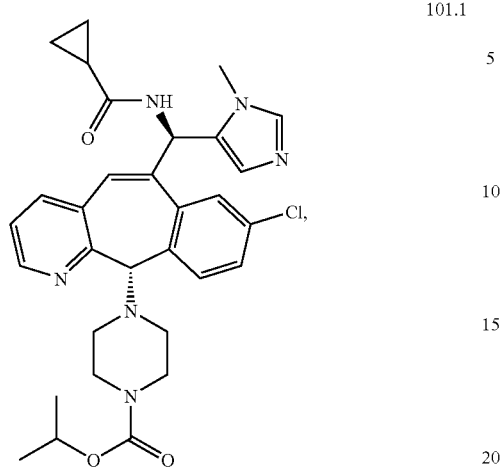
102.1
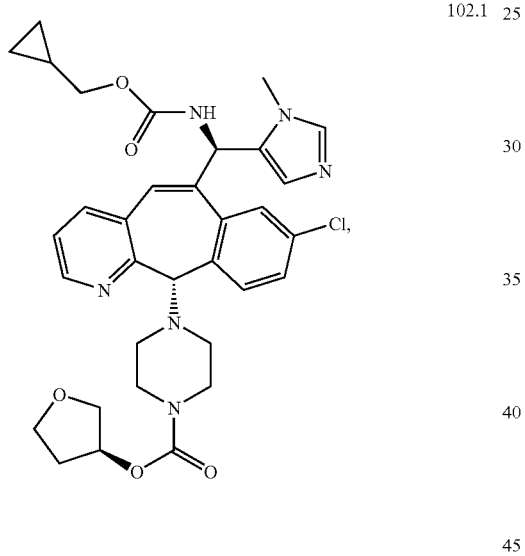
102.2
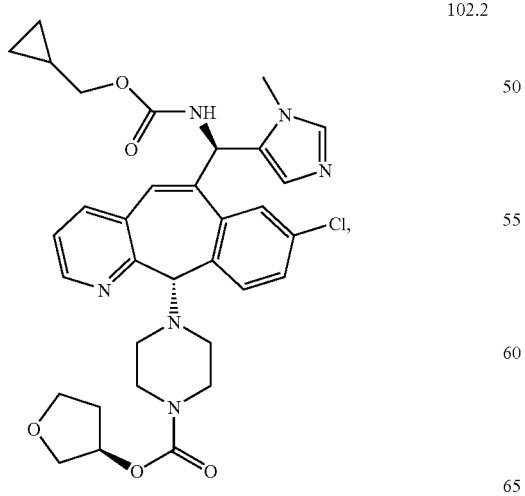
-continued
103.1
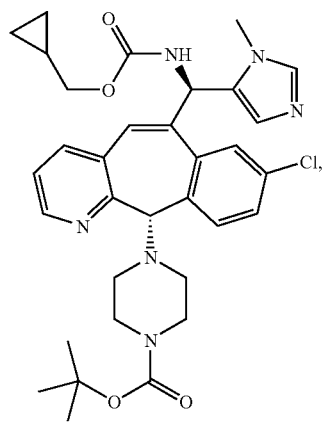
104.1
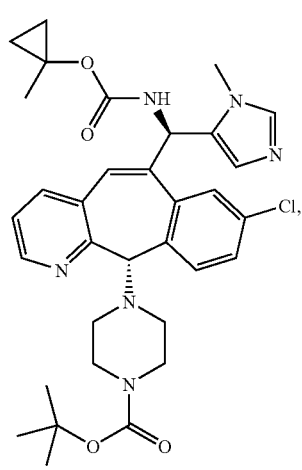
105.1
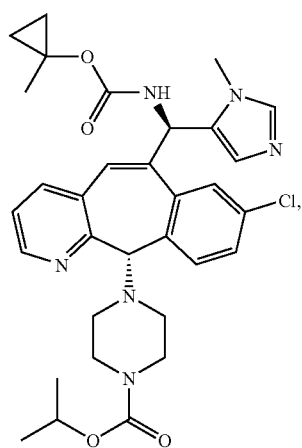

-continued
106.1
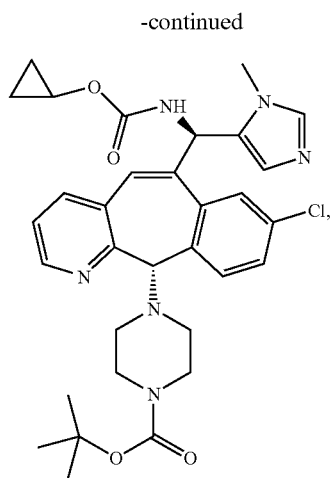
107.1
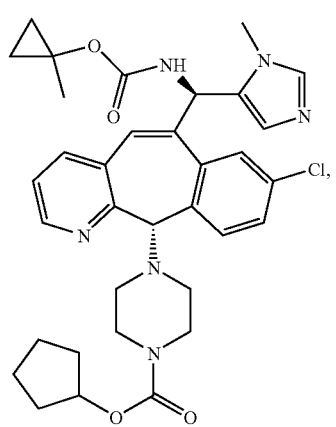
108.1
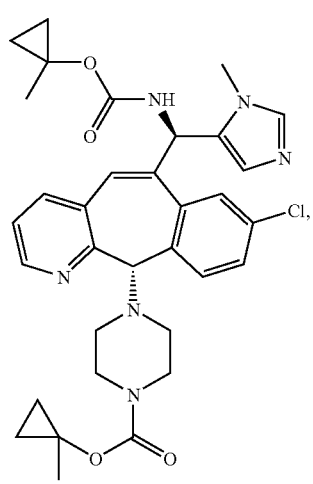
-continued
109.1
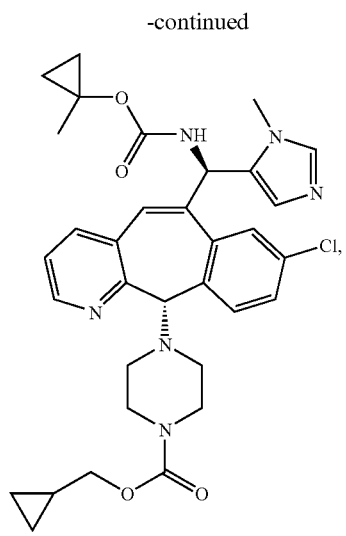
110.1
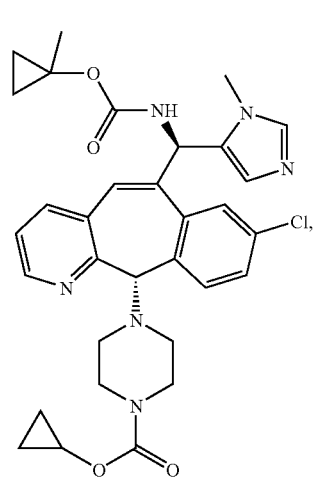
111.1
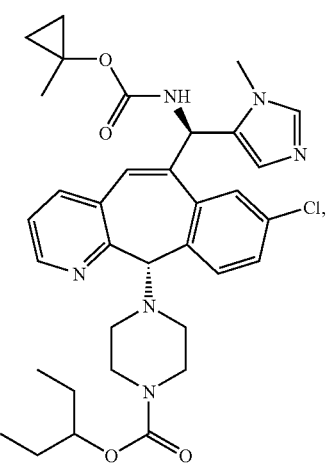

| | |
|---|---|
| 112.1 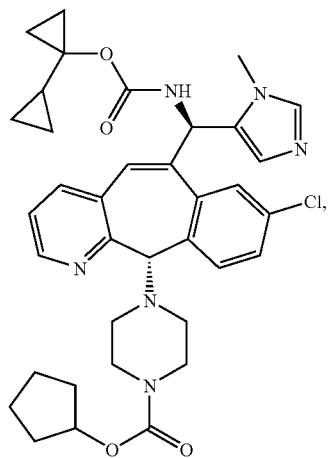 | 115.1 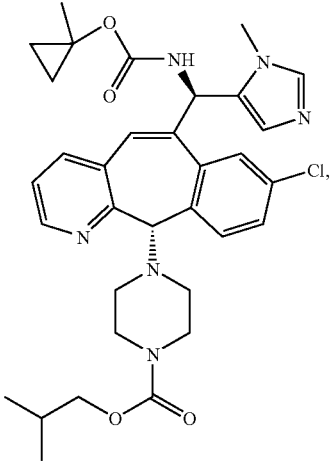 |
| 113.1 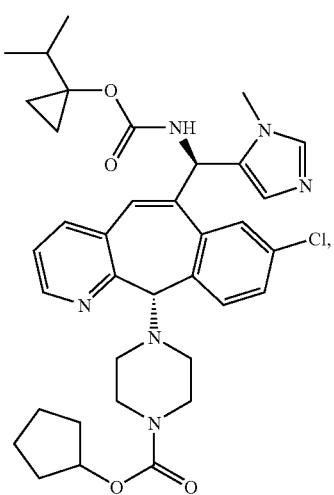 | 116.1 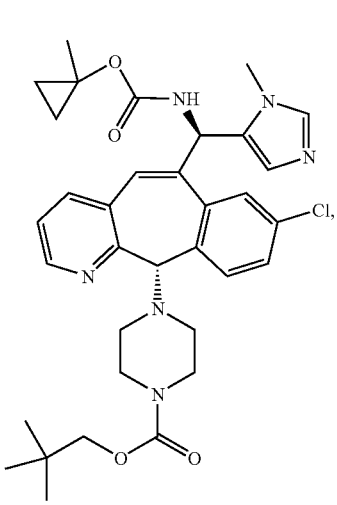 |
| 114.1 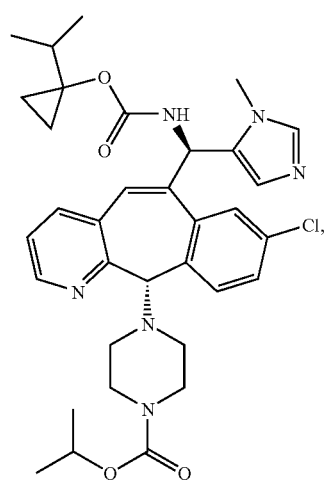 | 117.1 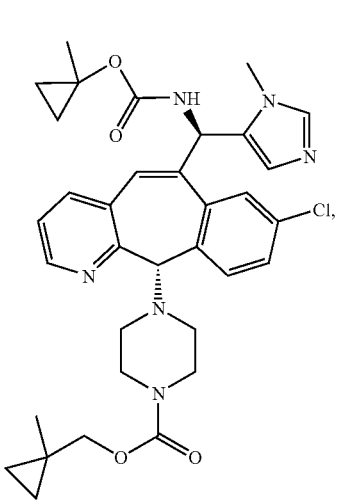 |

-continued
118.1
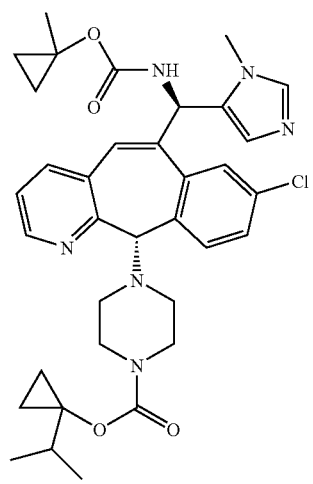
119.1
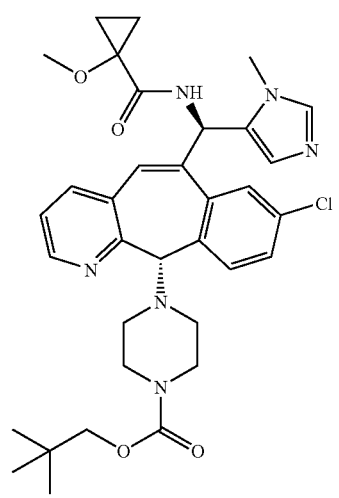
120.1
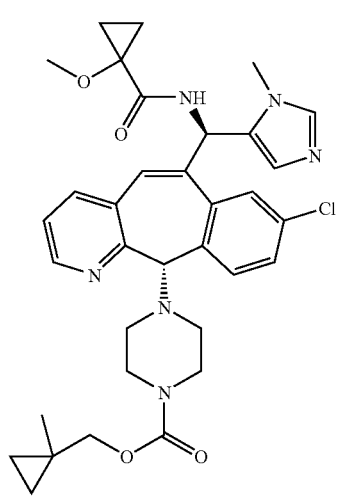
-continued
121.1
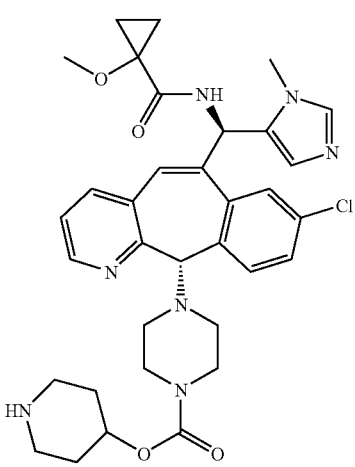
122.1
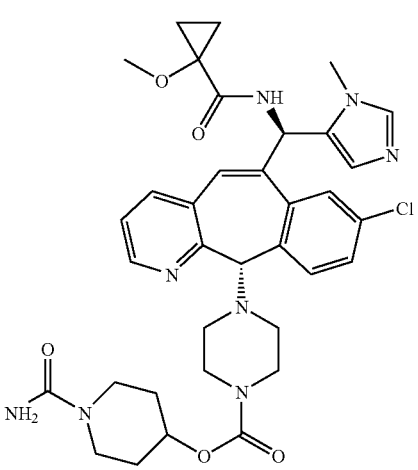
123.1
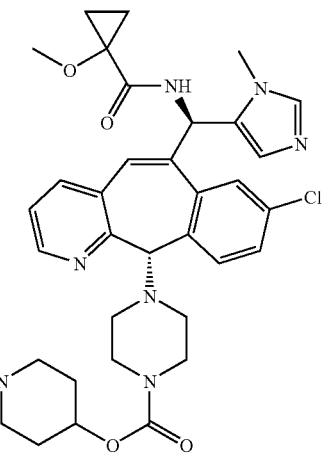

-continued
124.1
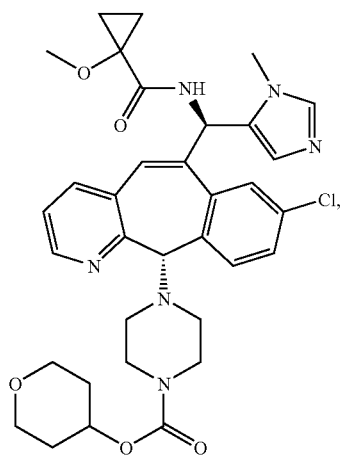
125.1
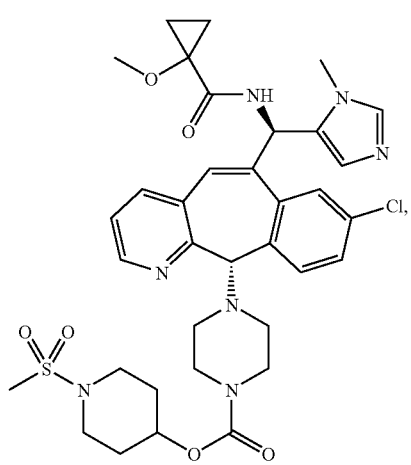
126.1
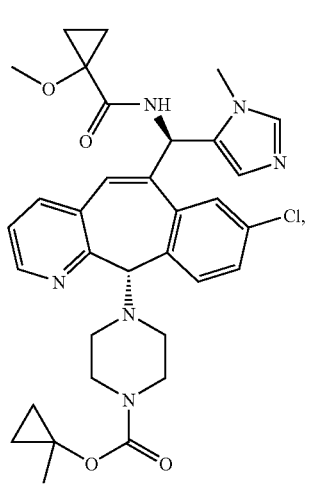
-continued
127.1
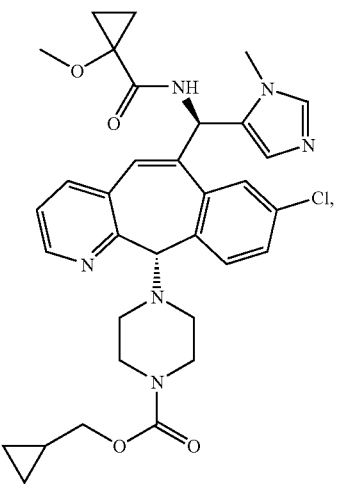
128.1
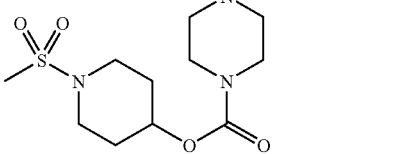
129.1
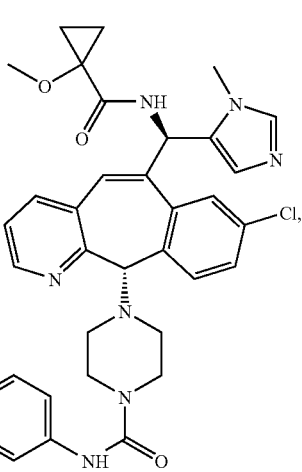

130.1
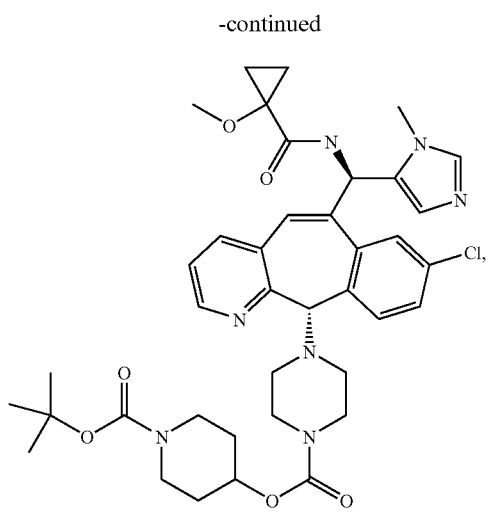
133.1
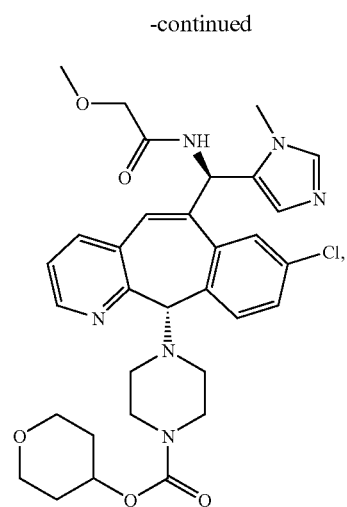
131.1
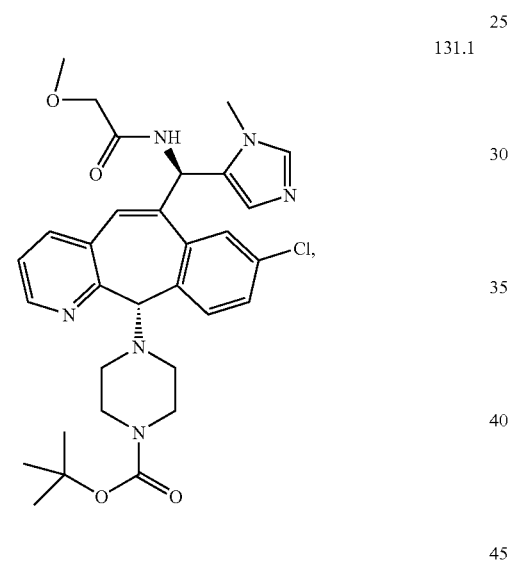
134.1
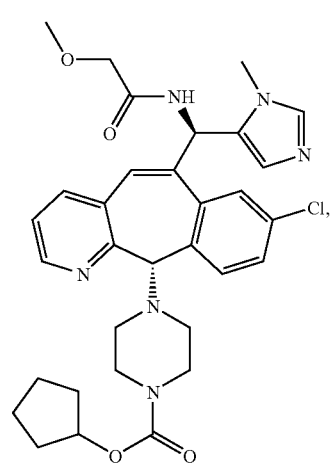
132.1
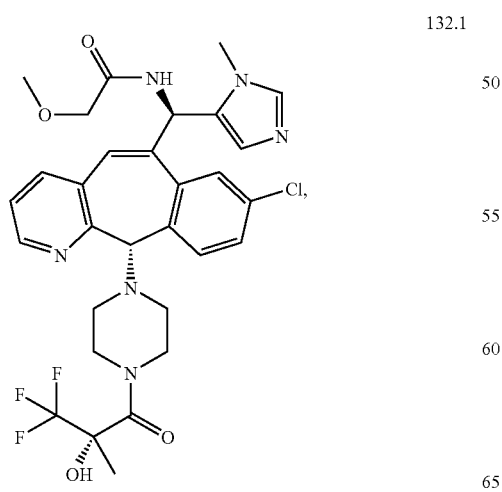
135.1
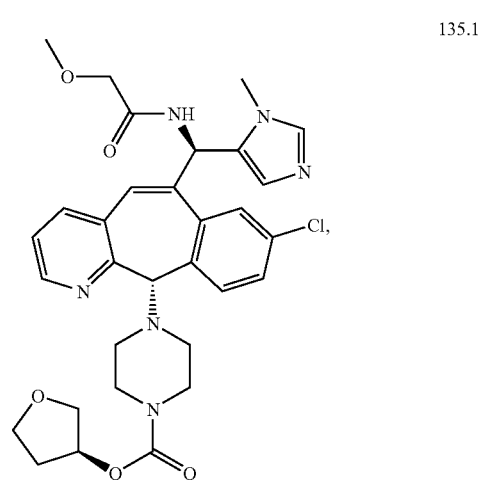

135.2
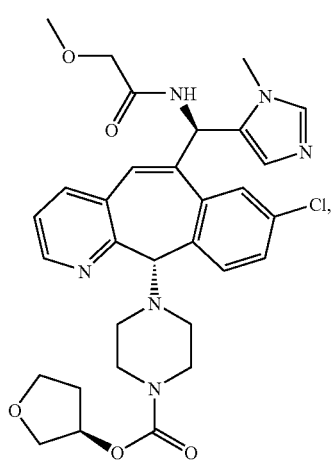
136.1
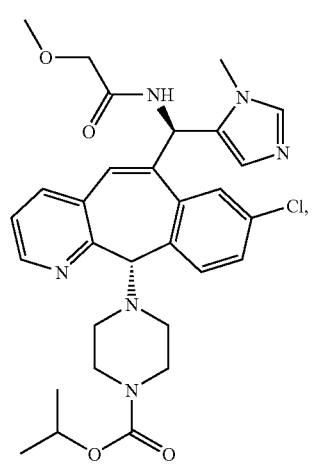
137.1
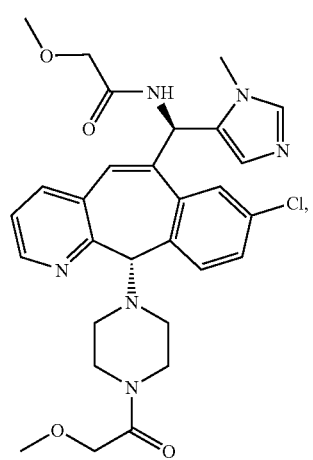
138.1
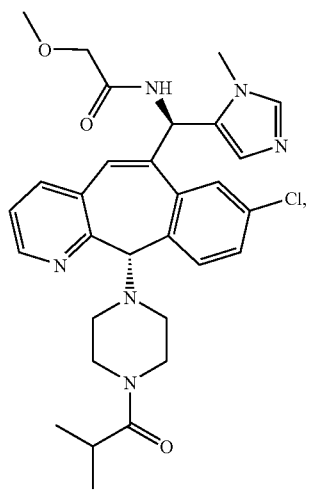
139.1
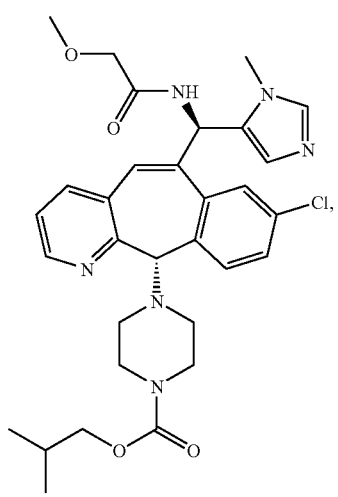
140.1
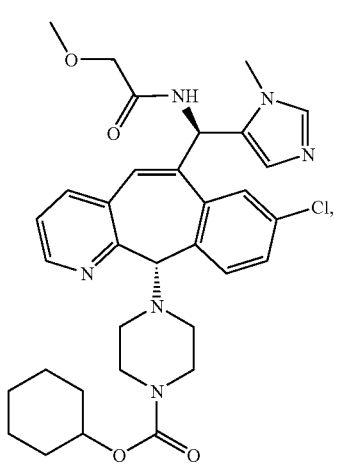

-continued
141.1
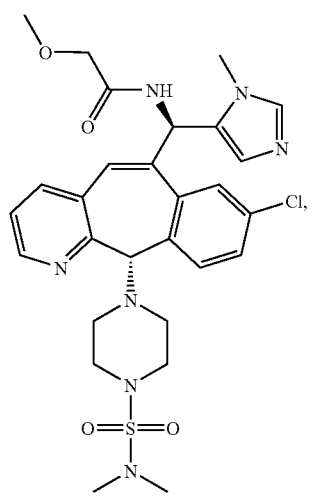
142.1
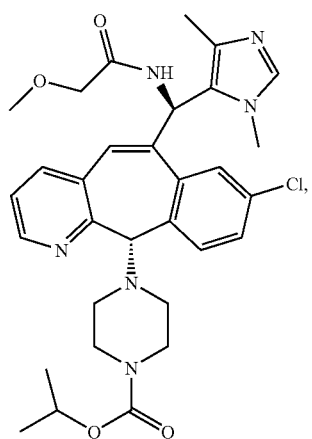
143.1
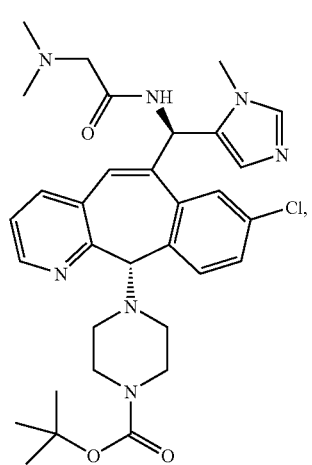
-continued
144.1
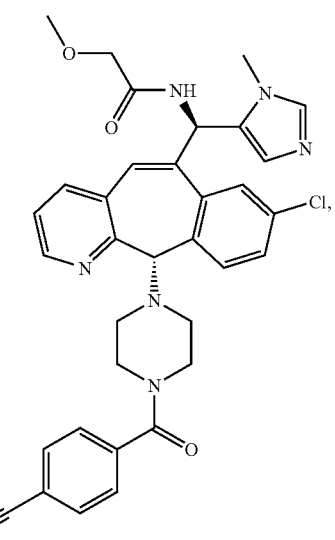
145.1
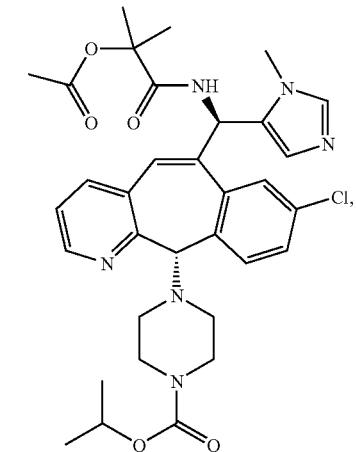
146.1
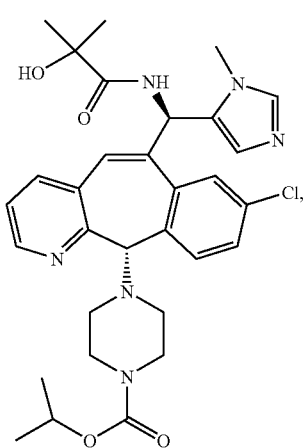

-continued
147.1
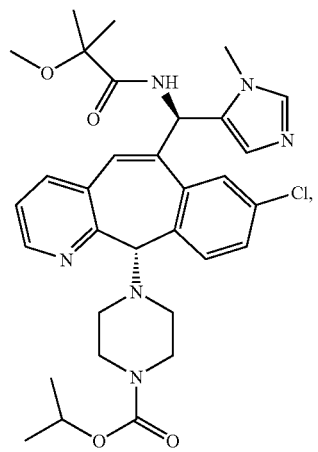
148.1
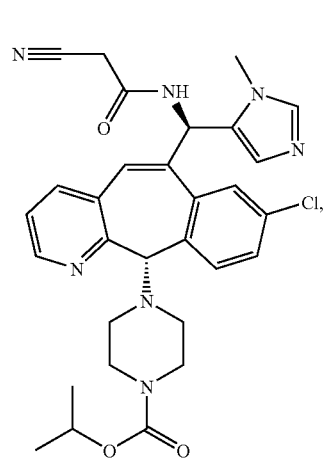
149.1
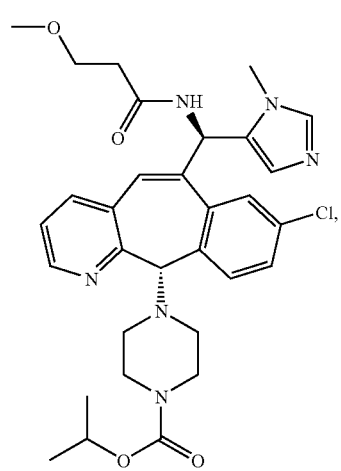
-continued
150.1
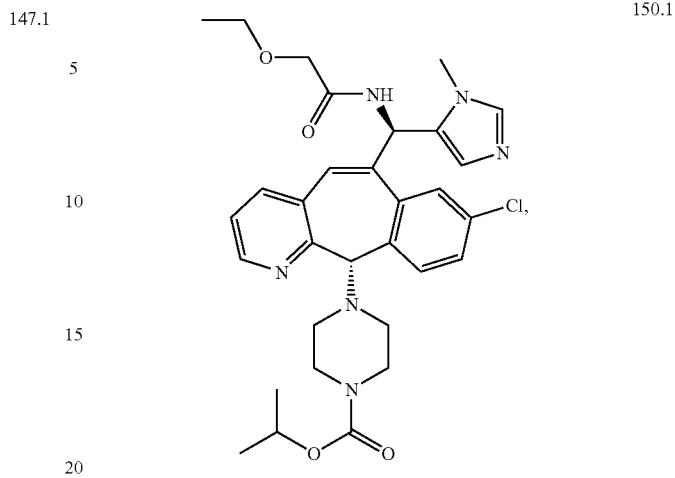
151.1
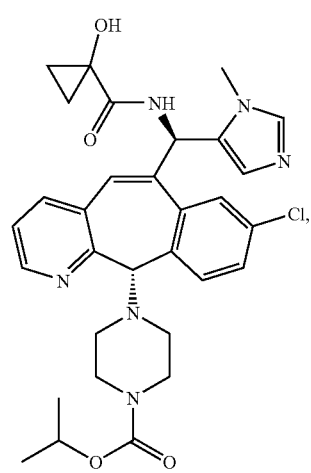
152.1
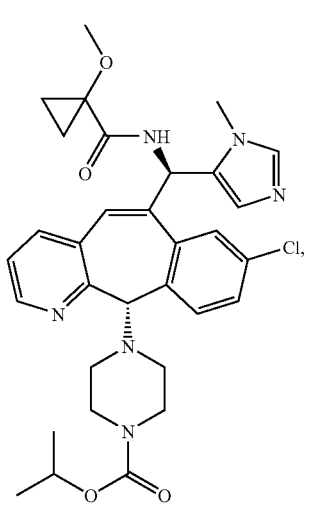

-continued
153.1
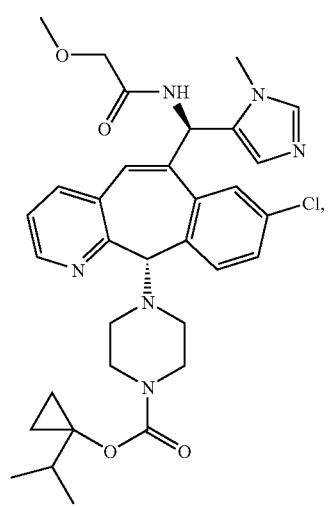
154.1
155.1
-continued
156.1
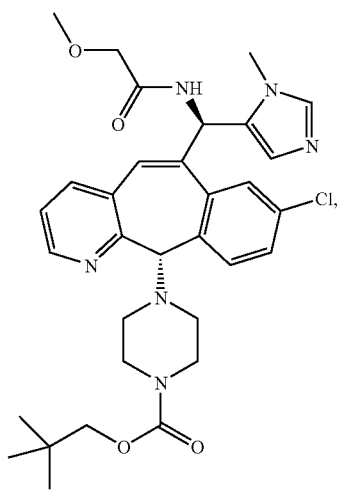
157.1
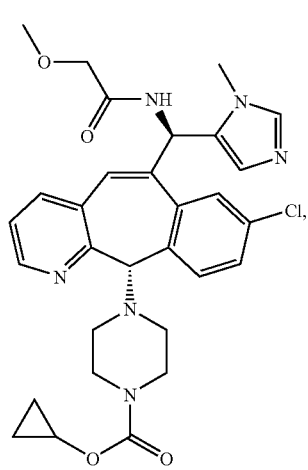
158.1
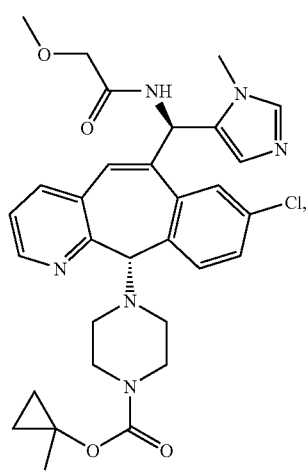

159.1
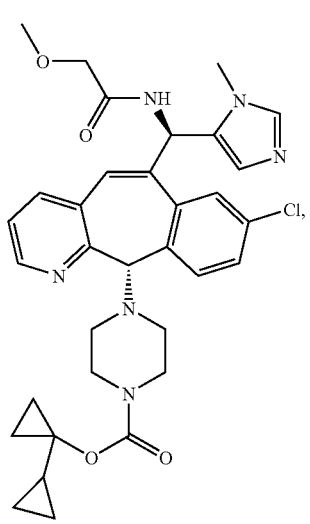
160.1
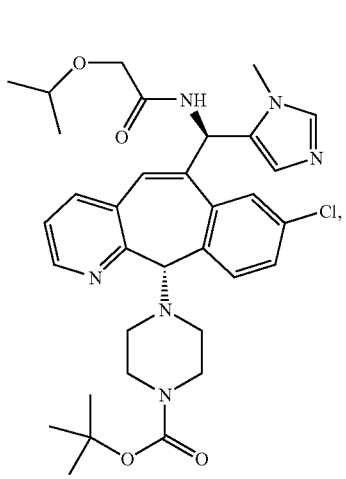
161.1
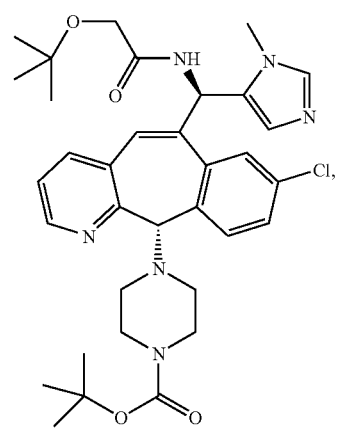
162.1
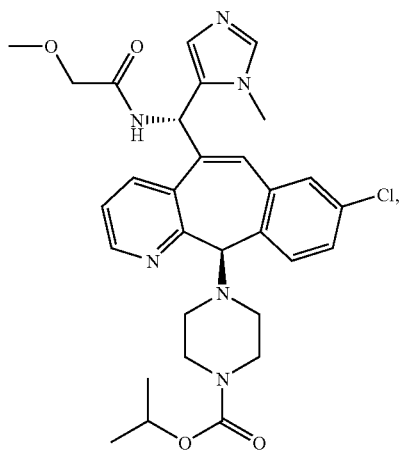
163.1
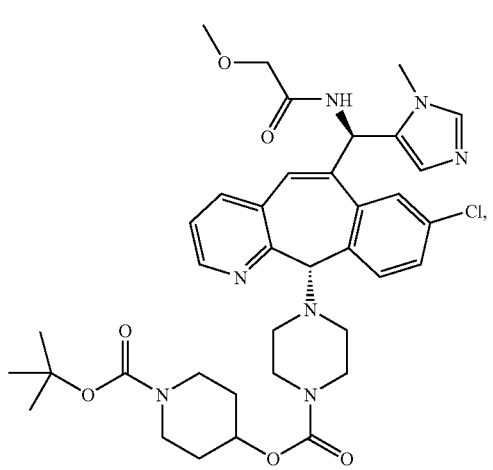
164.1
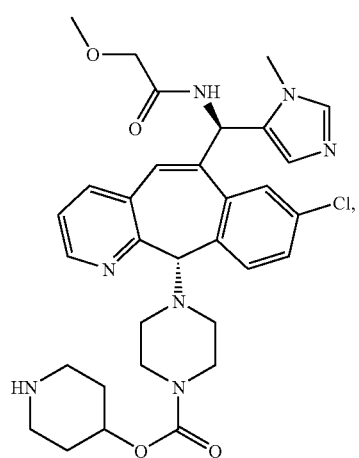

71
-continued
165.1
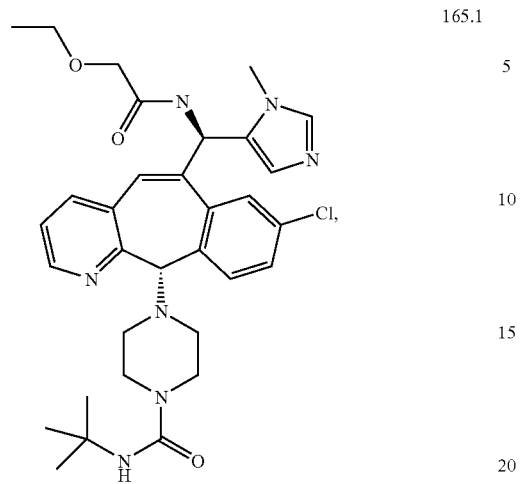
166.1
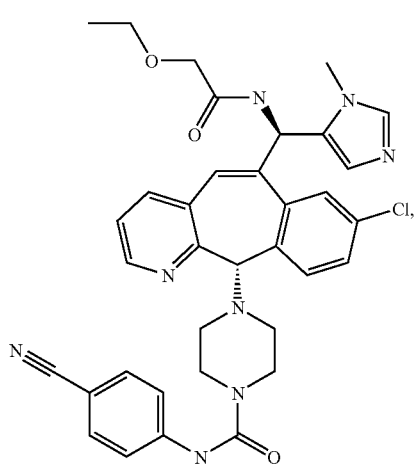
167.1
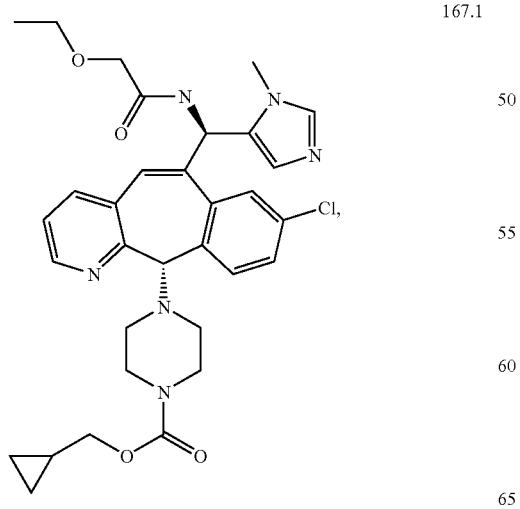
72
-continued
168.1
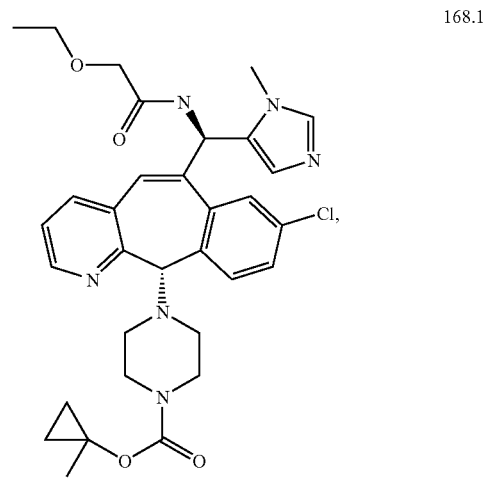
169.1
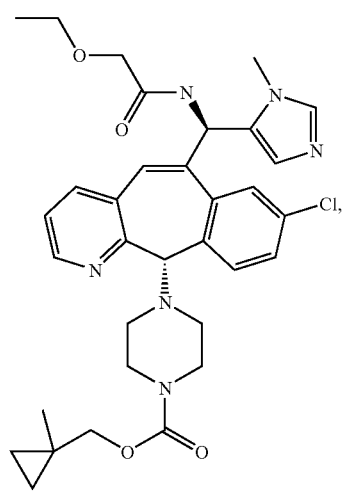
170.1
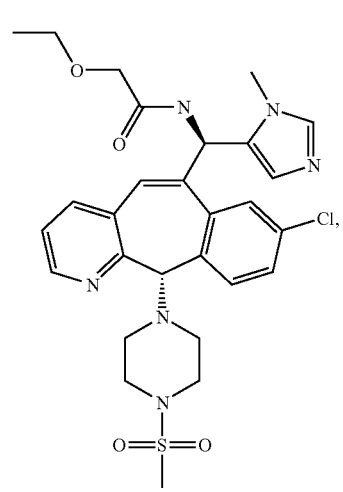

-continued 171.1

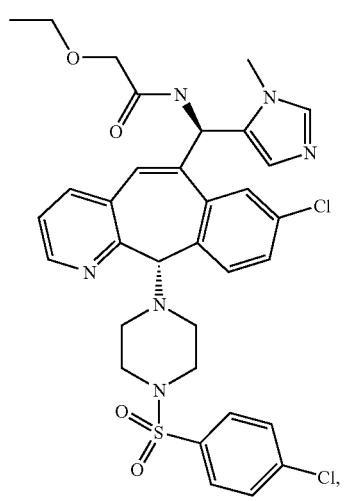

172.1

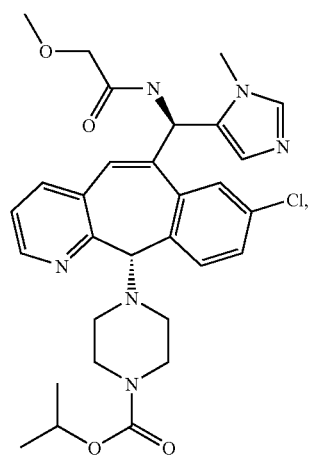

173.1

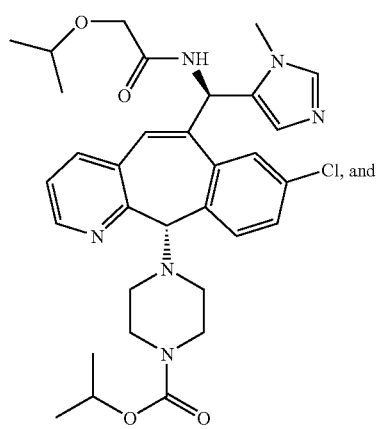

-continued 174.1

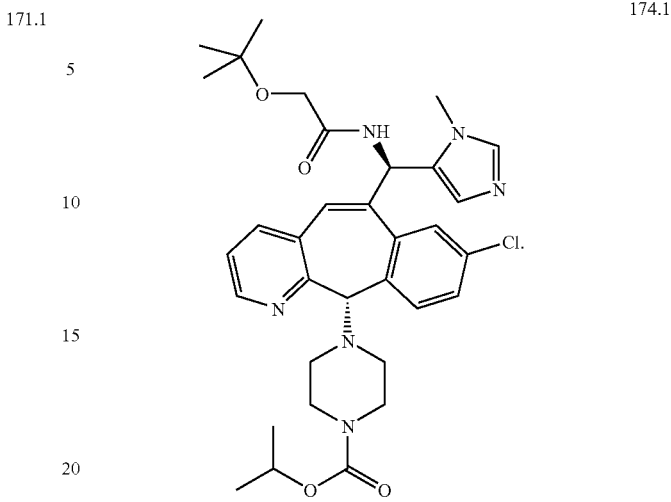

Lines drawn into the ring systems, such as, for example:

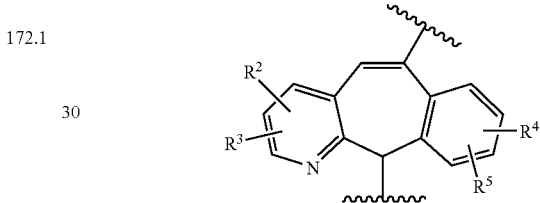

means that the indicated line (bond) may be attached to any of the substitutable ring carbon atoms.

It should also be noted that any carbon or heteroatom with unsatisfied valences in the text, schemes, examples, structural formulae, and any Tables herein is assumed to have the hydrogen atom or atoms to satisfy the valences.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prod rugs of the inventive compounds.

This invention also includes prodrugs of the compounds of this invention. The term "prodrug," as used herein, represents compounds that are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

This invention also includes the compounds of this invention in isolated and purified form.

Polymorphic forms of the compounds of formula I, and of the salts, solvates and prodrugs of the compounds of formula I, are intended to be included in the present invention.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

The compounds of formula I form salts that are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexyl amine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of formula 1.0, and salts, solvates and prodrugs thereof, may exist in their tautomeric form (for example, as an amide or imino ether). All such tautomeric forms are contemplated herein as part of the present invention.

The compounds of this invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount (e.g., a therapeutically effective amount) of one or more (e.g., one) compounds of this invention. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount (e.g., a therapeutically effective amount) of one or more (e.g., one) compounds of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor (i.e., cancer) growth by administering an effective amount (e.g., a therapeutically effective amount) of one or more (e.g., one) compounds of this invention to a mammal (e.g., a human) in need of such treatment. In particular, this invention provides a method for inhibiting or treating the growth of tumors expressing an activated Ras oncogene by the administration of an effective amount (e.g., a therapeutically effective amount) of the above described compounds.

The present invention also provides a method of treating proliferative diseases, especially cancers (i.e, tumors), comprising administering an effective amount (e.g., a therapeutically effective amount) of one or more (e.g., one) compounds of the invention, described herein, to a mammal (e.g., a human) in need of such treatment in combination with an effective amount of at least one anti-cancer agent (i.e., a chemotherapeutic agent) and/or radiation.

Examples of anti-cancer agents (i.e., chemotherapeutic agents) include anti-cancer agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of $\alpha V\beta 3$ integrins, (13) small molecules that are inhibitors of $\alpha V\beta 3$ integrins, (14) folate antagonists, (15) ribonucleotide reductase inhibitors, (16) anthracyclines, (17) biologics; (18) thalidomide (or related imid), and (19) Gleevec.

The present invention also provides a method of treating proliferative diseases, especially cancers (i.e., tumors), comprising administering an effective amount (e.g., a therapeutically effective amount) of one or more (e.g., one) compounds of the invention to a mammal (e.g., a human) in need of such treatment in combination with an effective amount of at least one signal transduction inhibitor.

Examples of proliferative diseases (tumors, i.e., cancers) which may be inhibited or treated include, but are not limited to: (A) lung cancer (e.g., lung adenocarcinoma and non small cell lung cancer), (B) pancreatic cancers (e.g., pancreatic carcinoma such as, for example, exocrine pancreatic carcinoma), (C) colon cancers (e.g., colorectal carcinomas, such as, for example, colon adenocarcinoma and colon adenoma), (D) myeloid leukemias (for example, acute myelogenous leukemia (AML), CML, and CMML), (E) thyroid follicular cancer, (F) myelodysplastic syndrome (MDS), (G) bladder carcinoma, (H) epidermal carcinoma, (I) melanoma, (J) breast cancer, (K) prostate cancer, (L) head and neck cancers (e.g., squamous cell cancer of the head and neck), (M) ovarian cancer, (N) brain cancers (e.g., gliomas), (O) cancers of mesenchymal origin (e.g., fibrosarcomas and rhabdomyosarcomas), (P) sarcomas, (Q) tetracarcinomas, (R) nuroblastomas, (S) kidney carcinomas, (T) hepatomas, (U) non-Hodgkin's lymphoma, (V) multiple myeloma, and (W) anaplastic thyroid carcinoma.

For example, embodiments of this invention include methods of treating cancer in a patient in need of such treatment wherein said cancer is selected from the group consisting of: pancreatic cancers, lung cancers, myeloid leukemias, thyroid follicular tumors, myelodysplastic syndrome, head and neck cancers, melanomas, breast cancers, prostate cancers, ovarian cancers, bladder cancers, gliomas, epidermal cancers, colon cancers, non-Hodgkin's lymphomas, and multiple myelomas comprising administering to said patient an effective amount of a compound of this invention Also for example, embodiments of this invention include methods of treating cancer in a patient in need of such treatment wherein said cancers are selected from the group consisting of: lung cancer (e.g., non-small cell lung cancer), head and neck cancer (e.g., squamous cell cancer of the head and neck), bladder cancer, breast cancer, prostate cancer, and myeloid leukemias (e.g., CML and AML), non-Hodgkin's lymphoma and multiple myeloma.

This invention also provides a method of treating cancer in a patient in need of such treatment comprising administering a therapeutically effective amount of one or more (e.g., one) compounds of this invention and therapeutically effective amounts of at least two different antineoplastic agents selected from: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of $\alpha V\beta 3$ integrins, (13) small molecules that are inhibitors of $\alpha V\beta 3$ integrins, (14) folate antagonists, (15) ribonucleotide reductase inhibitors, (16) anthracyclines, (17) biologics; (18) thalidomide (or related imid), and (19) Gleevec.

This invention also provides a method of treating cancer in a patient in need of such treatment comprising administering therapeutically effective amounts of one or more (e.g., one) compounds of this invention and an antineoplastic agent selected from: (1) EGF inhibitors that are antibodies, (2) EGF inhibitors that are small molecules, (3) VEGF inhibitors that are antibodies, and (4) VEGF inhibitors that are small molecules. Radiation therapy can also be used in conjunction with the above combination therapy, i.e., the above method using a combination of compounds of the invention and antineoplastic agent can also comprise the administration of a therapeutically effect amount of radiation.

This invention also provides a method of treating leukemias (e.g., acute myeloid leukemia (AML), and chronic-myeloid leukemia (CML)) in a patient in need of such treatment comprising administering therapeutically effective amounts of one or more (e.g., one) compounds of this invention and: (1) Gleevec and interferon to treat CML; (2) Gleevec and pegylated interferon to treat CML; (3) an anti-tumor nucleoside derivative (e.g., Ara-C) to treat AML; or (4) an anti-tumor nucleoside derivative (e.g., Ara-C) in combination with an anthracycline to treat AML.

This invention also provides a method of treating non-Hodgkin's lymphoma in a patient in need of such treatment comprising administering therapeutically effective amounts of one or more (e.g., one) compounds of this invention and: (1) a biologic (e.g., Rituxan); (2) a biologic (e.g., Rituxan) and an anti-tumor nucleoside derivative (e.g., Fludarabine); or (3) Genasense (antisense to BCL-2).

This invention also provides a method of treating multiple myeloma in a patient in need of such treatment comprising administering therapeutically effective amounts of one or more (e.g., one) compounds of this invention and: (1) a proteosome inhibitor (e.g., PS-341 from Millenium); or (2) Thalidomide (or related imid).

This invention also provides a method of treating cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, (12) antibodies that are inhibitors of $\alpha V\beta 3$ integrins, (13) small molecule inhibitors of $\alpha V\beta 3$ integrins, (14) folate antagonists, (15) ribonucleotide reductase inhibitors, (16) anthracyclines, (17) biologics, (18) Thalidomide (or related Imid), and (19) Gleevec.

This invention also provides a method of treating cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, (12) antibodies that are inhibitors of $\alpha V\beta 3$ integrins, (13) small molecule inhibitors of $\alpha V\beta 3$ integrins, (14) folate antagonists, (15) ribonucleotide reductase inhibitors, (16) anthracyclines, (17) biologics, and (18) Thalidomide (or related Imid).

This invention also provides a method of treating cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, (12) antibodies that are inhibitors of $\alpha V\beta 3$ integrins, (13) small molecule inhibitors of $\alpha V\beta 3$ integrins, (14) folate antagonists, (15) ribonucleotide reductase inhibitors, (16) anthracyclines, and (17) biologics.

This invention also provides a method of treating cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, (12) antibodies that are inhibitors of $\alpha V\beta 3$ integrins, and (13) small molecule inhibitors of $\alpha V\beta 3$ integrins.

This invention also provides a method of treating non small cell lung cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, (12) antibodies that are inhibitors of $\alpha V\beta 3$ integrins, and (13) small molecule inhibitors of $\alpha V\beta 3$ integrins.

This invention also provides a method of treating non small cell lung cancer comprising administering to a patient in need of such treatment therapeutically effective amounts of: (a) an FPT inhibitor of this invention, i.e., a compound of this invention, and (b) at least two different antineoplastic agents selected from the group consisting of: (1) taxanes, (2) platinum coordinator compounds, (3) anti-tumor nucleoside derivatives, (4) topoisomerase inhibitors, and (5) vinca alkaloids.

This invention also provides a method of treating non small cell lung cancer in a patient in need of such treatment comprising administering therapeutically effective amounts of: (a) an FPT inhibitor of this invention, i.e., a compound of this invention, (b) carboplatin, and (c) paclitaxel.

This invention also provides a method of treating non small cell lung cancer in a patient in need of such treatment comprising administering therapeutically effective amounts of: (a) an FPT inhibitor of this invention, i.e., a compound of this invention, (b) cisplatin, and (c) gemcitabine.

This invention also provides a method of treating non small cell lung cancer in a patient in need of such treatment comprising administering therapeutically effective amounts of: (a) an FPT inhibitor of this invention, i.e., a compound of this invention, (b) carboplatin, and (c) gemcitabine.

This invention also provides a method of treating non small cell lung cancer in a patient in need of such treatment comprising administering therapeutically effective amounts of: (a) an FPT inhibitor of this invention, i.e., a compound of this invention, (b) Carboplatin, and (c) Docetaxel.

This invention also provides a method of treating cancer in a patient in need of such treatment comprising administering therapeutically effective amounts of: (a) an FPT inhibitor of this invention, i.e., a compound of this invention, and (b) an antineoplastic agent selected from the group consisting of: (1) EGF inhibitors that are antibodies, (2) EGF inhibitors that are small molecules, (3) VEGF inhibitors that are antibodies, (4) VEGF kinase inhibitors that are small molecules.

This invention also provides a method of treating squamous cell cancer of the head and neck, in a patient in need of such treatment comprising administering therapeutically effective amounts of: (a) an FPT inhibitor of this invention, i.e., a compound of this invention, and (b) one or more antineoplastic agents selected from the group consisting of: (1) taxanes, and (2) platinum coordinator compounds.

This invention also provides a method of treating squamous cell cancer of the head and neck, in a patient in need of such treatment comprising administering therapeutically effective amounts of: (a) an FPT inhibitor of this invention, i.e., a compound of this invention, and (b) at least two different antineoplastic agents selected from the group consisting of: (1) taxanes, (2) platinum coordinator compounds, and (3) anti-tumor nucleoside derivatives (e.g., 5-Fluorouracil).

This invention also provides a method of treating CML in a patient in need of such treatment comprising administering therapeutically effective amounts of: (a) an FPT inhibitor of this invention, i.e., a compound of this invention, (b) Gleevec, and (c) interferon (e.g., Intron-A).

This invention also provides a method of treating CML in a patient in need of such treatment comprising administering therapeutically effective amounts of: (a) an FPT inhibitor of this invention, i.e., a compound of this invention, (b) Gleevec; and (c) pegylated interferon (e.g., Peg-Intron, and Pegasys).

This invention also provides a method of treating CML in a patient in need of such treatment comprising administering therapeutically effective amounts of: (a) an FPT inhibitor of this invention, i.e., a compound of this invention and (b) Gleevec.

This invention also provides a method of treating CMML in a patient in need of such treatment comprising administering therapeutically effective amounts of an FPT inhibitor of this invention i.e., a compound of this invention.

This invention also provides a method of treating AML in a patient in need of such treatment comprising administering therapeutically effective amounts of: (a) an FPT inhibitor of this invention, i.e., a compound of this invention, (b) an anti-tumor nucleoside derivative (e.g., Cytarabine (i.e., Ara-C)).

This invention also provides a method of treating AML in a patient in need of such treatment comprising administering therapeutically effective amounts of: (a) an FPT inhibitor of this invention, i.e., a compound of this invention, (b) an anti-tumor nucleoside derivative (e.g., Cytarabine (i.e., Ara-C)), and (c) an anthracycline.

This invention also provides a method of treating non-Hodgkin's lymphoma in a patient in need of such treatment comprising administering therapeutically effective amounts of: (a) an FPT inhibitor of this invention, i.e., a compound of this invention, and (b) Rituximab (Rituxan).

This invention also provides a method of treating non-Hodgkin's lymphoma in a patient in need of such treatment comprising administering therapeutically effective amounts of: (a) an FPT inhibitor of this invention, i.e., a compound of this invention, (b) Rituximab (Rituxan), and (c) an anti-tumor nucleoside derivative (e.g., Fludarabine (i.e., F-ara-A).

This invention also provides a method of treating non-Hodgkin's lymphoma in a patient in need of such treatment comprising administering therapeutically effective amounts of: (a) an FPT inhibitor of this invention, i.e., a compound of this invention, (b) Genasense (antisense to BCL-2).

This invention also provides a method of treating multiple myeloma in a patient in need of such treatment comprising administering therapeutically effective amounts of: (a) an FPT inhibitor of this invention, i.e., a compound of this invention, and (b) a proteosome inhibitor (e.g., PS-341 (Millenium)).

This invention also provides a method of treating multiple myeloma in a patient in need of such treatment comprising administering therapeutically effective amounts of: (a) an FPT inhibitor of this invention, i.e., a compound of this invention, and (b) Thalidomide or related imid.

This invention also provides a method of treating multiple myeloma in a patient in need of such treatment comprising administering therapeutically effective amounts of: (a) an FPT inhibitor of this invention, i.e., a compound of this invention, and (b) Thalidomide.

This invention is also directed to the methods of treating cancer described herein, particularly those described above, wherein in addition to the administration of the FPT inhibitor and antineoplastic agents radiation therapy is also administered prior to, during, or after the treatment cycle.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount (e.g. a therapeutically effective amount) of one or more (e.g., one) compounds of the invention to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The compounds of this invention useful in the methods of this invention inhibit or treat the abnormal growth of cells. Without wishing to be bound by theory, it is believed that these compounds may function through the inhibition of G-protein function, such as Ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

The method of treating proliferative diseases (cancers, i.e., tumors), according to this invention, includes a method for treating (inhibiting) the abnormal growth of cells, including transformed cells, in a patient in need of such treatment, by administering, concurrently or sequentially, an effective amount of a compound of this invention and an effective amount of a chemotherapeutic agent and/or radiation.

In embodiments, the methods of the present invention include methods for treating or inhibiting tumor growth in a patient in need of such treatment by administering, concurrently or sequentially, (1) an effective amount of a compound of this invention and (2) an effective amount of at least one antineoplastic agent, microtubule affecting agent and/or radiation therapy. For example, one embodiment of these methods is directed to a method of treating cancers selected from the group consisting of: lung cancer, prostate cancer and myeloid leukemias.

The methods of treating proliferative diseases, according to this invention, also include a method for treating (inhibiting) proliferative diseases, both benign and malignant, wherein ras proteins are aberrantly activated as a result of oncogenic mutation in other genes —i.e., the ras gene itself is not activated by mutation to an oncogenic form. This method comprises administering, concurrently or sequentially, an effective amount of a compound of this invention and an effective amount of an antineoplastic agent and/or radiation therapy to a patient in need of such treatment. Examples of such proliferative diseases which may be treated include: the benign proliferative disorder neurofibromatosis, or tumors in which ras is activated due to mutation or overexpression of tyrosine kinase oncogenes (e.g., neu, src, abl, lck, lyn, fyn).

For radiation therapy, γ-radiation is preferred.

The methods of treating proliferative diseases (cancers, i.e., tumors), according to this invention, also include a method for treating (inhibiting) the abnormal growth of cells, including transformed cells, in a patient in need of such treatment, by administering, concurrently or sequentially, an effective amount of a compound of this invention and an effective amount of at least one signal transduction inhibitor.

Typical signal transduction inhibitors include but are not limited to: (i) Bcr/abl kinase inhibitors such as, for example, STI 571 (Gleevec), (ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin® (trastuzumab).

Embodiments of the methods of treatment of this invention are directed to the use of a combination of drugs (compounds) for the treatment of cancer, i.e., this invention is directed to a combination therapy for the treatment of cancer. Those skilled in the art will appreciate that the drugs are generally administered individually as a pharmaceutical composition. The use of a pharmaceutical composition comprising more than one drug is within the scope of this invention.

The antineoplastic agents are usually administered in the dosage forms that are readily available to the skilled clinician, and are generally administered in their normally prescribed amounts (as for example, the amounts described in the Physician's Desk Reference, 56$^{th}$ Edition, 2002 (published by Medical Economics company, Inc. Montvale, N.J. 07645-1742, and in the Physician's Desk Reference, 57$^{th}$ Edition, 2003 (published by Thompson PDR, Montvale, N.J. 07645-1742, the disclosures of which are incorporated herein by reference thereto)), or the amounts described in the manufacture's literature for the use of the agent).

For example, the FPT inhibitor of this invention, i.e., a compound of this invention; can be administered orally (e.g., as a capsule), and the antineoplastic agents can be administered intravenously, usually as an IV solution. The use of a pharmaceutical composition comprising more than one drug is within the scope of this invention.

The FPT inhibitor (i.e., compound of this invention) and the antineoplastic agents are administered in therapeutically effective dosages to obtain clinically acceptable results, e.g., reduction or elimination of symptoms or of the tumor. Thus, the FPT inhibitor and antineoplastic agents can be administered concurrently or consecutively in a treatment protocol. The administration of the antineoplastic agents can be made according to treatment protocols already known in the art.

The FPT inhibitor (i.e., compound of this invention) and antineoplastic agents are administered in a treatment protocol that usually lasts one to seven weeks, and is repeated typically from 6 to 12 times. Generally the treatment protocol lasts one to four weeks. Treatment protocols of one to three weeks may also be used. A treatment protocol of one to two weeks may also be used. During this treatment protocol or cycle the FPT inhibitor is administered daily while the antineoplastic agents are administered one or more times a week. Generally, the FPT inhibitor can be administered daily (i.e., once per day), and in one embodiment twice per day, and the antineoplastic agent is administered once a week or once every three weeks. For example, the taxanes (e.g., Paclitaxel (e.g., Taxol®) or Docetaxel (e.g.,Taxotere®)) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the FPT inhibitor (i.e., compound of this invention) can be administered discontinuously rather than continuously during the treatment cycle. Thus, for example, during the treatment cycle the FPT inhibitor can be administered daily for a week and then discontinued for a week, with this administration repeating during the treatment cycle. Or the FPT inhibitor can be administered daily for two weeks and discontinued for a week, with this administration repeating during the treatment cycle. Thus, the FPT inhibitor can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the FPT inhibitor is not dosed does not have to equal the number of days (or weeks) wherein the FPT inhibitor is dosed. Usually, if a discontinuous dosing protocol is used, the number of days or weeks that the FPT inhibitor is dosed is at least equal or greater than the number of days or weeks that the FPT inhibitor is not dosed.

The antineoplastic agent could be given by bolus or continuous infusion. The antineoplastic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

The FPT inhibitor (i.e., compound of this invention) can be administered orally, preferably as a solid dosage form, and in one embodiment as a capsule, and while the total therapeutically effective daily dose can be administered in one to four, or one to two divided doses per day, generally, the therapeutically effective dose is given once or twice a day, and in one embodiment twice a day. The FPT inhibitor can be administered in an amount of about 50 to about 400 mg once per day, and can be administered in an amount of about 50 to about 300 mg once per day. The FPT inhibitor is generally administered in an amount of about 50 to about 350 mg twice a day, usually 50 mg to about 200 mg twice a day, and in one embodiment about 75 mg to about 125 mg administered twice a day, and in another embodiment about 100 mg administered twice a day.

If the patient is responding, or is stable, after completion of the therapy cycle, the therapy cycle can be repeated according to the judgment of the skilled clinician. Upon completion of the therapy cycles, the patient can be continued on the FPT inhibitor (i.e., compound of this invention) at the same dose that was administered in the treatment protocol, or, if the dose was less than 200mg twice a day, the dose can be raised to 200 mg twice a day. This maintenance dose can be continued until the patient progresses or can no longer tolerate the dose (in which case the dose can be reduced and the patient can be continued on the reduced dose).

The antineoplastic agents used with the FPT inhibitor (i.e., compound of this invention) are administered in their normally prescribed dosages during the treatment cycle (i.e., the antineoplastic agents are administered according to the standard of practice for the administration of these drugs). For example: (a) about 30 to about 300 mg/m² for the taxanes; (b) about 30 to about 100 mg/m² for Cisplatin; (c) AUC of about 2 to about 8 for Carboplatin; (d) about 2 to about 4 mg/m² for EGF inhibitors that are antibodies; (e) about 50 to about 500 mg/m² for EGF inhibitors that are small molecules; (f) about 1 to about 10 mg/m² for VEGF kinase inhibitors that are antibodies; (g) about 50 to about 2400 mg/m² for VEGF inhibitors that are small molecules; (h) about 1 to about 20 mg for SERMs; (i) about 500 to about 1250 mg/m² for the anti-tumor nucleosides 5-Fluorouracil, Gemcitabine and Capecitabine; (j) for the anti-tumor nucleoside Cytarabine (Ara-C) 100-200 mg/m²/day for 7 to 10 days every 3 to 4 weeks, and high doses for refractory leukemia and lymphoma, i.e., 1 to 3 gm/m² for one hour every 12 hours for 4-8 doses every 3 to four weeks; (k) for the anti-tumor nucleoside Fludarabine (F-ara-A) 10-25 mg/m²/day every 3 to 4 weeks; (l) for the anti-tumor nucleoside Decitabine 30 to 75 mg/m² for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m² for epothilones; (o) about 1 to about 350 mg/m² for topoisomerase inhibitors; (p) about 1 to about 50 mg/m² for vinca alkaloids; (q) for the folate antagonist Methotrexate (MTX) 20-60 mg/m² by oral, IV or IM every 3 to 4 weeks, the intermediate dose regimen is 80-250 mg/m² IV over 60 minutes every 3 to 4 weeks, and the high dose regimen is 250-1000 mg/m² IV given with leucovorin every 3 to 4 weeks; (r) for the folate antagonist Premetrexed (Alimta) 300-600 mg/m² (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m² every 3 to 4 weeks (preferably used for solid tumors such as non-small cell lung cancer, colorectal cancer and ovarian cancer); (u) for the anthracycline daunorubicin 10-50 mg/m²/day IV for 3-5 days every 3 to 4 weeks; (v) for the anthracycline Doxorubicin (Adriamycin) 50-100 mg/m² IV continuous infusion over 1-4 days every 3 to 4 weeks, or 10-40 mg/m² IV weekly; (w) for the anthracycline Idarubicin 10-30 mg/m² daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); and (z) for the biologic Rituximab (Rituxan) (antibody used for non-Hodgkin's lymphoma) 200-400 mg/m² IV weekly over 4-8 weeks for 6 months.

Gleevec can be used orally in an amount of about 200 to about 800 mg/day.

Thalidomide (and related imids) can be used orally in amounts of about 200 to about 800 mg/day, and can be contiuously dosed or used until releapse or toxicity. See for example Mitsiades et al., "Apoptotic signaling induced by immunomodulatory thalidomide analoqs in human multiple myeloma cells;therapeutic implications", Blood, 99(12):4525-30, Jun. 15, 2002, the disclosure of which is incorporated herein by reference thereto.

For example, Paclitaxel (e.g., Taxol® can be administered once per week in an amount of about 50 to about 100 mg/m² and in another example about 60 to about 80 mg/m². In another example Paclitaxel (e.g., Taxol® can be administered once every three weeks in an amount of about 150 to about 250 mg/m² and in another example about 175 to about 225 mg/m².

In another example, Docetaxel (e.g., Taxotere®) can be administered once per week in an amount of about 10 to about 45 mg/m². In another example Docetaxel (e.g., Taxotere®) can be administered once every three weeks in an amount of about 50 to about 100 mg/m².

In another example Cisplatin can be administered once per week in an amount of about 20 to about 40 mg/m². In another example Cisplatin can be administered once every three weeks in an amount of about 60 to about 100 mg/m².

In another example Carboplatin can be administered once per week in an amount to provide an AUC of about 2 to about 3. In another example Carboplatin can be administered once every three weeks in an amount to provide an AUC of about 5 to about 8.

Thus, in one example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Paclitaxel (e.g., Taxol®) is administered once per week in an amount of about 50 to about 100 mg/m², and in another example about 60 to about 80 mg/m², and (3) Carboplatin is administered once per week in an amount to provide an AUC of about 2 to about 3.

In another example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and yet in another example about 100 mg administered twice a day, (2) Paclitaxel (e.g., Taxol®) is administered once per week in an amount of about 50 to about 100 mg/m², and in another example about 60 to about 80 mg/m², and (3) Cisplatin is administered once per week in an amount of about 20 to about 40 mg/m².

In another example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m², and (3) Carboplatin is administered once per week in an amount to provide an AUC of about 2 to about 3.

In another example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m², and (3) Cisplatin is administered once per week in an amount of about 20 to about 40 mg/m².

Thus, in one example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Paclitaxel (e.g., Taxol®) is administered once every three weeks in an amount of about 150 to about 250 mg/m², and in another example about 175 to about 225 mg/m², and in yet another example 175 mg/m², and (3) Carboplatin is administered once every three weeks in an amount to provide an AUC of about 5 to about 8, and in another example 6.

In another example of treating non small cell lung cancer: (1) the FPT inhibitor (i.e., compound of this invention) is administered in an amount of 100 mg administered twice a day, (2) Paclitaxel (e.g., Taxol®) is administered once every three weeks in an amount of 175 mg/m$^2$, and (3) Carboplatin is administered once every three weeks in an amount to provide an AUC of 6.

In another example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Paclitaxel (e.g., Taxol®) is administered once every three weeks in an amount of about 150 to about 250 mg/m$^2$, and in another example about 175 to about 225 mg/m$^2$, and (3) Cisplatin is administered once every three weeks in an amount of about 60 to about 100 mg/m$^2$.

In another example (e.g., treating non small cell lung cancer): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once every three weeks in an amount of about 50 to about 100 mg/m$^2$, and (3) Carboplatin is administered once every three weeks in an amount to provide an AUC of about 5 to about 8.

In another example (e.g., treating non small cell lung cancer): (1) the FPT inhibitor (i.e., compound of this invention) is administered in an amount of about 50 mg to about 200 mg twice a day, in another example about 75 mg to about 125 mg administered twice a day, and in yet another example about 100 mg administered twice a day, (2) Docetaxel (e.g., Taxotere®) is administered once every three weeks in an amount of about 50 to about 100 mg/m$^2$, and (3) Cisplatin is administered once every three weeks in an amount of about 60 to about 100 mg/m$^2$.

In another example for treating non small cell lung cancer using the FPT inhibitor (i.e., compound of this invention), Docetaxel and Carboplatin: (1) the FPT inhibitor is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once every three weeks in an amount of about 75 mg/m$^2$, and (3) Carboplatin is administered once every three weeks in an amount to provide an AUC of about 6.

In another example of the the above examples the Docetaxel (e.g., Taxotere®) and Cisplatin, the Docetaxel (e.g., Taxotere®) and Carboplatin, the Paclitaxel (e.g., Taxol®) and Carboplatin, or the Paclitaxel (e.g., Taxol®) and Cisplatin are administered on the same day.

In another example (e.g., CML): (1) the FPT inhibitor (i.e., compound of this invention) is administered in an amount of about 100 mg to about 200 mg administered twice a day, (2) Gleevec is administered in an amount of about 400 to about 800 mg/day orally, and (3) interferon (Intron-A) is administered in an amount of about 5 to about 20 million IU three times per week.

In another example (e.g., CML): (1) the FPT inhibitor (i.e., compound of this invention) is administered in an amount of about 100 mg to about 200 mg administered twice a day, (2) Gleevec is administered in an amount of about 400 to about 800 mg/day orally, and (3) pegylated interferon (Peg-Intron or Pegasys) is administered in an amount of about 3 to about 6 micrograms/kg/day.

In another example (e.g., non-Hodgkin's lymphoma): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, and (2) Genasense (antisense to BCL-2) is administered as a continuous IV infusion at a dose of about 2 to about 5 mg/kg/day (e.g., 3 mg/kg/day) for 5 to 7 days every 3 to 4 weeks.

In another example (e.g., multiple myeloma): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day,. and (2) the proteosome inhibitor (e.g., PS-341—Millenium) is administered in an amount of about 1.5 mg/m$^2$ twice weekly for two consecutive weeks with a one week rest period.

In another example (e.g., multiple myeloma): (1) the FPT inhibitor (i.e., compound of this invention) is administered in an amount of about 50 mg to about 200 mg twice a day, and in another example about 75 mg to about 125 mg administered twice a day, and in yet another example about 100 mg administered twice a day, and (2) the Thalidomide (or related imid) is administered orally in an amount of about 200 to about 800 mg/day, with dosing being continuous until relapse or toxicity.

In another example of the above examples the Taxotere and cisplatin, the Taxotere and carboplatin, the Taxol and carboplatin, or the Taxol and cisplatin are administered on the same day.

Antineoplastic agents that can be used in combination with the FPT inhibitor (i.e., compound of this invention) are: (1) taxanes such as paclitaxel (TAXOL®) and/or docetaxel (Taxotere®), (2) platinum coordinator compounds, such as, for example, carboplatin, cisplatin and oxaliplatin, (3) EGF inhibitors that are antibodies, such as: HER2 antibodies (such as, for example trastuzumab (Herceptin®), Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), Cl 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA), (4) EGF inhibitors that are small molecules, such as, Tarceva ™ (OSI-774, OSI Pharmaceuticals, Inc.), and Iressa (ZD 1839, Astra Zeneca), (5) VEGF inhibitors that are antibodies such as: bevacizumab (Genentech, Inc.), and IMC-1C11 (ImClone Systems), DC 101 (a KDR VEGF Receptor 2 from ImClone Systems), (6) VEGF kinase inhibitors that are small molecules such as SU 5416 (from Sugen, Inc), SU 6688 (from Sugen, Inc.), Bay43-9006 (a dual VEGF and bRAF inhibitor from Bayer Pharmaceuticals and Onyx Pharmaceuticals), (7) estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.), (8) anti-tumor nucleoside derivatives such as 5-fluorouracil, gemcitabine or capecitabine, (9) epothilones such as BMS-247550 (Bristol-Myers Squibb), and EP0906 (Novartis Pharmaceuticals), (10) topoisomerase inhibitors such as topotecan (Glaxo SmithKline), and Camptosar (Pharmacia), (11) vinca alkaloids, such as, navelbine (Anvar and Fabre, France), vincristine and vinblastine, and (12) antibodies that are inhibitors of αVβ3 integrins, such as, LM-609 (see, Clinical Cancer Research, Vol. 6, page 3056-3061, August 2000, the disclosure of which is incorporated herein by reference thereto).

In one embodiment the antineoplastic agents are selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688. In another embodiment the antineoplastic agents are selected from the group consisting of: paclitaxel, docetaxel, carboplatin, cisplatin, navelbine, gemcitabine, and Herceptin.

In general when more than one antineoplastic agent is used in the methods of this invention, the antineoplastic agents are administered on the same day either concurrently or consecutively in their standard dosage form. For example, the antineoplastic agents are usually administered intravenously, preferably by an IV drip using IV solutions well known in the art (e.g., isotonic saline (0.9% NaCl) or dextrose solution (e.g., 5% dextrose)).

When two or more antineoplastic agents are used, the antineoplastic agents are generally administered on the same day; however, those skilled in the art will appreciate that the antineoplastic agents can be administered on different days and in different weeks. The skilled clinician can administer the antineoplastic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

Thus, one embodiment of this invention is directed to a method of treating cancer comprising administering to a patient in need of such treatment therapeutically effective amounts of the FPT inhibitor (i.e., compound of this invention), a taxane, and a platinum coordination compound.

Another embodiment of this invention is directed to a method of treating cancer comprising administering to a patient in need of such treatment therapeutically effective amounts of the FPT inhibitor (i.e., compound of this invention), a taxane, and a platinum coordination compound, wherein said FPT inhibitor is administered every day, said taxane is administered once per week per cycle, and said platinum coordinator compound is administered once per week per cycle. In another embodiment the treatment is for one to four weeks per cycle.

Another embodiment of this invention is directed to a method of treating cancer comprising administering to a patient in need of such treatment therapeutically effective amounts of the FPT inhibitor (i.e., compound of this invention), a taxane, and a platinum coordination compound, wherein said FPT inhibitor is administered every day, said taxane is administered once every three weeks per cycle, and said platinum coordinator compound is administered once every three weeks per cycle. In another embodiment the treatment is for one to three weeks per cycle.

Another embodiment of this invention is directed to a method of treating cancer comprising administering to a patient in need of such treatment therapeutically effective amounts of the FPT inhibitor (i.e., compound of this invention), paclitaxel, and carboplatin. In another embodiment, said FPT inhibitor is administered every day, said paclitaxel is administered once per week per cycle, and said carboplatin is administered once per week per cycle. In another embodiment the treatment is for one to four weeks per cycle.

Another embodiment of this invention is directed to a method of treating cancer comprising administering to a patient in need of such treatment therapeutically effective amounts of the FPT inhibitor (i.e., compound of this invention), paclitaxel, and carboplatin. In another embodiment, said FPT inhibitor is administered every day, said paclitaxel is administered once every three weeks per cycle, and said carboplatin is administered once every three weeks per cycle. In another embodiment the treatment is for one to three weeks per cycle.

Another embodiment of this invention is directed to a method for treating non small cell lung cancer in a patient in need of such treatment comprising administering daily a therapeutically effective amount of the FPT inhibitor (i.e., compound of this invention), administering a therapeutically effective amount of carboplatin once a week per cycle, and administering a therapeutically effective amount of paclitaxel once a week per cycle, wherein the treatment is given for one to four weeks per cycle. In another embodiment said FPT inhibitor is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering daily a therapeutically effective amount of the FPT inhibitor (i.e., compound of this invention), administering a therapeutically effective amount of carboplatin once every three weeks per cycle, and administering a therapeutically effective amount of paclitaxel once every three weeks per cycle, wherein the treatment is given for one to three weeks. In another embodiment said FPT inhibitor is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering about 50 to about 200 mg of the FPT inhibitor (i.e., compound of this invention) twice a day, administering carboplatin once per week per cycle in an amount to provide an AUC of about 2 to about 8 (and in another embodiment about 2 to about 3), and administering once per week per cycle about 60 to about 300 mg/m$^2$ (and in another embodiment about 50 to 100 mg/m$^2$, and in yet another embodiment about 60 to about 80 mg/m$^2$) of paclitaxel, wherein the treatment is given for one to four weeks per cycle. In another embodiment said FPT inhibitor is administered in amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

In another embodiment, this invention is directed to a method for treating non small cell lung cancer in a patient in need of such treatment comprising administering about 50 to about 200 mg of the FPT inhibitor (i.e., compound of this invention) twice a day, administering carboplatin once every three weeks per cycle in an amount to provide an AUC of about 2 to about 8 (in another embodiment about 5 to about 8, and in another embodiment 6), and administering once every three weeks per cycle about 150 to about 250 mg/m² (and in another embodiment about 175 to about 225 mg/m², and in another embodiment 175 mg/m²) of paclitaxel, wherein the treatment is given for one to three weeks. In another embodiment said FPT inhibitor is administered in an amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

Other embodiments of this invention are directed to methods of treating cancer as described in the above embodiments except that in place of paclitaxel and carboplatin the taxanes and platinum coordinator compounds used together in the methods are: (1) docetaxel (Taxotere®) and cisplatin; (2) paclitaxel and cisplatin; and (3) docetaxel and carboplatin. In another embodiment of the methods of this invention cisplatin is used in amounts of about 30 to about 100 mg/m². In the another embodiment of the methods of this invention docetaxel is used in amounts of about 30 to about 100 mg/m².

In another embodiment this invention is directed to a method of treating cancer comprising administering to a patient in need of such treatment therapeutically effective amounts of the FPT inhibitor (i.e., compound of this invention), a taxane, and an EGF inhibitor that is an antibody. In another embodiment the taxane used is paclitaxel, and the EGF inhibitor is a HER2 antibody (in one embodiment Herceptin) or Cetuximab, and in another embodiment Herceptin is used. The length of treatment, and the amounts and administration of the FPT inhibitor and the taxane are as described in the embodiments above. The EGF inhibitor that is an antibody is administered once a week per cycle, and in another embodiment is administered on the same day as the taxane, and in another embodiment is administered consecutively with the taxane. For example, Herceptin is administered in a loading dose of about 3 to about 5 mg/m² (in another embodiment about 4 mg/m²), and then is administered in a maintenance dose of about 2 mg/m² once per week per cycle for the remainder of the treatment cycle (usually the cycle is 1 to 4 weeks). In one embodiment the cancer treated is breast cancer.

In another embodiment this invention is directed to a method of treating cancer comprising administering to a patient in need of such treatment therapeutically effective amounts of: (1) the FPT inhibitor (i.e., compound of this invention), (2) a taxane, and (3) an antineoplastic agent selected from the group consisting of: (a) an EGF inhibitor that is a small molecule, (b) a VEGF inhibitor that is an antibody, and (c) a VEGF kinase inhibitor that is a small molecule. In another embodiment, the taxane paclitaxel or docetaxel is used. In another embodiment the antineoplastic agent is selected from the group consisting of: tarceva, Iressa, bevacizumab, SU5416, SU6688 and BAY 43-9006. The length of treatment, and the amounts and administration of the FPT inhibitor and the taxane are as described in the embodiments above. The VEGF kinase inhibitor that is an antibody is usually given once per week per cycle. The EGF and VEGF inhibitors that are small molecules are usually given daily per cycle. In another embodiment, the VEGF inhibitor that is an antibody is given on the same day as the taxane, and in another embodiment is administered concurrently with the taxane. In another embodiment, when the EGF inhibitor that is a small molecule or the VEGF inhibitor that is a small molecule is administered on the same day as the taxane, the administration is concurrently with the taxane. The EGF or VEGF kinase inhibitor is generally administered in an amount of about 10 to about 500 mg/m².

In another embodiment this invention is directed to a method of treating cancer comprising administering to a patient in need of such treatment therapeutically effective amounts of the FPT inhibitor (i.e., compound of this invention), an anti-tumor nucleoside derivative, and a platinum coordination compound.

Another embodiment of this invention is directed to a method of treating cancer comprising administering to a patient in need of such treatment therapeutically effective amounts of the FPT inhibitor (i.e., compound of this invention), an anti-tumor nucleoside derivative, and a platinum coordination compound, wherein said FPT inhibitor is administered every day, said anti-tumor nucleoside derivative is administered once per week per cycle, and said platinum coordinator compound is administered once per week per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of the FPT inhibitor (i.e., compound of this invention), an anti-tumor nucleoside derivative, and a platinum coordination compound, wherein said FPT inhibitor is administered every day, said an anti-tumor nucleoside derivative is administered once per week per cycle, and said platinum coordinator compound is administered once every three weeks per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of the FPT inhibitor (i.e., compound of this invention), gemcitabine, and cisplatin. In another embodiment, said FPT inhibitor is administered every day, said gemcitabine is administered once per week per cycle, and said cisplatin is administered once per week per cycle. In one embodiment the treatment is for one to seven weeks per cycle.

Another embodiment of this invention is directed to a method of treating cancer comprising administering to a patient in need of such treatment therapeutically effective amounts of the FPT inhibitor (i.e., compound of this invention), gemcitabine, and cisplatin. In another embodiment, said FPT inhibitor is administered every day, said gemcitabine is administered once per week per cycle, and said cisplatin is administered once every three weeks per cycle. In another embodiment the treatment is for one to seven weeks.

Another embodiment of this invention is directed to a method of treating cancer comprising administering to a patient in need of such treatment therapeutically effective amounts of the FPT inhibitor (i.e., compound of this invention), gemcitabine, and carboplatin. In another embodiment said FPT inhibitor is administered every day, said gemcitabine is administered once per week per cycle, and said carboplatin is administered once per week per cycle. In another embodiment the treatment is for one to seven weeks per cycle.

Another embodiment of this invention is directed to a method of treating cancer comprising administering to a patient in need of such treatment therapeutically effective amounts of the FPT inhibitor (i.e., compound of this invention), gemcitabine, and carboplatin. In another embodiment said FPT inhibitor is administered every day, said gemcitabine is administered once per week per cycle, and said carboplatin is administered once every three weeks per cycle. In another embodiment the treatment is for one to seven weeks per cycle.

In the above embodiments using gemcitabine, the FPT inhibitor (i.e., compound of this invention) and the platinum coordinator compound are administered as described above for the embodiments using taxanes. Gemcitabine is administered in an amount of about 500 to about 1250 mg/m$^2$. In one embodiment the gemcitabine is administered on the same day as the platinum coordinator compound, and in another embodiment consecutively with the platinum coordinator compound, and in another embodiment the gemcitabine is administered after the platinum coordinator compound.

Another embodiment of this invention is directed to a method of treating cancer in a patient in need of such treatment comprising administering to said patient the FPT inhibitor (i.e., compound of this invention) and an antineoplastic agent selected from: (1) EGF inhibitors that are antibodies, (2) EGF inhibitors that are small molecules, (3) VEGF inhibitors that are antibodies, and (4) VEGF kinase inhibitors that are small molecules all as described above. The treatment is for one to seven weeks per cycle, and generally for one to four weeks per cycle. The FPT inhibitor is administered in the same manner as described above for the other embodiments of this invention. The small molecule antineoplastic agents are usually administered daily, and the antibody antineoplastic agents are usually administered once per week per cycle. In one embodiment the antineoplastic agents are selected from the group consisting of: Herceptin, Cetuximab, Tarceva, Iressa, bevacizumab, IMC-1C11, SU5416, SU6688 and BAY 43-9006.

In the embodiments of this invention wherein a platinum coordinator compound is used as well as at least one other antineoplastic agent, and these drugs are administered consecutively, the platinum coordinator compound is generally administered after the other antineoplastic agents have been administered.

Other embodiments of this invention include the administration of a therapeutically effective amount of radiation to the patient in addition to the administration of the FPT inhibitor (i.e., compound of this invention) and antineoplastic agents in the embodiments described above. Radiation is administered according to techniques and protocols well know to those skilled in the art.

Another embodiment of this invention is directed to a pharmaceutical composition comprising at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising the FPT inhibitor (i.e., compound of this invention) and at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising the FPT inhibitor (i.e., compound of this invention) and at least one antineoplastic agent and a pharmaceutically acceptable carrier for intravenous administration. Preferably the pharmaceutically acceptable carrier is an isotonic saline solution (0.9% NaCl) or a dextrose solution (e.g., 5% dextrose).

Those skilled in the art will appreciate that the compounds (drugs) used in the methods of this invention are available to the skilled clinician in pharmaceutical compositions (dosage forms) from the manufacturer and are used in those compositions. So, the recitation of the compound or class of compounds in the above described methods can be replaced with a recitation of a pharmaceutical composition comprising the particular compound or class of compounds. For example, the embodiment directed to a method of treating cancer comprising administering to a patient in need of such treatment therapeutically effective amounts of the FPT inhibitor (i.e., compound of this invention), a taxane, and a platinum coordination compound, includes within its scope a method of treating cancer comprising administering to a patient in need of such treatment therapeutically effective amounts of a pharmaceutical composition comprising the FPT inhibitor, a pharmaceutical composition comprising a taxane, and a pharmaceutical composition comprising a platinum coordination compound.

The actual dosage employed may be varied depending upon the requirements of the patient and the severity of the condition being treated. Determination of the proper dosage for a particular situation is within the skill of the art.

The amount and frequency of administration of the FPT inhibitor (i.e., compound of this invention) and the antineoplastic agents will be regulated according to the judgment of the attending clinician (physician) considering such factors as age, condition and size of the patient as well as severity of the cancer being treated.

The antineoplastic agent can be administered according to therapeutic protocols well known in the art. It will be apparent to those skilled in the art that the administration of the antineoplastic agent can be varied depending on the cancer being treated and the known effects of the antineoplastic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of antineoplastic agent will depend upon the diagnosis of the attending physicians and their judgement of the condition of the patient and the appropriate treatment protocol.

The determination of the order of administration, and the number of repetitions of administration of the antineoplastic agent during a treatment protocol, is well within the knowledge of the skilled physician after evaluation of the cancer being treated and the condition of the patient.

Thus, in accordance with experience and knowledge, the practicing physician can modify each protocol for the administration of an antineoplastic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Other embodiments of this invention are directed to the use of a combination of at least one (e.g., one) compound of formula I and drugs for the treatment of breast cancer, i.e., this invention is directed to a combination therapy for the treatment of breast cancer. Those skilled in the art will appreciate that the compounds of formula I and drugs are generally administered as individual pharmaceutical compositions. The use of a pharmaceutical composition comprising more than one drug is within the scope of this invention.

Thus, another embodiment of this invention is directed to a method of treating (or preventing) breast cancer (i.e., postmenopausal and premenopausal breast cancer, e.g., hormone-dependent breast cancer) in a patient in need of such treatment comprising administering to said patient a therapeutically effective amount of at least one (e.g., one) compound of formula I and a therapeutically effective amount of at least one antihormonal agent selected from the group consisting of: (a) aromatase inhibitors, (b) antiestrogens, and (c) LHRH analogues; and said treatment optionally including the administration of at least one chemotherapeutic agent.

The compound of formula I is preferably administered orally, and in one embodiment is administered in capsule form.

Examples of aromatase inhibitors include but are not limited to: Anastrozole (e.g., Arimidex), Letrozole (e.g., Femara), Exemestane (Aromasin), Fadrozole and Formestane (e.g., Lentaron).

Examples of antiestrogens include but are not limited to: Tamoxifen (e.g., Nolvadex), Fulvestrant (e.g., Faslodex), Raloxifene (e.g., Evista), and Acolbifene.

Examples of LHRH analogues include but are not limited to: Goserelin (e.g., Zoladex) and Leuprolide (e.g., Leuprolide Acetate, such as Lupron or Lupron Depot).

Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

Preferably, when more than one antihormonal agent is used, each agent is selected from a different category of agent. For example, one agent is an aromatase inhibitor (e.g., Anastrozole, Letrozole, or Exemestane) and one agent is an antiestrogen (e.g., Tamoxifen or Fulvestrant).

Another embodiment of this invention is directed to a method of treating or preventing breast cancer in a patient in need of such treatment wherein said treatment comprises administering a therapeutically effective amount of at least one (e.g., one) compound of formula I and at least one antihormonal agent selected from the group consisting of: (a) aromatase inhibitors, (b) antiestrogens, and (c) LHRH analogues; and administering an effective amount of at least one chemotherapeutic agent.

Another embodiment of this invention is directed to a method of treating or preventing breast cancer in a patient in need of such treatment wherein said treatment comprises administering a therapeutically effective amount of at least one compound of formula I (e.g., one) and at least one antihormonal agent selected from the group consisting of: (a) aromatase inhibitors, (b) antiestrogens, and (c) LHRH analogues.

Another embodiment of this invention is directed to a method of treating or preventing breast cancer in a patient in need of such treatment wherein said treatment comprises administering a therapeutically effective amount of at least one compound of formula I (e.g., one) and at least one antihormonal agent selected from the group consisting of: (a) aromatase inhibitors, and (b) antiestrogens.

Another embodiment of this invention is directed to a method of treating or preventing breast cancer in a patient in need of such treatment wherein said treatment comprises administering a therapeutically effective amount of at least one compound of formula I (e.g., one), at least one antihormonal agent selected from the group consisting of: (a) aromatase inhibitors and (b) antiestrogens; and at least one chemotherapeutic agent.

Another embodiment of this invention is directed to a method of treating or preventing breast cancer in a patient in need of such treatment wherein said treatment comprises administering a therapeutically effective amount of at least one compound of formula I (e.g., one) and at least one aromatase inhibitor.

Another embodiment of this invention is directed to a method of treating or preventing breast cancer in a patient in need of such treatment wherein said treatment comprises administering a therapeutically effective amount of at least one compound of formula I (e.g., one), at least one aromatase inhibitor, and at least one chemotherapeutic agent.

Another embodiment of this invention is directed to a method of treating or preventing breast cancer in a patient in need of such treatment wherein said treatment comprises administering a therapeutically effective amount of: (1) at least one compound of formula I (e.g., one); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide; and administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one compound of formula formula I (e.g., one); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one compound of formula I (e.g., one); and (2) at least one antihormonal agent selected from the group consisting of: (a) aromatase inhibitors that are selected from the group consisting of Anastrozole, Letrozole, Exemestane, Fadrozole and Formestane, and (b) antiestrogens that are selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of: (1) at least one compound of formula I (e.g., one); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene; and administering an effective amount of at least one chemotherapeutic agents are selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one compound of formula I (e.g., one); and (2) at least one aromatase inhibitor selected from the group consisting of Anastrozole, Letrozole, Exemestane, Fadrozole and Formestane.

Another embodiment of this invention is directed to a method of treating or preventing breast cancer in a patient in need of such treatment wherein said treatment comprises administering a therapeutically effective amount of: (1) at least one compound of formula I (e.g., one); (2) at least one aromatase inhibitor that is selected from the group consisting of Anastrozole, Letrozole, Exemestane, Fadrozole and Formestane; and (3) administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one compound of formula I (e.g., one); (2) at least one aromatase inhibitor; and (3) at least one LHRH analogue.

Another embodiment of this invention is directed to a method of treating or preventing breast cancer in a patient in need of such treatment wherein said treatment comprises administering a therapeutically effective amount of:(1) at least one compound of formula I (e.g., one); (2) at least one antiestrogen ; and (3) at least one LHRH analogue.

Another embodiment of this invention is directed to a method of treating or preventing breast cancer in a patient in need of such treatment wherein said treatment comprises administering a therapeutically effective amount of: (1) at least one compound of formula I (e.g., one); (2) at least one aromatase inhibitor that is selected from the group consisting of Anastrozole, Letrozole, Exemestane, Fadrozole and Formestane; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one compound of formula I (e.g., one); (2) at least one antiestrogen that is selected from the group consisting of: Tamoxifen, Fulvestrant, Raloxifene, and Acolbifene; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of at least one compound of formula I (e.g., one) and Anastrozole.

Another embodiment of this invention is directed to a method of treating or preventing breast cancer in a patient in need of such treatment wherein said treatment comprises administering a therapeutically effective amount of at least one compound of formula I (e.g., one) and Letrazole.

Another embodiment of this invention is directed to a method of treating or preventing breast cancer in a patient in need of such treatment wherein said treatment comprises administering a therapeutically effective amount of at least one compound of formula I (e.g., one) and Exemestane.

Another embodiment of this invention is directed to a method of treating or preventing breast cancer in a patient in need of such treatment wherein said treatment comprises administering a therapeutically effective amount of at least one compound of formula I (e.g., one) and Fadrozole.

Another embodiment of this invention is directed to a method of treating or preventing breast cancer in a patient in need of such treatment wherein said treatment comprises administering a therapeutically effective amount of at least one compound of formula I (e.g., one) and Formestane.

Another embodiment of this invention is directed to a method of treating or preventing breast cancer in a patient in need of such treatment wherein said treatment comprises administering a therapeutically effective amount of at least one compound of formula I (e.g., one) and Tamoxifen.

Another embodiment of this invention is directed to a method of treating or preventing breast cancer in a patient in need of such treatment wherein said treatment comprises administering a therapeutically effective amount of at least one compound of formula I (e.g., one) Fulvestrant.

Another embodiment of this invention is directed to a method of treating or preventing breast cancer in a patient in need of such treatment wherein said treatment comprises administering a therapeutically effective amount of at least one compound of formula I (e.g., one) and Raloxifene.

Another embodiment of this invention is directed to a method of treating or preventing breast cancer in a patient in need of such treatment wherein said treatment comprises administering a therapeutically effective amount of at least one compound of formula I (e.g., one) and Acolbifene.

Another embodiment of this invention is directed to a method of treating or preventing breast cancer in a patient in need of such treatment wherein said treatment comprises administering a therapeutically effective amount of at least one compound of formula I (e.g., one) and Goserelin.

Another embodiment of this invention is directed to a method of treating or preventing breast cancer in a patient in need of such treatment wherein said treatment comprises administering a therapeutically effective amount of at least one compound of formula I (e.g., one) and Leuprolide.

Another embodiment of this invention is directed to a method of treating or preventing breast cancer in a patient in need of such treatment wherein said treatment comprises administering a therapeutically effective amount of at least one compound of formula I (e.g., one), Anastrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula I (e.g., one), Letrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula I (e.g., one), Exemestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula I (e.g., one), Fadrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula I (e.g., one), Formestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one compound of formula I (e.g., one), Anastrozole, and Tamoxifen.

Another embodiment of this invention is directed to a method of treating or preventing breast cancer in a patient in need of such treatment wherein said treatment comprises administering a therapeutically effective amount of at least one compound of formula I (e.g., one), Letrozole, and Tamoxifen.

Another embodiment of this invention is directed to a method of treating or preventing breast cancer in a patient in need of such treatment wherein said treatment comprises administering a therapeutically effective amount of at least one compound of formula I (e.g., one), Exemestane, and Tamoxifen.

Another embodiment of this invention is directed to a method of treating or preventing breast cancer in a patient in need of such treatment wherein said treatment comprises administering a therapeutically effective amount of at least one compound of formula I (e.g., one), Fadrozole, and Tamoxifen.

Another embodiment of this invention is directed to a method of treating or preventing breast cancer in a patient in need of such treatment wherein said treatment comprises administering a therapeutically effective amount of at least one compound of formula I (e.g., one), Formestane, and Tamoxifen.

Another embodiment of this invention is directed to a method of treating or preventing breast cancer in a patient in need of such treatment wherein said treatment comprises administering a therapeutically effective amount of at least one compound of formula I (e.g., one), Anastrozole, and Fulvestrant.

Another embodiment of this invention is directed to a method of treating or preventing breast cancer in a patient in need of such treatment wherein said treatment comprises administering a therapeutically effective amount of at least one compound of formula I (e.g., one), Letrozole, and Fulvestrant.

Another embodiment of this invention is directed to a method of treating or preventing breast cancer in a patient in need of such treatment wherein said treatment comprises administering a therapeutically effective amount of at least one compound of formula I (e.g., one), Exemestane, and Fulvestrant.

Another embodiment of this invention is directed to a method of treating or preventing breast cancer in a patient in need of such treatment wherein said treatment comprises administering a therapeutically effective amount of at least one compound of formula I (e.g., one), Fadrozole, and Fulvestrant.

Another embodiment of this invention is directed to a method of treating or preventing breast cancer in a patient in need of such treatment wherein said treatment comprises administering a therapeutically effective amount of at least one compound of formula I (e.g., one), Formestane, and Fulvestrant.

Another embodiment of this invention is directed to a method of treating or preventing breast cancer in a patient in need of such treatment wherein said treatment comprises administering a therapeutically effective amount of at least one compound of formula I (e.g., one), Anastrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Letrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Exemestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Fadrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Formestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Raloxifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Goserelin, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Leuprolein, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Anastrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Letrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Exemestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Fadrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Formestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Anastrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Letrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Exemestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Fadrozole, Tamoxifen, and a chemotherapeutic agent selected from the. group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Formestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Anastrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Letrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Exemestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Fadrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Formestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one compound of formula I (e.g., one), Goserelin and Tamoxifen.

Another embodiment of this invention is directed to a method of treating or preventing breast cancer in a patient in need of such treatment wherein said treatment comprises administering a therapeutically effective amount of at least one compound of formula I (e.g., one), Goserelin, and Fulvestrant.

Another embodiment of this invention is directed to a method of treating or preventing breast cancer in a patient in need of such treatment wherein said treatment comprises administering a therapeutically effective amount of at least one compound of formula I (e.g., one), Goserelin, and Raloxifene.

Another embodiment of this invention is directed to a method of treating or preventing breast cancer in a patient in need of such treatment wherein said treatment comprises administering a therapeutically effective amount of at least one compound of formula I (e.g., one), Goserelin and Acolbifene.

Another embodiment of this invention is directed to a method of treating or preventing breast cancer in a patient in need of such treatment wherein said treatment comprises administering a therapeutically effective amount of at least one compound of formula I (e.g., one), Leuprolide, and Tamoxifen.

Another embodiment of this invention is directed to a method of treating or preventing breast cancer in a patient in need of such treatment wherein said treatment comprises administering a therapeutically effective amount of at least one compound of formula I (e.g., one), Leuprolide, and Fulvestrant.

Another embodiment of this invention is directed to a method of treating or preventing breast cancer in a patient in need of such treatment wherein said treatment comprises administering a therapeutically effective amount of at least one compound of formula I (e.g., one), Leuprolide, and Raloxifene.

Another embodiment of this invention is directed to a method of treating or preventing breast cancer in a patient in need of such treatment wherein said treatment comprises administering a therapeutically effective amount of at least one compound of formula I (e.g., one), Leuprolide and Acolbifene.

Another embodiment of this invention is directed to a method of treating or preventing breast cancer in a patient in need of such treatment wherein said treatment comprises administering a therapeutically effective amount of at least one compound of formula I (e.g., one), Goserelin and Anastrozole.

Another embodiment of this invention is directed to a method of treating or preventing breast cancer in a patient in need of such treatment wherein said treatment comprises administering a therapeutically effective amount of at least one compound of formula I (e.g., one), Goserelin and Letrozole.

Another embodiment of this invention is directed to a method of treating or preventing breast cancer in a patient in need of such treatment wherein said treatment comprises administering a therapeutically effective amount of at least one compound of formula I (e.g., one), Goserelin and Exemestane.

Another embodiment of this invention is directed to a method of treating or preventing breast cancer in a patient in need of such treatment wherein said treatment comprises administering a therapeutically effective amount of at least one compound of formula I (e.g., one), Goserelin and Fadrozole.

Another embodiment of this invention is directed to a method of treating or preventing breast cancer in a patient in need of such treatment wherein said treatment comprises administering a therapeutically effective amount of at least one compound of formula I (e.g., one), Goserelin and Formestane.

Another embodiment of this invention is directed to a method of treating or preventing breast cancer in a patient in need of such treatment wherein said treatment comprises administering a therapeutically effective amount of at least one compound of formula I (e.g., one), Leuprolide and Anastrozole.

Another embodiment of this invention is directed to a method of treating or preventing breast cancer in a patient in need of such treatment wherein said treatment comprises administering a therapeutically effective amount of at least one compound of formula I (e.g., one), Leuprolide and Letrozole.

Another embodiment of this invention is directed to a method of treating or preventing breast cancer in a patient in need of such treatment wherein said treatment comprises administering a therapeutically effective amount of at least one compound of formula I (e.g., one), Leuprolide and Exemestane.

Another embodiment of this invention is directed to a method of treating or preventing breast cancer in a patient in need of such treatment wherein said treatment comprises administering a therapeutically effective amount of at least one compound of formula I (e.g., one), Leuprolide and Fadrozole.

Another embodiment of this invention is directed to a method of treating or preventing breast cancer in a patient in need of such treatment wherein said treatment comprises administering a therapeutically effective amount of at least one compound of formula I (e.g., one), Leuprolide and Formestane.

Another embodiment of this invention is directed to the treatment or prevention of breast cancer in a patient in need of such treatment, said treatment comprising the administration of a therapeutically effective amount of at least one compound of formula I (e.g., one) and Anastrozole.

Another embodiment of this invention is directed to the treatment or prevention of breast cancer in a patient in need of such treatment, said treatment comprising the administration of a therapeutically effective amount of at least one compound of formula I (e.g., one) and Letrozole.

Another embodiment of this invention is directed to the treatment or prevention of breast cancer in a patient in need of such treatment, said treatment comprising the administration of a therapeutically effective amount of at least one compound of formula I (e.g., one) and Exemestane.

Another embodiment of this invention is directed to the treatment or prevention of breast cancer in a patient in need of such treatment, said treatment comprising the administration of a therapeutically effective amount of at least one compound of formula I (e.g., one) and Tamoxifen.

Another embodiment of this invention is directed to the treatment or prevention of breast cancer in a patient in need of such treatment, said treatment comprising the administration of a therapeutically effective amount of at least one compound of formula I (e.g., one) and Fulvestrant.

Another embodiment of this invention is directed to the treatment or prevention of breast cancer in a patient in need of such treatment, said treatment comprising the administration of a therapeutically effective amount of at least one compound of formula I (e.g., one), Anastrozole, and Fulvestrant.

Another embodiment of this invention is directed to the treatment or prevention of breast cancer in a patient in need of such treatment, said treatment comprising the administration of a therapeutically effective amount of at least one compound of formula I (e.g., one), Letrozole, and Fulvestrant.

Another embodiment of this invention is directed to the treatment or prevention of breast cancer in a patient in need of such treatment, said treatment comprising the administration of a therapeutically effective amount of at least one compound of formula I (e.g., one), Exemestane, and Fulvestrant.

Another embodiment of this invention is directed to the treatment or prevention of breast cancer in a patient in need of such treatment, said treatment comprising the administration of a therapeutically effective amount of at least one compound of formula I (e.g., one), Anastrozole, and Tamoxifen.

Another embodiment of this invention is directed to the treatment or prevention of breast cancer in a patient in need of such treatment, said treatment comprising the administration of a therapeutically effective amount of at least one compound of formula I (e.g., one), Letrozole, and Tamoxifen.

Another embodiment of this invention is directed to the treatment or prevention of breast cancer in a patient in need of such treatment, said treatment comprising the administration of a therapeutically effective amount of at least one compound of formula I (e.g., one), Exemestane, and Tamoxifen.

Other embodiments of this invention are directed to any of the above described embodiments for the treatment of Breast Cancer wherein the chemotherapeutic agent is Trastuzumab.

Other embodiments of this invention are directed to any of the above described embodiments for the treatment of Breast Cancer wherein the method is directed to a method of treating breast cancer.

The compound of formula I, antihormonal agents and chemotherapeutic agents can be administered concurrently or sequentially.

The antihormonal agents and optional chemotherapeutic agents are administered according to their protocols, dosage amounts, and dosage forms that are well know to those skilled in the art (e.g., the Physician's Desk Reference or published literature). For example, for Tamoxifen, Fulvestrant, Raloxifene, Anastrozole, Letrozole, Exemestane, Leuprolide and Goserelin, see the Physician's Desk Reference, $57^{th}$ Edition, 2003, published by Thomas PDR at Montvale, N.J. 07645-1742, the disclosure of which is incorporated herein by reference thereto.

In general, in the embodiments directed to the methods of treating Breast Cancer: (1) the compound of formula I can be administered daily (e.g., once per day, and in one embodiment twice a day), (2) the aromatase inhibitors can be administered in accordance with the known protocol for the aromatase inhibitor used (e.g., once per day), (3) the antiestrogens can be administered in accordance with the known protocol for the antiestrogen used (e.g., from once a day to once a month), (4) the LHRH analogue can be administered in accordance with the known protocol for the LHRH analogue used (e.g., once a month to once every three months), and (5) the chemotherapeutic agent can be administered in accordance with the known protocol for the chemotherapeutic agent used (e.g., from once a day to once a week).

Radiation therapy, if administered, is generally administered according to known protocols before administration of the compound of formula I, antihormonal agents and optional chemotherapeutic agents.

Treatment according to the methods of treating Breast Cancer is continuous (i.e., a continuous dosing schedule is followed). The treatment is continued until there is a complete response, or until the skilled clinician determines that the patient is not benefiting from the treatment (for example, when there is disease progression).

The continuous treatment protocol for Breast Cancer can be changed to a discontinuous treatment schedule if, in the judgment of the skilled clinician, the patient would benefit from a discontinuous treatment schedule with one or more of the administered drugs. For example, the compound of formula I can be given using a discontinuous treatment schedule while the remaining drugs used in the treatment are given as described herein. An example of a discontinuous treatment protocol for the compound of formula I is a repeating cycle of three weeks with the compound of formula I followed by one week without the compound of formula I.

After a complete response is achieved with the Breast Cancer treatment, maintenance therapy with the compound of formula I can be continued using the dosing described in the methods of this invention. Maintenance therapy can also include administration of the antihormonal agents using the dosing described in the methods of this invention. Maintenance therapy can just be with the antihormonal agents. For example, after a complete response is achieved, an aromatase inhibitor (e.g., Anastrozole, Letrozole or Exemestane) can be continued for up to five years. Or, for example, an antiestrogen, e.g., Tamoxifen, may be used for up to five years after a complete response is achieved. Or, for example, an antiestrogen (e.g., Tamoxifen) can be used for up to five years after a complete response is achieved followed by the use of an aromatase inhibitor (e.g., Anastrozole, Letrozole or Exemestane) for up to five years.

In the embodiments directed to the treatment of Breast Cancer described above, the compound of formula I is administered continuously in a total daily dose of about 100 mg to about 600 mg. Usually this amount is administered in divided doses, and in one embodiment this amount is administered twice a day. In one embodiment the compound of formula I is dosed twice a day in an amount of about 50 mg to about 300 mg per dose. In another embodiment the compound of formula I is dosed twice a day in an amount of about 100 mg to about 200 mg per dose. Examples include the compound of formula I being dosed twice a day at 100 mg per dose. Examples also include the compound of formula I being dosed twice a day at 200 mg per dose.

Anastrozole is administered p.o. and is dosed once a day in amounts of about 0.5 to about 10 mg per dose, and in one embodiment in an amount of about 1.0 mg per dose.

Letrozole is administered p.o. and is dosed once a day in amounts of about 1.0 to about 10 mg per dose, and in one embodiment in an amount of about 2.5 mg per dose.

Exemestane is administered p.o. and is dosed once a day in amounts of about 10 to about 50 mg per dose, and in one embodiment in an amount of about 25 mg per dose.

Fadrozole is administered p.o. and is dosed twice a day in amounts of about 0.5 to about 10 mg per dose, and in one embodiment in an amount of about 2.0 mg per dose.

Formestane is administered i.m. and is dosed once every two weeks in amounts of about 100 to about 500 mg per dose, and in one embodiment in an amount of about 250 mg per dose.

Tamoxifen is administered p.o. and is dosed once a day in amounts of about 10 to about 100 mg per dose, and in one embodiment in an amount of about 20 mg per dose.

Fulvestrant is administered i.m. and is dosed once a month in amounts of about 100 to about 1000 mg per dose, and in one embodiment in an amount of about 250 mg per dose.

Raloxifene is administered p.o. and is dosed once a day in amounts of about 10 to about 120 mg per dose, and in one embodiment in an amount of about 60 mg per dose.

Acolbifene is administered p.o. and is dosed once a day in amounts of about 5 to about 20 mg per dose, and in one embodiment in an amount of about 20 mg per dose.

Goserelin is administered s.c. and is dosed once a month, or once every three months, in amounts of about 2 to about 20 mg per dose, and in one embodiment in an amount of about 3.6 mg per dose when administered once a month, and in another embodiment in an amount of about 10.8 mg per dose when administered once every three months.

Leuprolide is administered s.c. and is dosed once a month, or once every three months, in amounts of about 2 to about 20 mg per dose, and in one embodiment in an amount of about 3.75 mg per dose when administered once a month, and in another embodiment in an amount of about 11.25 mg per dose when administered once every three months.

Trastuzumab is administered by i.v. and is dosed once a week in amounts of about 2 to about 20 mpk per dose, and in one embodiment in an amount of about 2 mpk per dose. Trastuzumab is generally initially administered in a loading dose that is generally twice the dose of the weekly dose. Thus, for example, a 4 mpk loading dose is administered and then dosing is 2 mpk per dose per week.

Gefitinib is administered p.o. and is dosed once a day in amounts of about 100 to about 1000 mg per dose, and in one embodiment in an amount of about 250 mg per dose.

Erlotinib is administered p.o. and is dosed once a day in amounts of about 100 to about 500 mg per dose, and in one embodiment in an amount of about 150 mg per dose.

Bevacizumab is administered i.v. and is dosed once every two weeks in amounts of about 2.5 to about 15 mg per kilogram of body weight per dose, and in one embodiment in an amount of about 10 mg per kilogram per dose.

Cetuximab is administered i.v. and is dosed once a week in amounts of about 200 to about 500 mg per meter squared dose, and in one embodiment in an amount of about 250 mg per meter squared per dose.

Bortezomib is administered i.v. and is dosed twice a week for 2 weeks followed by a 10 day rest period (21 day treatment cycle) for a maximum of 8 treatment cycles in amounts of about 1.0 to about 2.5 mg per meter squared per dose, and in one embodiment in an amount of about 1.3 mg per meter squared per dose.

Thus in one embodiment of this invention breast cancer is treated (or prevented) in a patient in need of such treatment wherein said treatment comprises administering to said patient: (1) the compound of formula I orally in an amount of about 50 mg to about 300 mg per dose wherein each dose is administered twice a day, and (2) Anastrozole p.o. in an amount of about 0.5 to about 10 mg per dose wherein each dose is given once a day.

In another embodiment of this invention breast cancer is treated (or prevented) in a patient in need of such treatment wherein said treatment comprises administering to said patient: (1) the compound of formula I orally in an amount of about 100 to 200 mg per dose, wherein each dose is administered twice a day, and (2) Anastrozole in an amount of about 1.0 mg per dose wherein each dose is given once a day.

In another embodiment of this invention breast cancer is treated (or prevented) in a patient in need of such treatment wherein said treatment comprises administering to said patient: (1) the compound of formula I orally in an amount of about 50 mg to about 300 mg per dose wherein each dose is administered twice a day, and (2) Letrozole p.o. in an amount of about 1.0 to about 10 mg per dose wherein each dose is given once a day.

In another embodiment of this invention breast cancer is treated (or prevented) in a patient in need of such treatment wherein said treatment comprises administering to said patient: (1) the compound of formula I in an amount of about 100 to 200 mg per dose, wherein each dose is administered twice a day, and (2) Letrozole p.o. in an amount of about 2.5 mg per dose wherein each dose is given once a day.

In another embodiment of this invention breast cancer is treated (or prevented) in a patient in need of such treatment wherein said treatment comprises administering to said patient: (1) the compound of formula I orally in an amount of about 50 mg to about 300 mg per dose wherein each dose is administered twice a day, and (2) Exemestane p.o. in an amount of about 10 to about 50 mg per dose wherein each dose is given once a day.

In another embodiment of this invention breast cancer is treated (or prevented) in a patient in need of such treatment wherein said treatment comprises administering to said patient: (1) the compound of formula I in an amount of about 100 to 200 mg per dose, wherein each dose is administered twice a day, and (2) Exemestane in an amount of about 25 mg per dose wherein each dose is given once a day.

In another embodiment of this invention breast cancer is treated (or prevented) in a patient in need of such treatment wherein said treatment comprises administering to said patient: (1) the compound of formula I orally in an amount of about 50 mg to about 300 mg per dose wherein each dose is administered twice a day, and (2) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula I orally in an amount of about 100 to 200 mg per dose, wherein each dose is administered twice a day, and (2) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula I p.o. in an amount of about 50 mg to about 300 mg per dose wherein each dose is administered twice a day, and (2) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula I p.o. in an amount of about 100 to 200 mg per dose, wherein each dose is administered twice a day, and (2) Tamoxifen p.o. in an amount of about 20 mg per dose wherein each dose is given once a day.

In other embodiments of the invention breast cancer is treated in a patient in need of such treatment wherein said treatment comprises the administration of the compound of formula I, one of the aromatase inhibitors (e.g., Anastrozole, Letrozole, or Exemestane, and in one embodiment Anastrozole), and one of the antiestrogens (e.g., Fulvestrant or Tamoxifen), wherein the compound of formula I, aromatase inhibitor and antiestrogen are administered in the dosages described above.

Thus, for example in another embodiment of this invention breast cancer is treated (or prevented) in a patient in need of such treatment wherein said treatment comprises administering to said patient: (1) the compound of formula I p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula I p.o in an amount of about 100 to 200 mg per dose, wherein each dose is administered twice a day, (2) Anastrozole p.o. in an amount of about 1.0 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula I p.o. in an amount of about 50 mg to about 300 mg per-dose wherein each dose is administered twice a day, (2) Letrozole p.o in an amount of about 1.0 to about 10 mg per dose wherein each dose is given once a day, and (3) Fulvestrant in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula I p.o. in an amount of about 100 to 200 mg per dose, wherein each dose is administered twice a day, (2) Letrozole p.o. in an amount of about 2.5 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula I p.o. in an amount of about 50 mg to about 300 mg per dose wherein each dose is administered twice a day, (2) Exemestane p.o. in an amount of about 10 to about 50 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula I p.o. in an amount of about 100 to 200 mg per dose, wherein each dose is administered twice a day, (2) Exemestane p.o. in an amount of about 25 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula I p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Tamoxifen p.o.in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula I p.o. in an amount of about 100 to 200 mg per dose, wherein each dose is administered twice a day, (2) Anastrozole p.o. in an amount of about 1.0 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula I p.o. in an amount of about 50 mg to about 300 mg per dose wherein each dose is administered twice a day, (2) Letrozole p.o. in an amount of about 1.0 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula I p.o. in an amount of about 100 to 200 mg per dose, wherein each dose is administered twice a day, (2) Letrozole p.o. in an amount of about 2.5 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula I p.o. in an amount of about 50 mg to about 300 mg per dose wherein each dose is administered twice a day, (2) Exemestane p.o. in an amount of about 10 to about 50 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula I p.o. in an amount of about 100 to 200 mg per dose, wherein each dose is administered twice a day, (2) Exemestane p.o. in an amount of about 25 mg per dose wherein each dose is given once a day, and (3) Tamoxifen p.o. in an amount of about 20 mg per dose wherein each dose is given once a day.

Those skilled in the art will appreciate that when other combinations of antihormonal agents are used, the individual antihormonal agent is used in the amounts specified above for that individual antihormonal agent.

Other embodiments of the treatment of Breast Cancer are directed to the methods of treating Breast Cancer described above wherein the compound of formula I is dosed twice a day in an amount of about 100 mg per dose.

Other embodiments of the treatment of Breast Cancer are directed to the methods of treating Breast Cancer described above wherein the compound of formula I is dosed twice a day in an amount of about 200 mg per dose.

Other embodiments of the treatment of Breast Cancer are directed to the methods of treating Breast Cancer described above wherein a chemotherapeutic agent is administered in addition to the compound of formula I and antihormonal agent (or antihormonal agents). In these embodiments the dosage ranges of the compound of formula I and antihormonal agents are as those described above in the combination therapies, or those described above for the individual compound of formula I and antihormonal agents, and the dosages of the chemotherapeutic agents are those described above for the individual chemotherapeutic agent. The dosages for the chemotherapeutic agents are well known in the art.

Other embodiments of this invention are directed to pharmaceutical compositions comprising the compound of formula I and at least one antihormonal agent and a pharmaceutically acceptable carrier.

Other embodiments of this invention are directed to pharmaceutical compositions comprising the compound of formula I, at least one antihormonal agent, at least one chemotherapeutic agent, and a pharmaceutically acceptable carrier.

Other embodiments of this invention are directed to pharmaceutical compositions comprising the compound of formula I, at least one chemotherapeutic agent, and a pharmaceutically acceptable carrier.

Those skilled in the art will recognize that the actual dosages and protocols for administration employed in the methods of this invention may be varied according to the judgment of the skilled clinician. A determination to vary the dosages and protocols for administration may be made after the skilled clinician takes into account such factors as the patient's age, condition and size, as well as the severity of the cancer being treated and the response of the patient to the treatment.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Chemotherapeutic Agents

Classes of compounds that can be used as chemotherapeutic agents (antineoplastic agentimicrotubule affecting agents) include but are not limited to: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), paclitaxel derivatives (e.g. taxotere), Mithramycin, Deoxycoformycin, Mitomycin-C, L-Asparaginase, Interferons (especially IFN-a), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Other chemotherapeutics include Navelbene, CPT-11, Anastrazole, Letrazole, Capecitabinbe, Reloxafine, and Droloxafine.

In one embodiment the antineoplastic agents selected from Cyclophasphamide, 5-Fluorouracil, Temozolomide, Vincristine, Cisplatin, Carboplatin, and Gemcitabine. In another embodiment, the antineoplastic agent is selected from Gemcitabine, Cisplatin and Carboplatin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742); the disclosures of which is incorporated herein by reference thereto.

Microtubule Affecting Agents

As used herein, a microtubule affecting agent (e.g., paclitaxel, a paclitaxel derivative or a paclitaxel-like compound) is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), paclitaxel derivatives (e.g., Taxotere, NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055-3064; Panda (1997) Proc. Natl. Acad. Sci. USA 94:10560-10564; Muhiradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

In one embodiment the agents are compounds with paclitaxel-like activity. These include, but are not limited to paclitaxel and paclitaxel derivatives (paclitaxel-like compounds) and analogues. Paclitaxel and its derivatives (e.g. Taxol and Taxotere) are available commercially. In addition, methods of making paclitaxel and paclitaxel derivatives and analogues are well known to those of skill in the art (see, e.g., U.S. Pat. Nos: 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz (1992) Trends Pharmacol. Sci. 13: 134-146, Rowinsky (1990) J. Natl. Canc. Inst. 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. For example, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) J. Molec. Biol., 89: 737-758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (cited above).

The compounds of this invention can be used according to the methods described in U.S. application Ser. No. 10/303259 filed Nov. 25, 2002, and WO 03/047697 published Jun. 12, 2003, the disclosures of each being incorporated herein by reference thereto.

Compounds of this invention are exemplified in the following examples, which should not be construed as limiting the scope of the disclosure. Alternative mechanistic pathways and analogous structures within the scope of the invention may be apparent to those skilled in the art.

The compounds of the invention can be made following the reaction schemes below, and using procedures known in the art, for example, see WO 02/18368 published Mar. 7, 2002, and U.S. Pat. No. 5,874,442, the disclosures of each being incorporated herein by reference thereto.

Scheme 1A
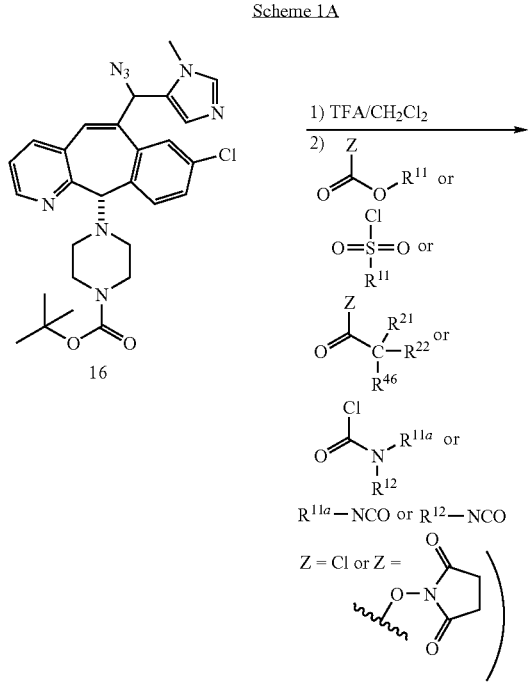
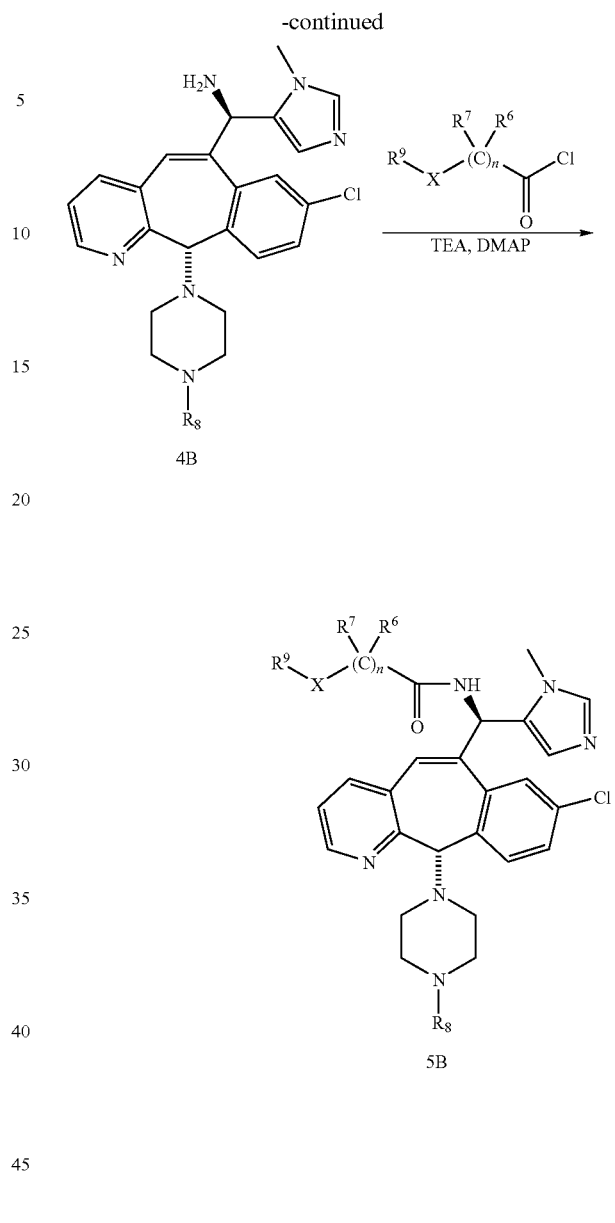
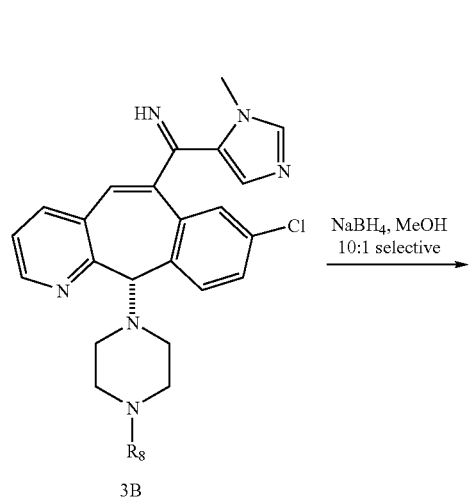
Scheme 2A
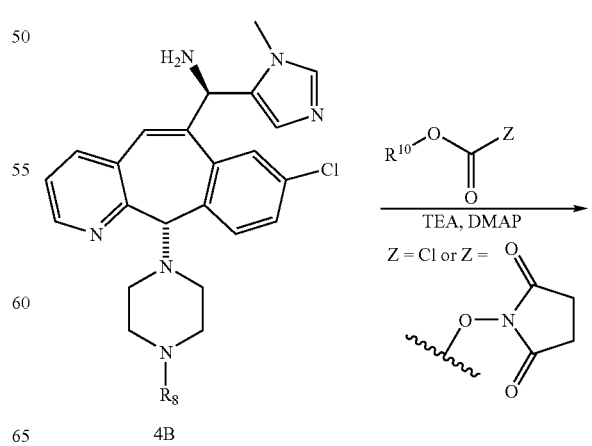

117 118
-continued    -continued
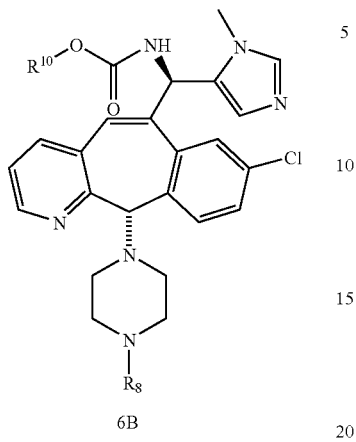
6B
EXAMPLE 1
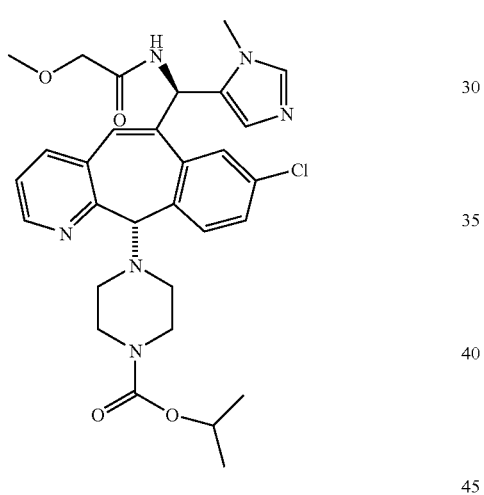
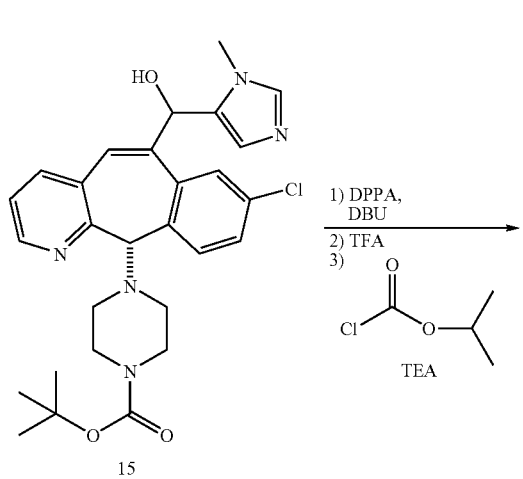
15
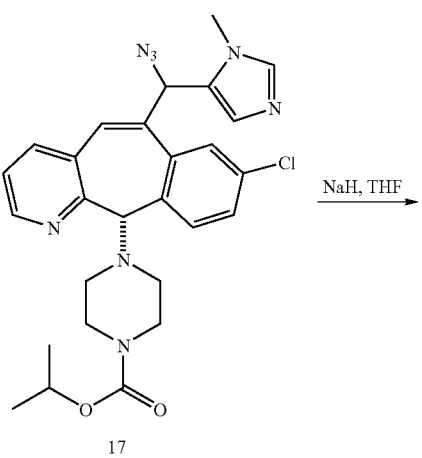
17
Scheme 1
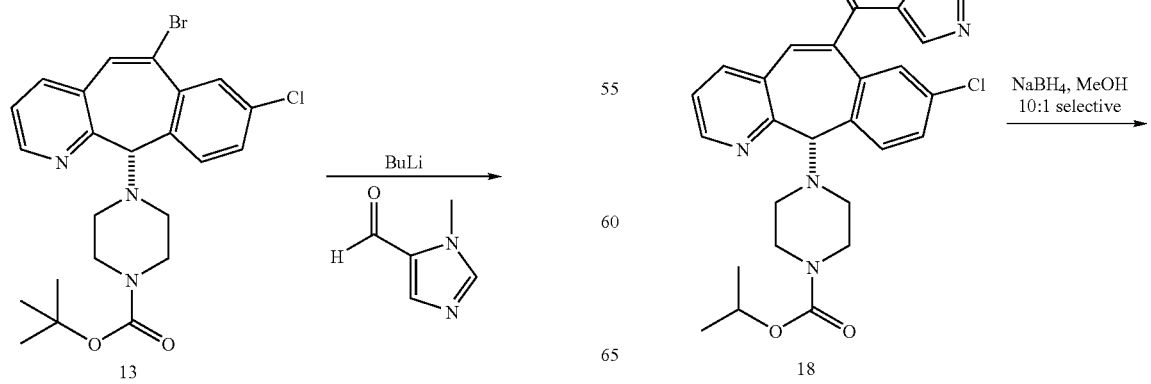

-continued

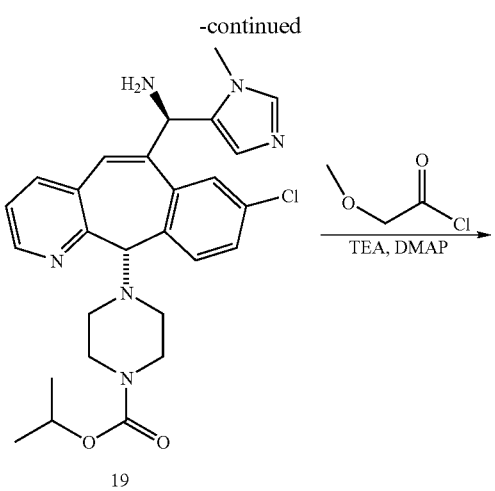

Step B

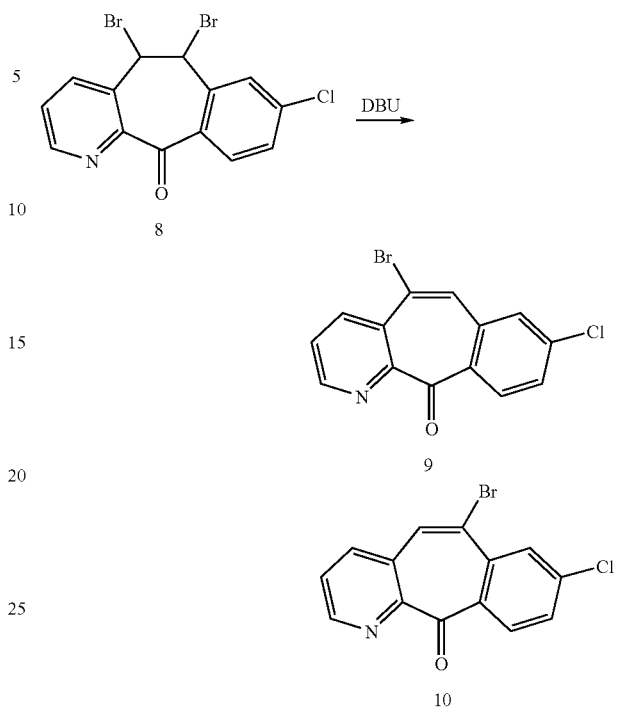

The dibromo compound (8) from Step A (35.72 g; 88.97 mmol) above was dissolved in CH$_2$Cl$_2$ (1.5 L) and cooled to 0° C. Dropwise, DBU (15.96 ml) was added and the suspension stirred for 3 hr. The reaction mixture was concentrated redissolved in CH$_2$Cl$_2$ (1.5 L) filtered through a bed of silica gel and rinsed with 5% EtOAc/CH$_2$Cl$_2$ (4 L). The combined rinses were concentrated and purified by flash silica gel column chromatography into pure 5 (compound 9) and 6 (compound 10) mono-bromo substituted compounds eluting with 10-30% EtOAc/Hex then 3% EtOAc/CH$_2$Cl$_2$.

Step C

Step A

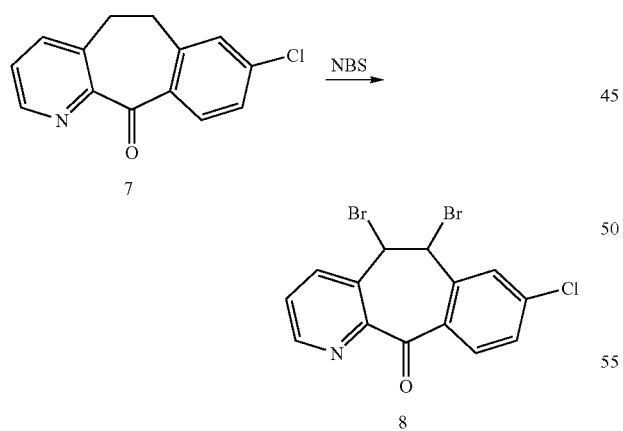

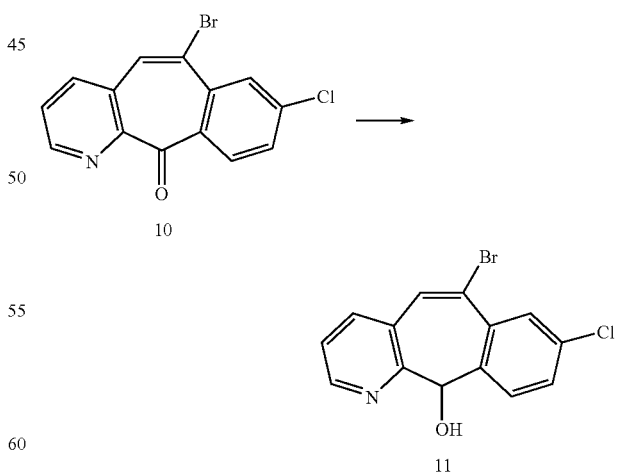

The tricyclic keto-compound (disclosed in U.S. Pat. No. 5,151,423) (30.0 g; 123.2 mmol) was combined with NBS (48.2 g; 271.0 mmol) and benzoyl peroxide (0.42 g) in CCl$_4$ (210 ml). The reaction was heated to 80° C. for 10 hr. The mixture was cooled and let stand for 8 hr. The resulting precipitate was filtered. Added MeOH (200 ml) and stirred the mixture over 2 days. The solid was filtered and dried under vacuum to a constant weight to obtain compound 8.

To a stirred solution of the mono-bromo compound (10) from step B (10.0 g, 35.07 mmol) in MeOH (200 ml) under nitrogen at 0° C. was added NaBH$_4$ (1.94 g, 51.2 mmol). The resulting solution was stirred at 0° C. for 1.5 hours, then evaporated, followed by extraction with CH$_2$Cl$_2$—H$_2$O. The combined organic layer was dried over MgSO$_4$, filtered, and evaporated to dryness to give a white solid (11) (10.3 g, 100%, M=287).

Step D

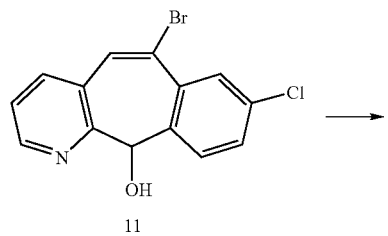

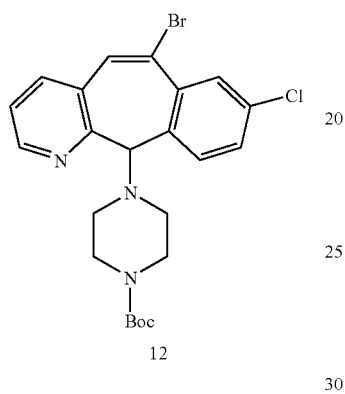

To a stirred solution of the alcohol (11) from Step C (10.0 g, 34.8 mmol) in CH$_2$Cl$_2$ (200 ml) at 0° C. was added 2,6-lutidine (14.9 g, 139.3 mmol) and thionyl chloride (8.28 g, 69.66 mmol). The resulting solution was warmed to room temperature and stirred overnight. The solution was then poured onto 0.5N NaOH solution, followed by extraction with CH$_2$Cl$_2$. The combined aqueous layer was dried over Na$_2$SO$_4$, filtered, and concentrated to dryness to give a crude brown oil (15.5 g). To a solution of this crude oil (15.5 g) in acetonitrile (200 ml) was added 2,6-Bis (dimethyl)-1-methyl piperidine (10.81 g, 69.66 mmol) and N-Boc piperidine (6.49 g, 34.83 mmol). The resulting mixture was warmed to 65° C. overnight. The mixture was evaporated to dryness, followed by extraction with CH$_2$Cl$_2$/saturated NaHCO$_3$. The combined organic layer was dried over Na$_2$SO$_4$, concentrated and purified by column chromatography on silica gel, eluting with 5% EtOAc/95% Hexane to give the protected N-Boc compound (12) (5.68 g, 36% yield, MH$^+$=455).

Step E

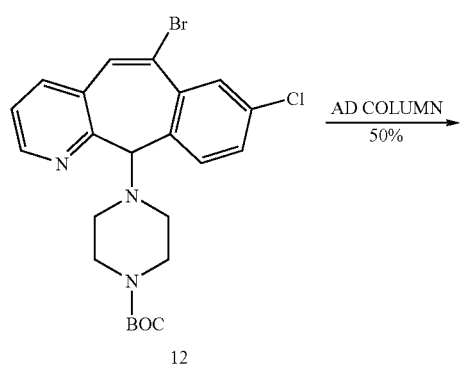

-continued

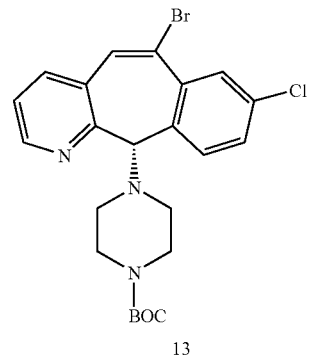

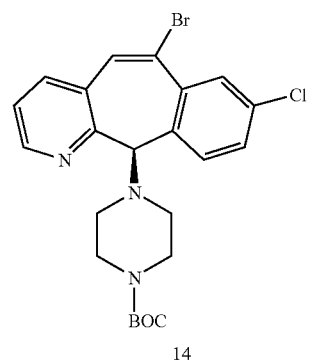

Separations of enantiomers 13 and 14 is accomplished by chiral HPLC using a Chiralpak AD column and eluting with IPA (20%) hexanes (80%)+0.2% DEA.

Isomer 13: retention time=7.65 min; MH$^+$=492.

Isomer 14: retention time=12.16 min; MH$^+$=492, m.p. 95-100° C.

Step F

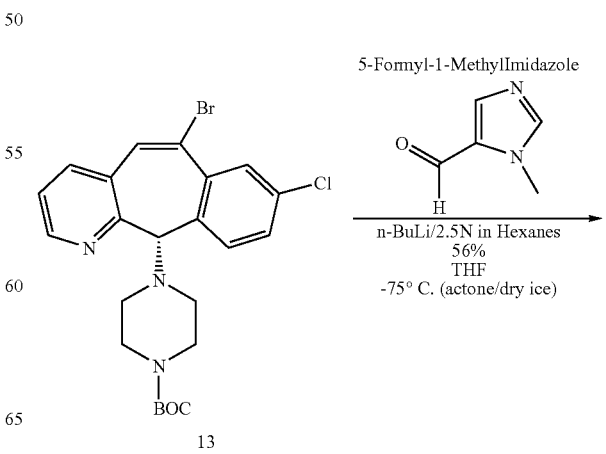

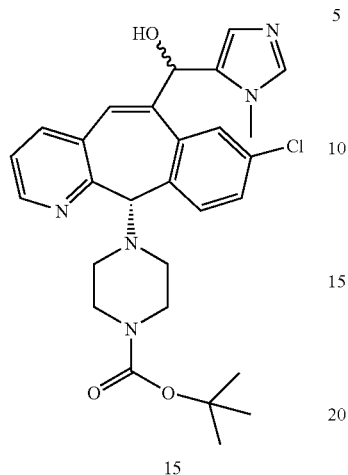

15

13 (0.9 g, 1.83 mmol) was dissolved in dry THF (15 ml) and cooled to −75° C. (dry ice/acetone bath). N-BuLi (2.5N in Hexanes); 1.5 ml, 3.74 mmol), was added dropwise at −75° C. and stirred for ~20 minutes. 5-Formyl-1-Methyl Imidazole (0.3 g, 2.75 mmol in 2 ml THF was added quickly and stirred at −75° C. for 3 hours. Worked up by adding 10 ml of H$_2$O and extracted with Ethyl Acetate and washed with brine, dried over MgSO$_4$, filtered and evaporated to give crude product. Crude was purified by Flash Chromatography (silica gel column) using CH$_2$Cl$_2$/5% CH$_3$OH (15% NH$_4$OH) to give 0.54 g of compound 15, 56% yield.

Step G

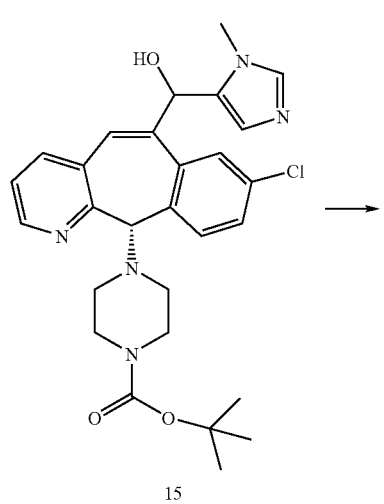

15

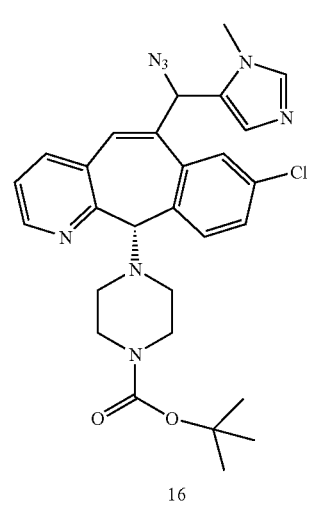

16

To a toluene solution (100 mL) of (15) (6.2 g, 11.9 mmol) at room temperature was added DPPA (8.5 g, 30.9 mmol) followed by addition of DBU (6.5 mL, 43.5 mmol). The mixture was stirred for 4 hours and then diluted with ethyl acetate (300 mL), washed with water twice and brine once. The organic layer was dried and the solvent was evaporated. The residue was purified by gradient column (1% to 10% MeOH in CH$_2$Cl$_2$) to give product (16) (5.6 g, MH+547.1).

Step H

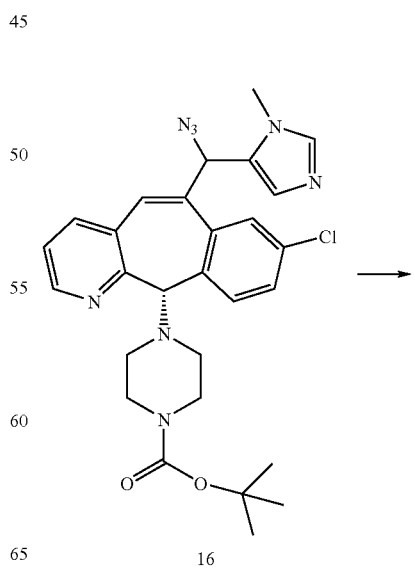

16

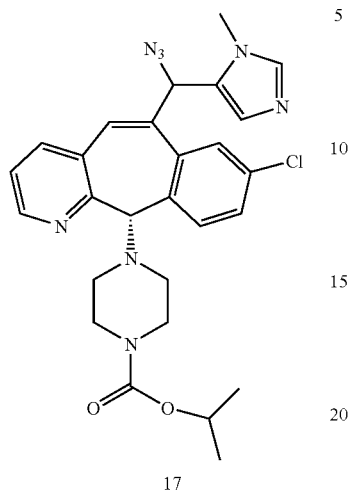

17

To a solution of 16 (13.26 gm, 24.7 mmol) in 88 ml of dichloromethane was added 24 ml of trifluoroacetic acid. The reaction mixture was stirred for 3 hours, evaporated to dryness followed by evaporation from toluene. The crude product was dissolved in 19 ml of pyridine and 137 ml of dichloromethane. Isopropylchloroformate (29 ml of a 1 N solution in dichloromethane) was added and the reaction mixture stirred for 1 hour. The reaction mixture was added to brine, extracted three times with ethylacetate, dried over magnesium sulfate, filtered and evaporated to obtain 14.66 gm of compound 17 (MH+=533).

Step I

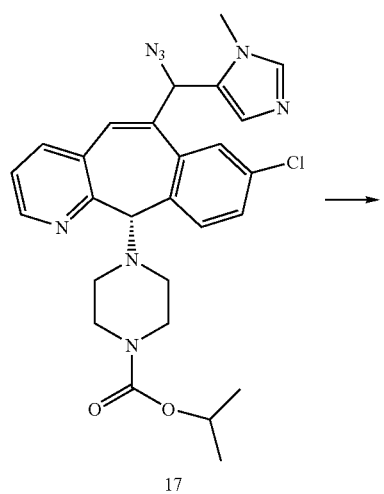

17

To a solution of 17 (24.7 mmol) in 230 ml of tetrahydrofuran was added sodium hydride (60% oil dispersion, 1.5 gm, 39.9 mmol). The reaction mixture was stirred at 60° C. for 2 hours. After 2 hours the reaction mixture was cooled to room temperature and added slowly to brine. The brine was extracted three times with ethyl acetate, dried over magnesium sulfate, filtered, and evaporated to obtain 13.84 gm of crude compound 18 (MH+=505).

Step J

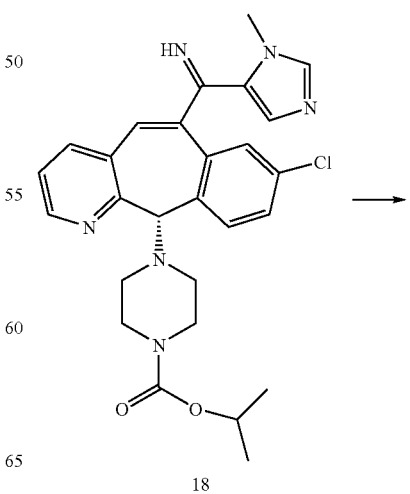

18

127

-continued

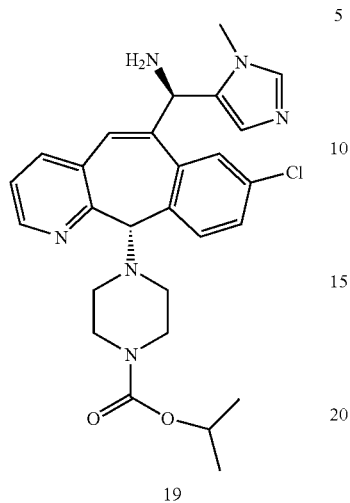

19

To an ice bath cooled stirred solution of 18 (13.84 gm, ~24.7 mmol) in 250 ml of methanol at 0° C. was added sodium borohydride (4.13 gm, 100 mmol) over 15 minutes. The reaction mixture was stirred for 1 hour. The reaction mixture was slowly added to cold stirred 1N HCL (330 ml). The mixture was added to 385 ml of 1N sodium hydroxide and the aqueous mixture was extracted four times with ethyl acetate, dried over magnesium sulfate, filtered, and evaporated to give 11.94 gm of compound 19 (MH+=507)

Step K

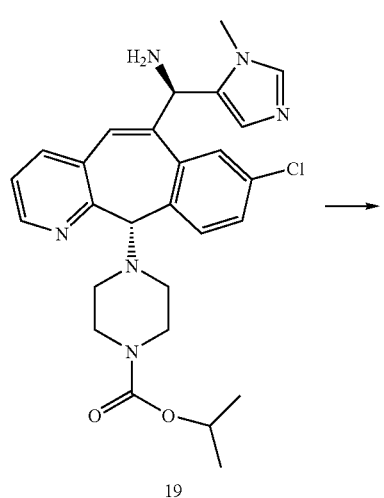

19

128

-continued

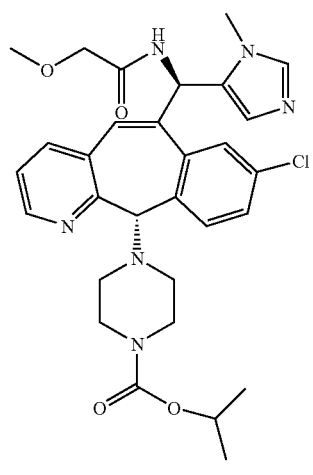

175.1

To a ice cooled solution of 19 (~24.7 mmol) in 217 ml of dichloromethane was added triethylamine (10.3 ml, 74 mmol). Methoxyacetyl chloride (2.7 ml, 29 mmol) was added dropwise and stirred. After 2 hrs. the reaction mixture was washed with brine, dried over magnesium sulfate, and filtered. The crude product was chromatographed on a silica gel column using 20% hexane/acetone with 0.2% ammonium hydroxide to obtain 7.9 gm of compound which was further purified on silica gel using 2% methanol/dichloromethane to obtain 7 gm of 20 (MH+=579).

M

EXAMPLE 2

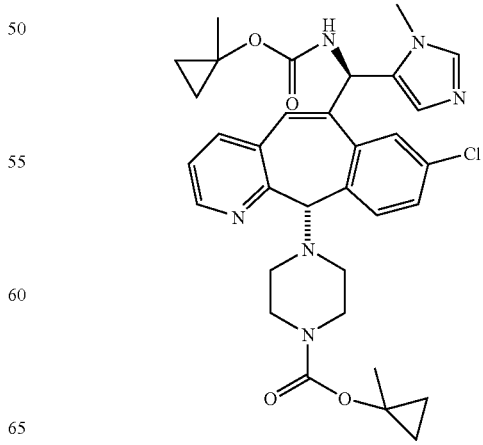

Scheme 2
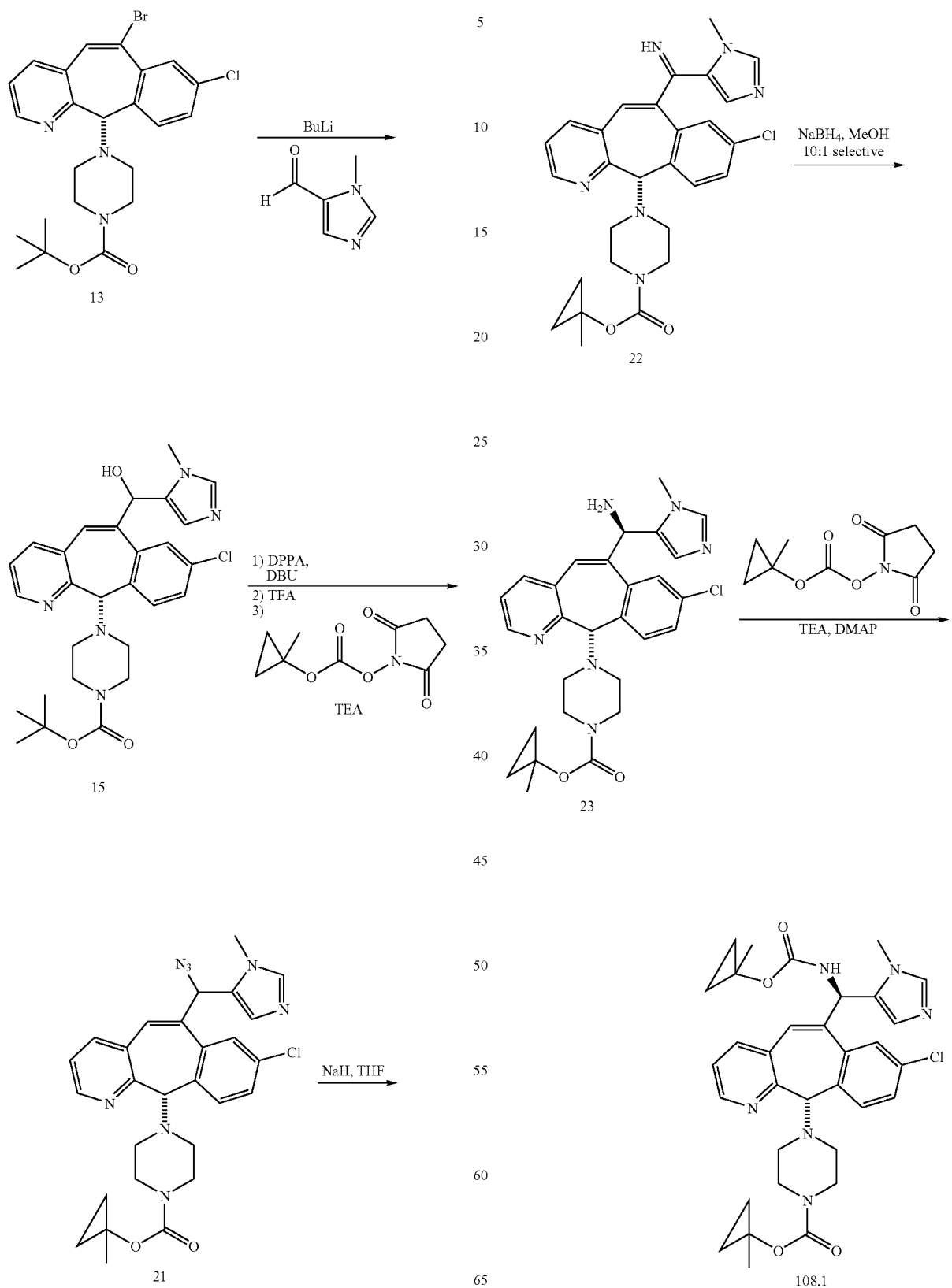

Step A

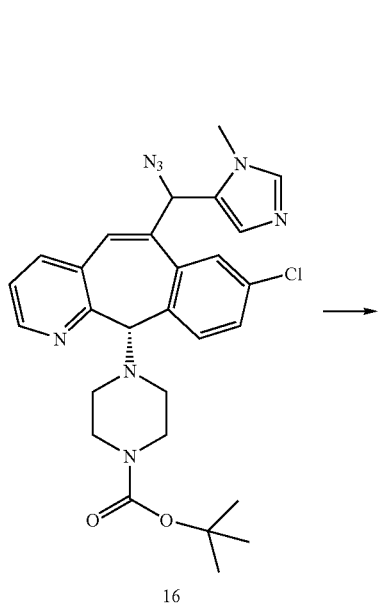

16

To a solution of 16 (Example 1 Step G) (7.98 gm, 14.6 mmol) in 150 ml of dichloromethane was added 15 ml of trifluoroacetic acid. The reaction mixture was stirred for 3 hours, evaporated to dryness followed by evaporation from toluene. The crude product was dissolved in 100 ml of dichloromethane and triethylamine (20.35 ml, 146 mmol) was added. Carbonic acid 2,5-dioxo-pyrrolidin-1-yl ester 1-methyl-cyclopropyl ester (3.89 gm, 18.25 mmol)) was added and the reaction mixture stirred for 1 hour. The reaction mixture was added to brine, extracted three times with ethyl acetate, dried over magnesium sulfate, filtered and evaporated to obtain a solid. The crude product was chromatographed on silica gel using 2-5% methanol/dichloromethane as eluent to obtain 7.44 gm of compound 21 (MH+=545).

Step B

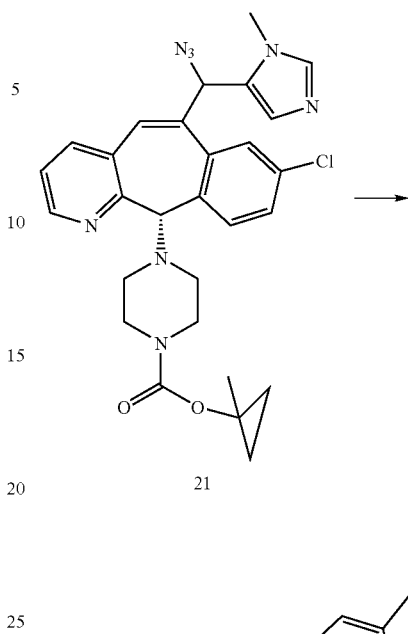

21

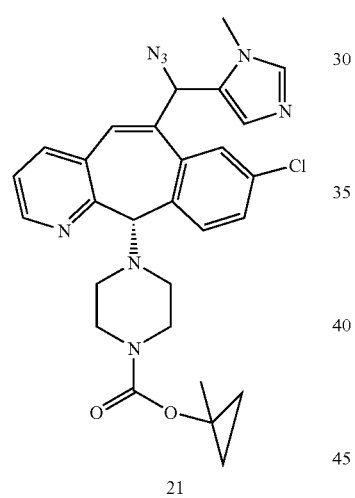

21

To a solution of 21 (7.24 gm, 13.3 mmol) in 150 ml of tetrahydrofuran was added sodium hydride (60% oil dispersion, 1.5 gm, 39.9 mmol). The reaction mixture was stirred at 60° C. for 2 hours. After 3-4 hours the reaction mixture was cooled to room temperature and added slowly to brine. The brine was extracted three times with ethyl acetate, dried over magnesium sulfate, filtered, and evaporated to obtain 7.54 gm of crude compound 22.

Step C

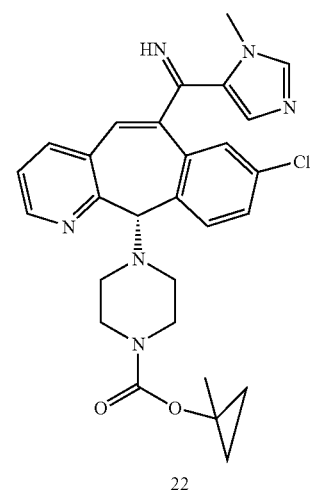

22

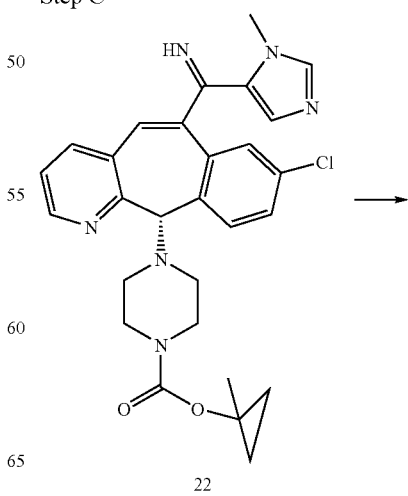

22

133
-continued

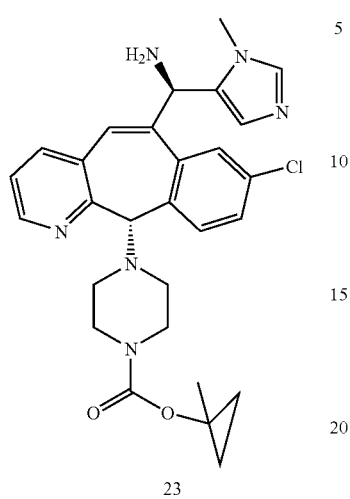

23

To a ice bath cooled stirred solution of 22 (7.34 gm, 12.94 mmol) in 150 ml of methanol at 0° C. was added sodium borohydride (1.47 gm, 38.82 mmol) over 15 minutes. The reaction mixture was stirred for 1 hour. The reaction mixture was slowly added to cold stirred 1N HCL (150 ml). The mixture was added to 175 ml of 1N sodium hydroxide and the aqueous mixture extracted four times with ethyl acetate, dried over magnesium sulfate, filtered, and evaporated to give 7.15 gm of compound 23 which was used in the next step.

Step D

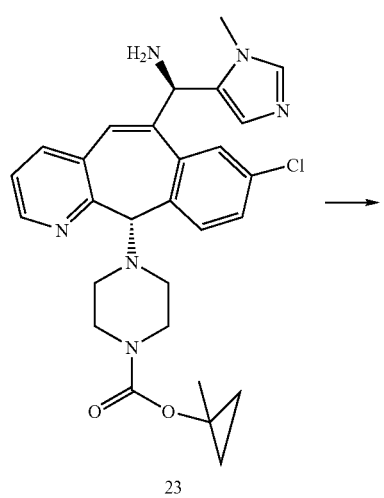

23

134
-continued

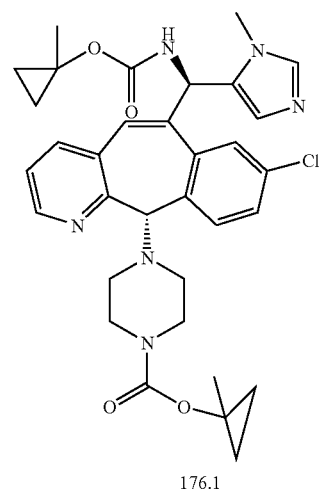

176.1

To a ice cooled solution of 23 (7.15 gm, 12.94 mmol) in 100 ml of dichloromethane was added triethylamine (5.41 ml, 38.82 mmol) and 4-dimethylaminopyridine (0.1 gm, 0.82 mmol). Carbonic acid 2,5-dioxo-pyrrolidin-1-yl ester 1-methyl-cyclopropyl ester (4.138 gm, 19.41 mmol) was added and the reaction mixture stirred at reflux. After 18 hrs. the reaction mixture was washed with brine, dried over magnesium sulfate, and filtered. The crude product was chromatographed on a silica gel column using 0.5%-5% methanol/dichloromethane to obtain 6.0 gm of compound 24 (MH+=617).

EXAMPLE 3

4-{8-Chloro-6-[[(1-methoxy-cyclopropanecarbonyl)-amino]-(3-methyl-3H-imidazol-4-yl)-methyl]-11H-benzo[5.6]cyclohepta[1,2-b]pyridin-11-yl}-piperazine-1-carboxylic acid isopropyl ester

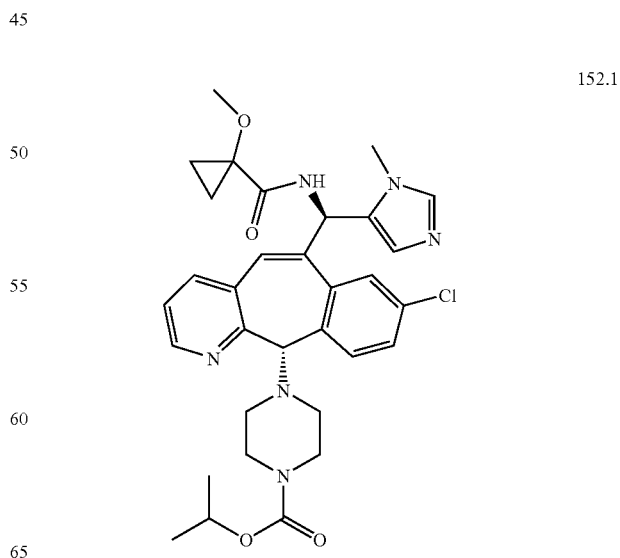

152.1

Step A: 1-Methoxy-cyclopropanecarboxylic acid methyl ester

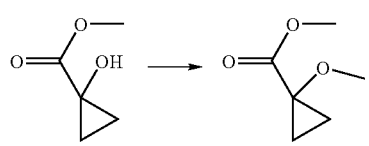

1-Hydroxy-cyclopropanecarboxylic acid methyl ester (1.16 gm, 10 mmol) was dissolved in 10 ml of tetrahydrofuran and cooled under a nitrogen atmosphere to 0° C. Sodium hydride (0.52 gm, 60% oil dispersion) was added portionwise followed by Iodomethane (1 ml) and stirred for 18 hrs. The reaction mixture was quenched with ammonium chloride and extracted with ethylacetate to obtain 2 gm of title product. (MH+=130)

Step B: 1-Methoxy-cyclopropanecarboxylic acid

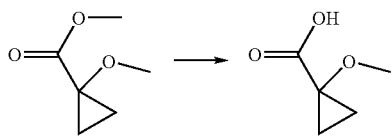

1-Methoxy-cyclopropanecarboxylic acid methyl ester from above was dissolved in 10 ml of tetrahydrofuran and 7 ml of 5 M sodium hydroxide added. After stirring for 18 hrs the reaction mixture was acidified with conc. hydrochloric acid, extracted with ethylacetate, and dried over magnesium sulfate. The filtrate was evaporated to obtain 0.72 gm of light yellow oil as title product.

Step C: 4-{8-Chloro-6-[[(1-methoxy-cyclopropanecarbonyl)-amino]-(3-methyl-3H-imidazol-4-yl)-methyl]-11H-benzo[5,6]cyclohepta[1,2-b]pyridin-11-yl}-piperazine-1-carboxylic acid isopropyl ester

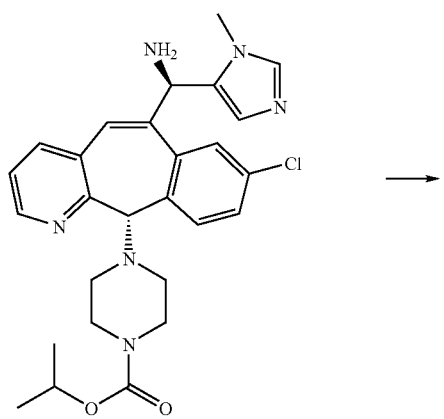

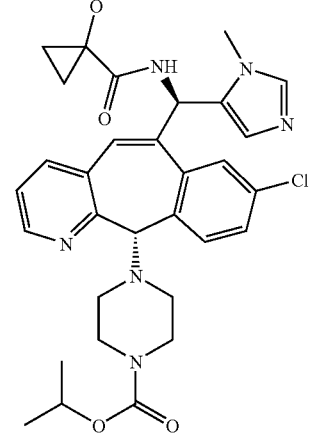

152.1

Compound 19 (Example 1 Step J) (52 mg, 0.1 mmol) was dissolved in 5 ml of dichloromethane. While stirring 1-Methoxy-cyclopropanecarboxylic acid (21 mg, 0.18 mmol), 1-hydroxybenztriazole (16 gm, 0.12 mmol), 1-(3-dimethylaminopropyl)-3-ethylcarbodiimide hydrochloride (46 mg, 0.24 mmol), and N-methylmorpholine (0.15 ml) was added. The reaction mixture was stirred at ambient temperature under a nitrogen atmosphere. After 18 hrs the reaction mixture was washed with brine and the organic layer concentrated to a yellow solid. The final product was obtained after chromatography on preparative thin layer silica using 10% methanol/dichloro-methane as the eluent to obtain 45 mg of title product (MH+=605).

EXAMPLE 4

4-{8-Chloro-6-[[(1-hydroxy-cyclopropanecarbonyl)-amino]-(3-methyl-3H-imidazol-4-yl)-methyl]-11H-benzo[5,6]cyclohepta[1,2-b]pyridin-11-yl}-piperazine-1-carboxylic acid isopropyl ester

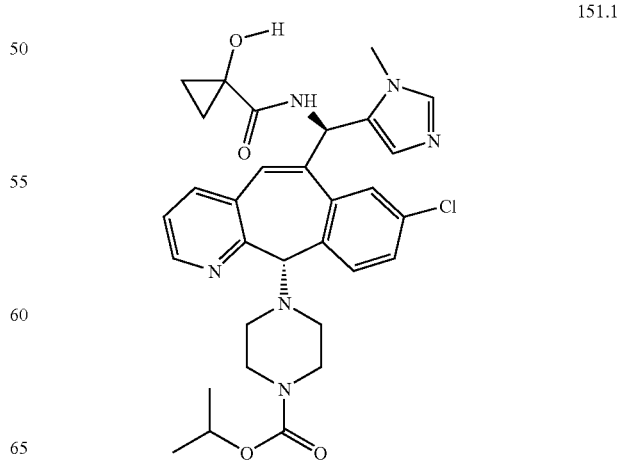

151.1

Compound 151.1 was obtained by following a similar procedure to that of Example 3, except substituting 1-hydroxycyclopropanecarboxylic acid for 1-methoxycyclopropanecarboxylic acid.

EXAMPLE 5

General Procedure for Introduction of the Amide Group

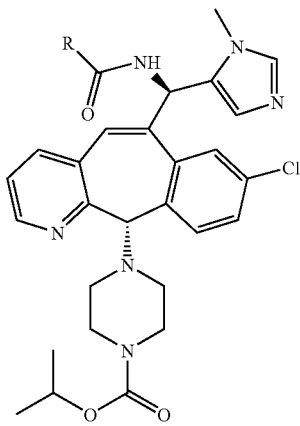

Amides of the above compound were prepared following a procedure similar to Examples 3 and 4, either from the commercially available carboxylic acid followed by reaction with 1-hydroxybenztriazole, 1-(3-dimethylaminopropyl)-3-ethylcarbodiimide hydrochloride, and N-methylmorpholine, or by reaction of compound 19 (Example 1 Step J) with the appropriate commercially available carboxylic acid chloride in the presence of triethylamine base.

EXAMPLE 6

Carbonic acid bicyclopropyl-1-yl ester 2,5-dioxo-pyrrolidin-1-yl ester

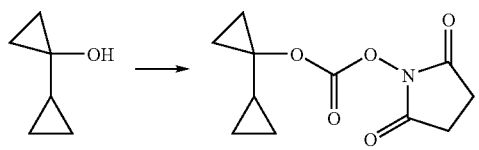

Bicyclopropyl-1-ol was prepared according to O. G. Kulinkovich, et.al. Synthesis, 3, 1991, p. 234. Bicyclopropyl-1-ol (2 gm) was dissolved in 100 ml of acetonitrile and 7.7 gm of di-succinimidylcarbonate was added in the presence of 9 ml of triethyl amine. The reaction mixture was stirred at ambient temperature for 18 hrs. The reaction mixture was washed with saturated sodium bicarbonate, followed by brine and dried over magnesium sulfate. The solvent was evaporated to obtain 1.6 gm of title compound.

EXAMPLE 7

General Procedure for Introduction of the Carbamate Group

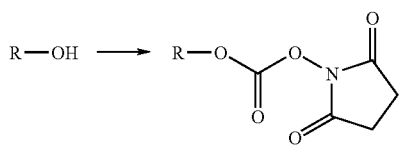

Carbamates were prepared following a procedure similar to that of Example 6 by preparing the N-hydroxy succinimide carbonate of the corresponding alcohol. The appropriate alcohol was reacted with di-succinimidylcarbonate in the presence of triethyl amine. After being stirred at ambient temperature for 18 hrs, the reaction mixture was washed with saturated sodium bicarbonate, followed by brine and dried over magnesium sulfate. The solvent was evaporated to obtain the desired product.

EXAMPLE 8

Step A: 4-{6-[Amino-(3-methyl-3H-imidazol-4-yl)-methyl]-8-chloro-11H-benzo[5,6]cyclohepta-[1,2-b]pyridin-11-yl}-piperazine-1-carboxylic acid cyclopentyl ester

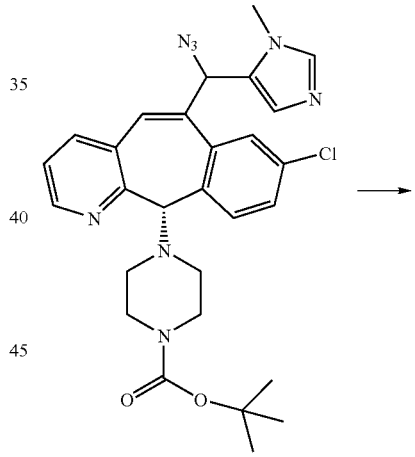

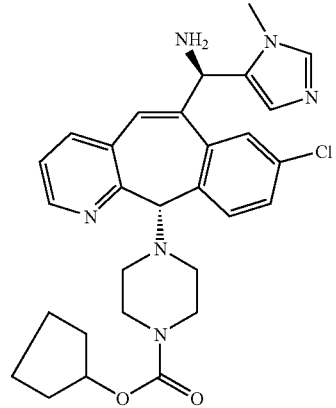

4-{6-[Amino-(3-methyl-3H-imidazol-4-yl)-methyl]-8-chloro-11H-benzo[5,6]cyclohepta[1,2-b]pyridin-11-yl}piperazine-1-carboxylic acid cyclopentyl ester was prepared from compound, 16 following a procedure similar to that of Example 1 Steps I and J, by substituting cyclopentylchloroformate for isopropylchloroformate.

Step B: 4-{6-[(Bicyclopropyl-1-yloxycarbonylamino)-(3-methyl-3H-imidazol-4-yl)-methyl]-8-chloro-11H-benzo[5,6]cyclohepta[1,2-b]pyridin-11-yl}-piperazine-1-carboxylic acid cyclopentyl ester

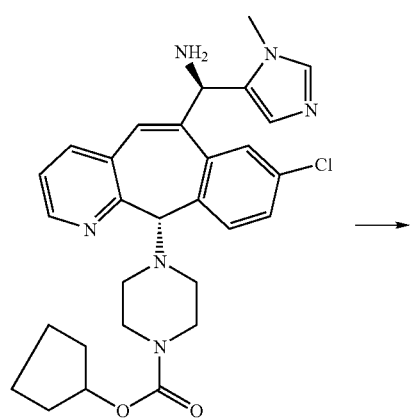

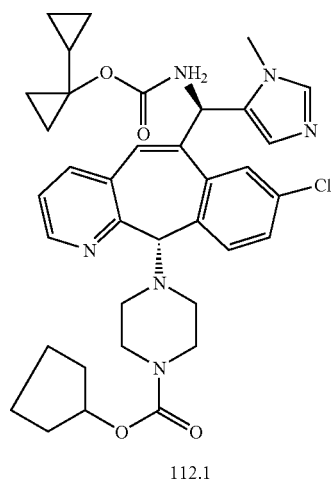

112.1

4-{6-[Amino-(3-methyl-3H-imidazol-4-yl)-methyl]-8-chloro-11H-benzo[5,6]cyclohepta[1,2-b]pyridin-11-yl}-piperazine-1-carboxylic acid cyclopentyl ester (60 mg, 0.11 mmol) was dissolved in 5 ml of dichloromethane and 0.2 ml of triethyl amine. Carbonic acid bicyclopropyl-1-yl ester 2,5-dioxo-pyrrolidin-1-yl ester (45 mg, 0.19 mmol) was added and the reaction mixture stirred for 18 hours at ambient temperature under a dry nitrogen atmosphere. The reaction mixture was washed with brine and evaporated to a solid. The solid was chromatographed on silica gel using 5% methanol/dichloromethane as eluent to obtain 49 mg of title product.

The remaining compounds of the invention can be prepared following procedures similar to those of Examples 1 to 8.

| Mass Spectroscopy Data For Compounds Of The Invention | | | | | |
|---|---|---|---|---|---|
| Compound | MS MH+ | Compound | MS MH+ | Compound | MS MH+ |
| 100.1 | 589 | 101.1 | 575 | 102.1 | 633 |
| 102.2 | 633 | 103.1 | 619 | 104.1 | 619 |
| 105.1 | 605 | 106.1 | 605 | 109 | 631 |
| 108.1 | 617 | 109.1 | 671 | 110.1 | 603 |
| 111.1 | 633 | 112.1 | 657 | 113.1 | 659 |
| 114.1 | 633 | 115.1 | 619 | 116.1 | 633 |
| 117.1 | 631 | 118.1 | 645 | 119.1 | 633 |
| 120.1 | 630 | 121.1 | 646 | 122.1 | 689 |
| 123.1 | 754 | 124.1 | 647 | 125.1 | 724 |
| 126.1 | 617 | 127.1 | 617 | 128.1 | 724 |
| 129.1 | 663 | 130.1 | 746 | 131.1 | 593 |
| 132.1 | 633 | 133.1 | 621 | 134.1 | 605 |
| 135.1 | 607 | 135.2 | 607 | 136.1 | 579 |
| 137.1 | 565 | 138.1 | 563 | 139.1 | 593 |
| 140.1 | 619 | 141.1 | 600 | 142.1 | 593 |
| 143.1 | 606 | 144.1 | 622 | 145.1 | 635 |
| 146.1 | 593 | 147.1 | 607 | 148.1 | 574 |
| 149.1 | 593 | 150.1 | 593 | 151.1 | 591 |
| 152.1 | 605 | 153.1 | 619 | 154.1 | 605 |
| 155.1 | 591 | 156.1 | 607 | 157.1 | 577 |
| 158.1 | 591 | 159.1 | 617 | 160.1 | 621 |
| 161.1 | 635 | 162.1 | 579 | 163.1 | 720 |
| 164.1 | 620 | 165.1 | 606 | 166.1 | 651 |
| 167.1 | 605 | 168.1 | 605 | 169.1 | 619 |
| 170.1 | 585 | 171.1 | 681 | 173.1 | 607 |
| 174.1 | 621 | — | — | — | — |

Assays

FPT activity was determined by measuring the transfer of [$^3$H] farnesyl from [$^3$H] farnesyl pyrophosphate to a biotinylated peptide derived from the C-terminus of H-ras (biotin-CVLS). The reaction mixture contains: 50 mM Tris pH7.7, 5 mM MgCl$_2$, 5 μM Zn$^{++}$, 5 mM DTT, 0.1% Triton-X, 0.05 μM peptide, 0.03 nM purified human farnesyl protein transferase, 0.180 μM [$^3$H] farnesyl pyrophosphate, plus the indicated concentration of tricyclic compound or vehicle control in a total volume of 100 μl. The reaction was incubated in a yortemp shaking incubator at 37° C., 45 RPM for 60 minutes and stopped with 150 μl of 0.25 M EDTA containing 0.5% BSA and 1.3 mg/ml Streptavidin SPA beads. Radioactivity was measured in a Wallach 1450 Microbeta liquid scintillation counter. Percent inhibition was calculated relative to the vehicle control.

COS Cell IC$_{50}$ (Cell-Based Assay) could be determined following the assay procedures described in WO 95/10516, published Apr. 20, 1995. GGPT IC$_{50}$ (inhibition of geranylgeranyl protein transferase, in vitro enzyme assay), Cell Mat Biochemical assay and anti-tumor activity (in vivo anti-tumor studies) could be determined by the assay procedures described in WO 95/10516. The disclosure of WO 95/10516 is incorporated herein by reference thereto.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of farnesyl transferase inhibitor as the top layer. After the top layer is solidified, plates can be incubated for 10-16 days at 37° C. under 5% CO$_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the $IC_{50}$'s can be determined.

The compounds of this invention have an FPT $IC_{50}$ in the range of <0.5 nM to >20 nM and a Soft Agar $IC_{50}$ in the range of <0.5 nM to >100 nM.

The compounds of formulas 100.1, 101.1, 102.1, 102.2, 103.1, 104.1, 105.1, 106.1, 107.1, 108.1,109.1, 110.1, 111.1, 112.1,113.1, 114.1, 115.1,116.1, 117.1, 118.1, 119.1, 120.1, 124.1, 125.1, 127.1,131.1, 133.1, 134.1, 135.1, 135.2, 136.1, 139.1, 140.1, 143.1, 147.1, 150.1, 152.1, 153.1, 154.1, 155.1, 156.1, 157.1, 158.1, 160.1, 161.1, 167.1, 168.1, 169.1, 173.1, and 174.1 have an FPT $IC_{50}$ in the range of <0.5 nM to 5 nM and a Soft Agar $IC_{50}$ in the range of <0.5 nM to >5 nM.

The compound of formula 108.1 had an FPT $IC_{50}$ of 1.5 nM, and a Soft Agar $IC_{50}$ of <0.5 nM. The compound of formula 136.1 had an FPT $IC_{50}$ of 0.6 nM, and a Soft Agar $IC_{50}$ of 0.6 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, $20^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

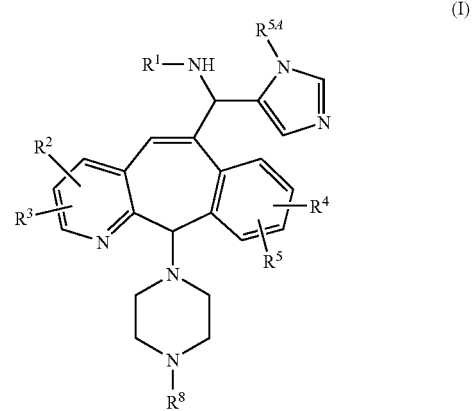

(I)

and the pharmaceutically acceptable salts thereof, wherein:

$R^1$ is selected from the group consisting of:

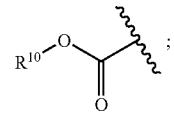

$R^2$, $R^3$, and $R^4$ are H, and $R^5$ is selected from the group consisting of: H, Br, Cl, and F;

$R^{5A}$ is selected from the group consisting of a H and $C_1$ to $C_6$ alkyl group;

$R^8$ is selected from the group consisting of:

H,

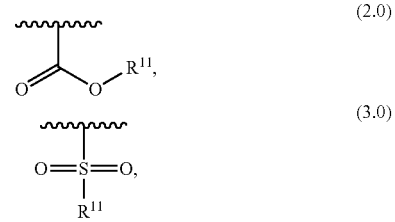

143

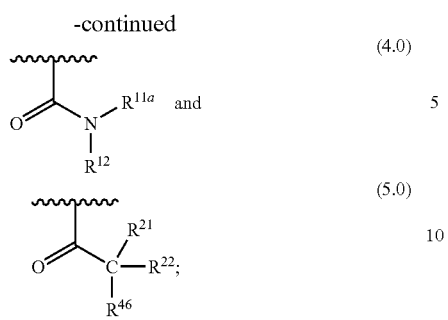

$R^{9a}$ is selected from the group consisting of: alky and arylalkyl;

$R^{10}$ is cycloalkyl; wherein said $R^{10}$ group is substituted with 1 to 3 substituents independently selected from the group consisting of: —OH, halo, alkyl, cycloalkyl, —NH$_2$, —NH(C$_1$ to C$_6$ alkyl), —N(C$_1$ to C$_6$ alkyl)$_2$ wherein each alkyl group is independently selected, alkoxy, and —CO$_2$R$^{14}$ wherein R$^{14}$ is selected from the group consisting of: H and alkyl;

$R^{11}$ is selected from the group consisting of: (1) alkyl (2) substituted alkyl, (3) unsubstituted aryl, (4) substituted aryl, (5) unsubstituted cycloalkyl, (6) substituted cycloalkyl, (7) unsubstituted heteroaryl, (8) substituted heteroaryl, (9) hetero-cycloalkyl, and (10) substituted heterocycloalkyl; wherein said substituted alkyl, substituted cycloalkyl, and substituted heterocycloalkyl $R^{11}$ groups are substituted with one or more substituents independently selected from the group consisting of: (1) —OH, provided that when there is more than one —OH group then each —OH group is bound to a different carbon atom, (2) fluoro, and (3) alkyl; and wherein said substituted aryl and substituted heteroaryl $R^{11}$ groups are substituted with one or more substituents independently selected from the group consisting of: (1) —OH, provided that when there is more than one —OH group then each —OH group is bound to a different carbon atom, (2) halogen, and (3) alkyl;

$R^{11a}$ is selected from the group consisting of: (1) H, (2) OH, (3) alkyl, (4) substituted alkyl, (5) aryl, (6) substituted aryl, (7) unsubstituted cycloalkyl, (8) substituted cycloalkyl, (9) unsubstituted heteroaryl, (10) substituted heteroaryl, (11) heterocycloalkyl, (12) substituted heterocycloalkyl, and (13) —OR$^{9a}$; wherein said substituted alkyl, substituted cycloalkyl, and substituted heterocycloalkyl $R^{11a}$ groups are substituted with one or more substituents independently selected from the group consisting of: (1) —OH, provided that when there is more than one —OH group then each —OH group is bound to a different carbon atom, (2) —CN, (3) —CF$_3$, (4) fluoro, (5) alkyl, (6) cycloalkyl, (7) heterocycloalkyl, (8) arylalkyl, (9) heteroarylalkyl, (10) alkenyl and (11) heteroalkenyl; and wherein said substituted aryl and substituted heteroaryl $R^{11a}$ groups have one or more substituents independently selected from the group consisting of: (1) —OH, provided that when there is more than one —OH group then each —OH group is bound to a different carbon atom, (2) —CN, (3) —CF$_3$, (4) halogen, (5) alkyl, (6) cycloalkyl, (7) heterocycloalkyl, (8) arylalkyl, (9) heteroarylalkyl, (10) alkenyl, and (11) heteroalkenyl;

144

$R^{12}$ is selected from the group consisting of: H, alkyl, piperidine Ring V, cycloalkyl, and —alkyl-(piperidine Ring V), wherein piperidine Ring V is

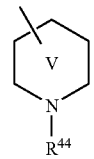

wherein $R^{44}$ is selected from the group consisting of: (a) —H, (b) alkyl, (c) alkylcarbonyl, (d) alkyloxycarbonyl, (e) haloalkyl, and (f) —C(O)NH(R$^{51}$);

$R^{21}$, $R^{22}$ and $R^{46}$ are independently selected from the group consisting of: (1) —H, (2) alkyl (e.g., methyl, ethyl, propyl, butyl or t-butyl), (3) unsubstituted aryl, (4) substituted aryl substituted with one or more substituents independently selected from the group consisting of: alkyl, halogen, CF$_3$ and OH, (5) unsubstituted cycloalkyl, (6) substituted cycloalkyl substituted with one or more substituents independently selected from the group consisting of: alkyl, halogen, CF$_3$ and OH, (7) heteroaryl of the formula

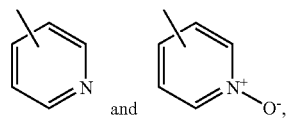

(8) heterocycloalkyl of the formula:

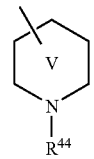

wherein $R^{44}$ is selected from the group consisting of: (a) —H, (b) alkyl, (c) alkylcarbonyl, (d) alkyloxycarbonyl, (e) haloalkyl, and (f) —C(O)NH(R$^{51}$), (9) —NH$_2$ provided that only one of R$^{21}$, R$^{22}$, and R$^{46}$ group can be —NH$_2$ and provided that when one of R$^{21}$, R$^{22}$, and R$^{46}$ is —NH$_2$ then the remaining groups are not —OH, (10) —OH provided that only one of R$^{21}$, R$^{22}$, and R$^{46}$ group can be —OH and provided that when one of R$^{21}$, R$^{22}$, and R$^{46}$ is —OH then the remaining groups are not —NH$_2$, and (11) alkyl substituted with one or more substituents selected from the group consisting of: —OH and —NH$_2$ and provided that there is only one —OH or one —NH$_2$ group on a substituted carbon, or $R^{21}$ and $R^{22}$ taken together with the carbon to which they are bound form a cyclic ring selected from the group consisting of: (1) unsubstituted cycloalkyl, (2) cycloalkyl substituted with one or more substituents independently selected from the group consisting of: alkyl, halogen, CF$_3$ and OH, (3) unsubstituted cycloalkenyl, (4) cycloalkenyl substituted with one or more substituents independently selected from the group consisting of: alkyl, halogen, CF$_3$ and OH, (5) heterocycloalkyl, (6) unsubstituted aryl, (7) aryl substituted with one or more substituents independently selected from the group consisting of: alkyl, halogen, —CN, —CF$_3$, OH and alkoxy, and (8) heteroaryl selected from the group consisting of:

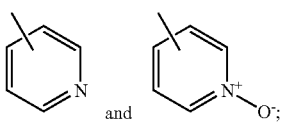

and $R^{51}$ is selected from the group consisting of: H and alkyl.

2. The compound of claim 1 wherein $R^5$ is 8-Cl.

3. The compound of claim 1 wherein said compound has the structure (II)

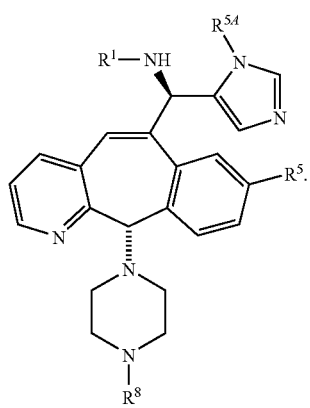

4. The compound of claim 3 wherein $R^5$ is Cl.

5. The compound of claim 1 having the structure:

(IIA)

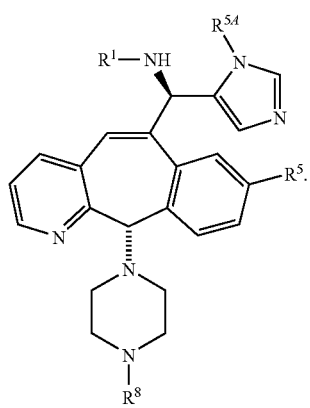

6. The compound of claim 5 wherein $R^5$ is Cl.

7. The compound of claim 1 having the formula:

(VI)

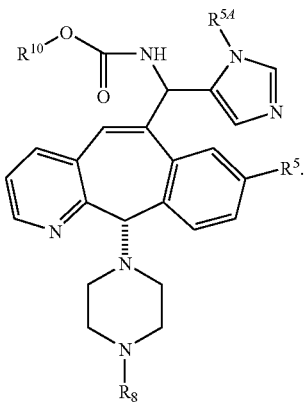

8. The compound of claim 1 having the formula:

(VII)

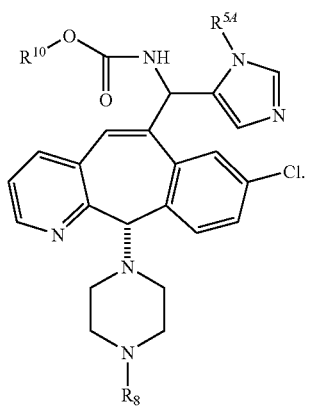

9. The compound of claim 1 having the formula:

(VIA)

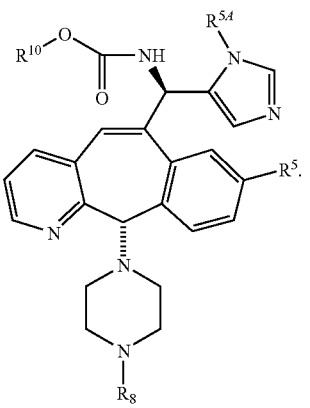

10. The compound of claim 1 having the formula:

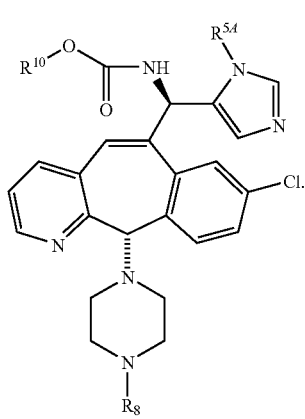

(VIIA)

11. The compound of claim 1 wherein $R^{5A}$ is selected from the group consisting of: H, methyl, ethyl and isopropyl.

12. The compound of claim 1 wherein $R^{5A}$ is methyl.

13. The compound of claim 1 wherein $R^{10}$ is cycloalkyl substituted with a $C_1$ to $C_6$ alkyl group.

14. The compound of claim 1 wherein $R^{10}$ is cycloalkyl substituted with methyl.

15. The compound of claim 1 wherein $R^{10}$ is:

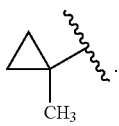

16. The compound of claim 1 wherein $R^8$

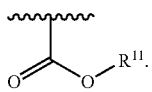

17. The compound of claim 1 wherein $R^1$ is

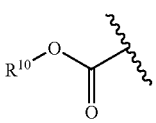

and $R^8$ is

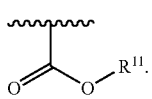

18. The compound of claim 17 wherein $R^{10}$ and $R^{11}$ are the same substituted cycloalkyl.

19. The compound of claim 18 wherein $R^{10}$ and $R^{11}$ are:

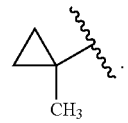

20. The compound of claim 1 wherein $R^1$ is

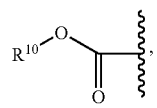

$R^{10}$ is cycloalkyl substituted with a $C_1$ to $C_6$ alkyl group, and $R^8$ is

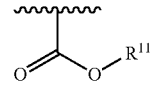

wherein $R^{11}$ is selected from the group consisting of: unsubstituted cycloalkyl and substituted cycloalkyl.

21. The compound of claim 1 having the formula:

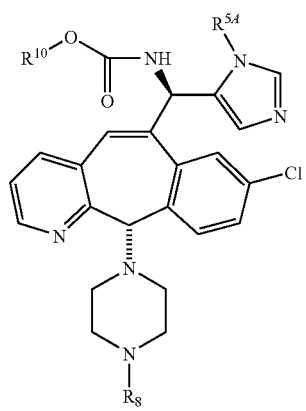

(VIIA)

wherein: (1) $R^{5A}$ is selected from the group consisting of: H, methyl, ethyl, and isopropyl, (2) $R^{10}$ is cycloalkyl substituted with a $C_1$ to $C_6$ alkyl group, and $R^8$ is

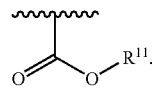

22. The compound of claim 21 wherein $R^{11}$ is selected from the group consisting of: unsubstituted cycloalkyl and substituted cycloalkyl.

23. The compound of claim 22 wherein $R^{10}$ and $R^{11}$ are the same.

24. The compound of claim 23 wherein $R^{10}$ and $R^{11}$ are
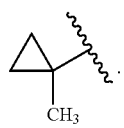
25. The compound of claim 1 in isolated and purified form.
26. A pharmaceutical composition comprising at least one compound of claim 1 and a pharmaceutically acceptable carrier.
27. A compound selected from the group consisting of:
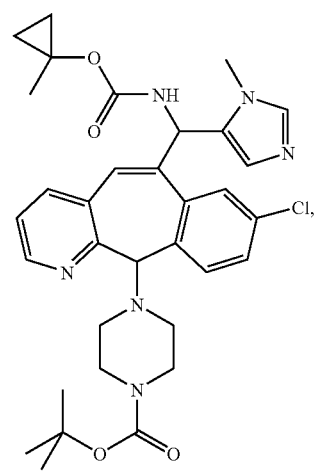
104
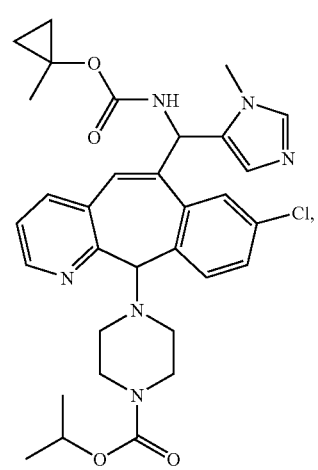
105
-continued
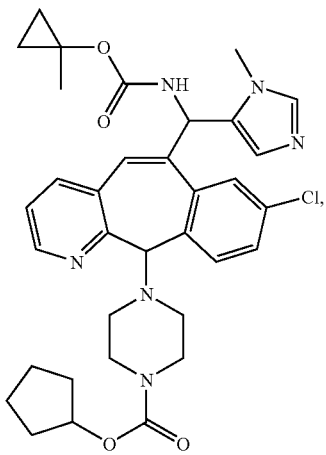
107
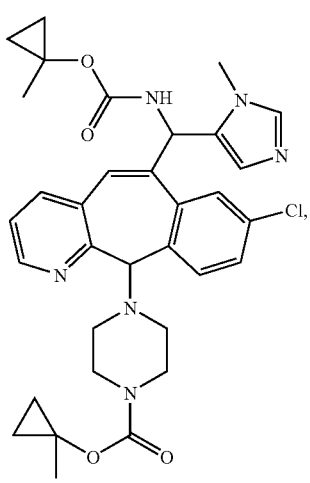
108
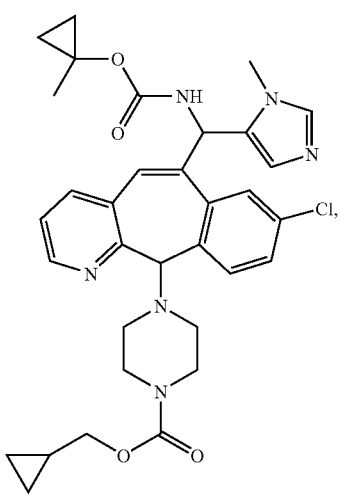
109

151 152

-continued
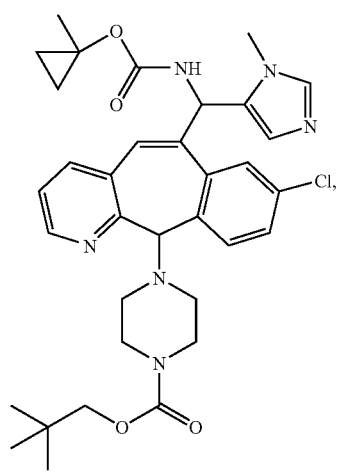
116
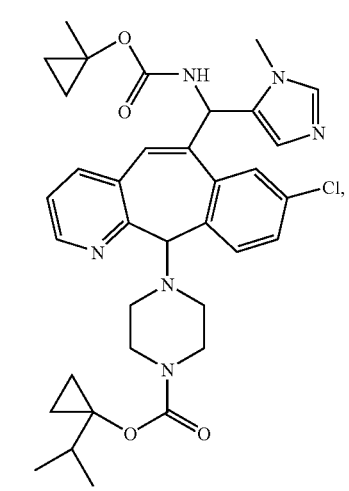
117
118
28. The compound of claim 27 selected from the group consisting of:
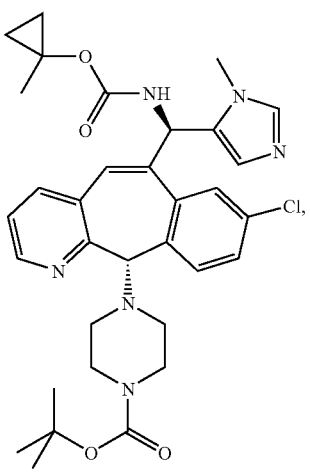
104.1
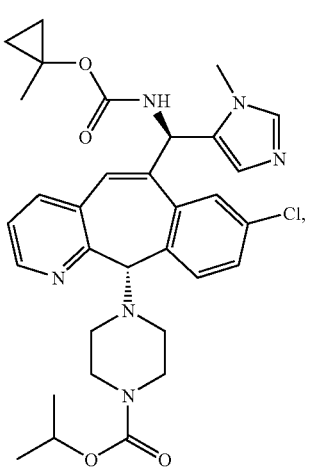
105.1
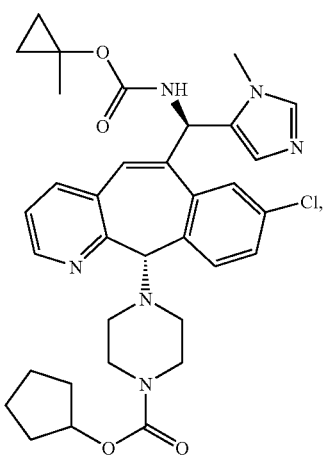
107.1
or a pharmaceutically acceptable salt thereof.

108.1
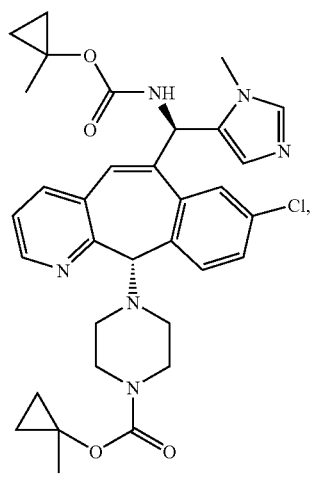
109.1
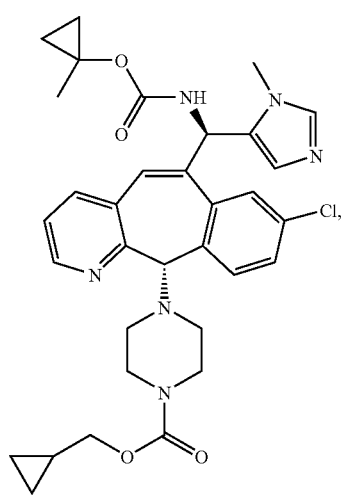
110.1
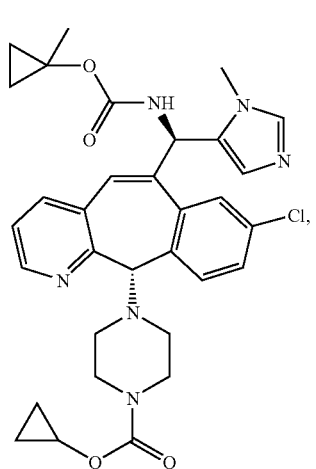
111.1
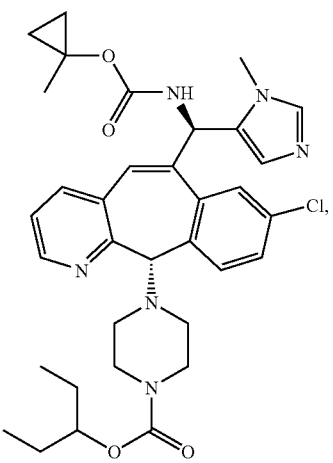
112.1
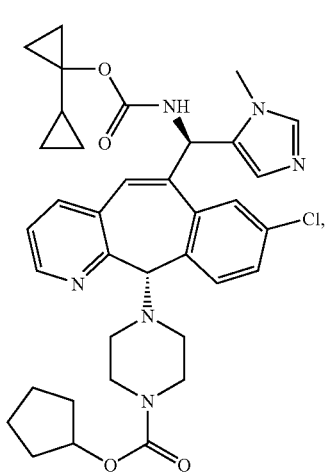
113.1
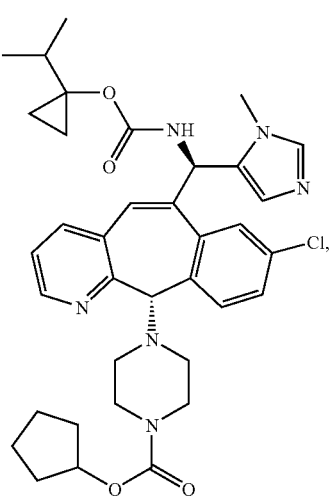

-continued
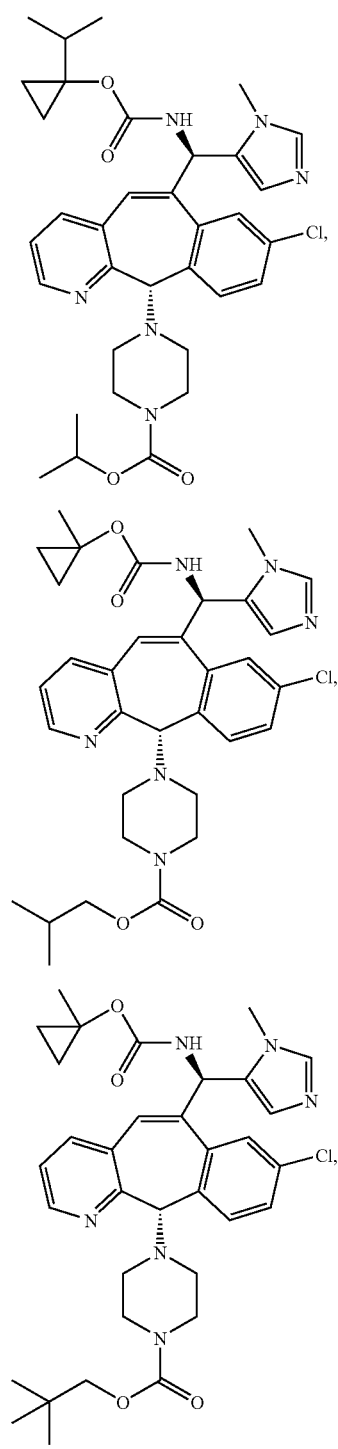
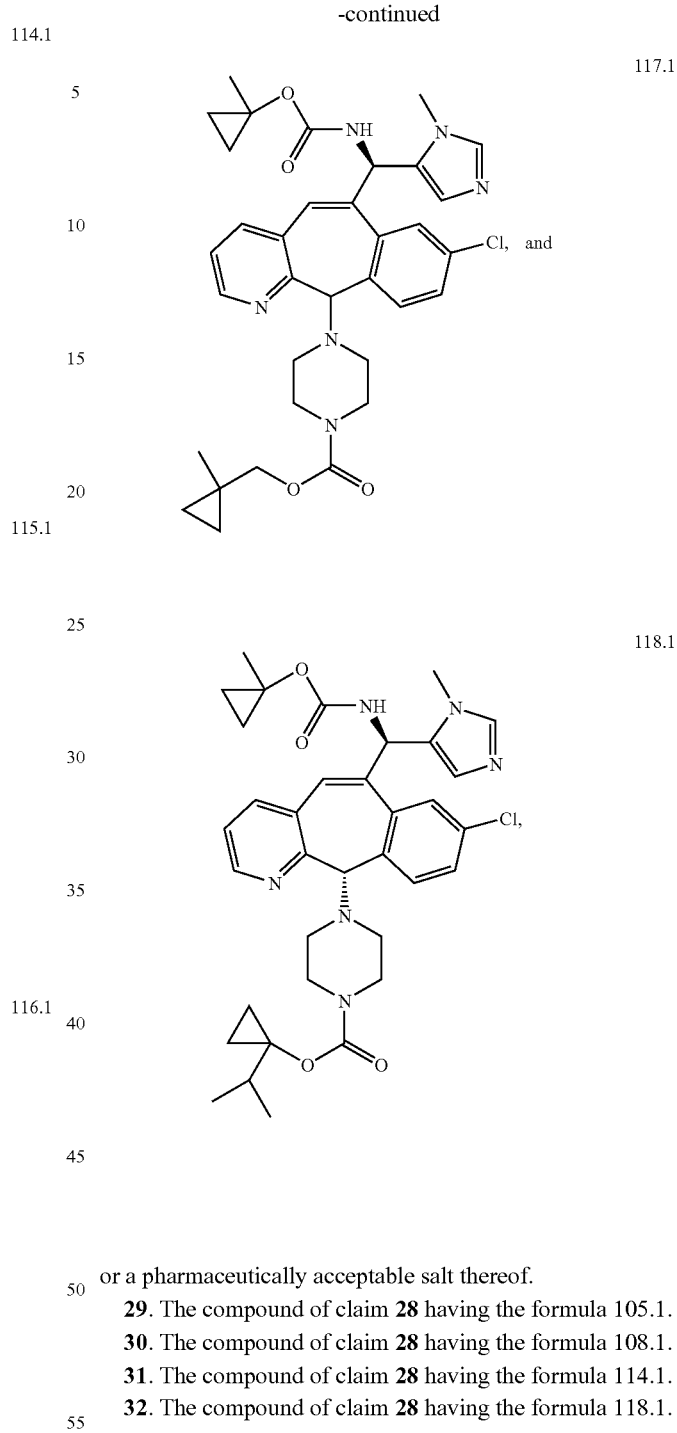
or a pharmaceutically acceptable salt thereof.
29. The compound of claim 28 having the formula 105.1.
30. The compound of claim 28 having the formula 108.1.
31. The compound of claim 28 having the formula 114.1.
32. The compound of claim 28 having the formula 118.1.
* * * * *